United States Patent
Perry et al.

(10) Patent No.: US 11,564,673 B2
(45) Date of Patent: Jan. 31, 2023

(54) DELIVERY SYSTEMS FOR CONTROL OF GASTROINTESTINAL BLEEDING

(71) Applicants: TRICOL BIOMEDICAL, INC., Portland, OR (US); OREGON HEALTH & SCIENCE UNIVERSITY, Portland, OR (US)

(72) Inventors: Kenneth E. Perry, Bainbridge Island, WA (US); Kenneth P. Perry, Bainbridge Island, WA (US); Hua Xie, Portland, OR (US); Brintha Enestvedt, Portland, OR (US); Simon J. McCarthy, Portland, OR (US)

(73) Assignees: Tricol Biomedical, Inc., Portland, OR (US); Oregon Health & Science University, Portland, OR (US)

( * ) Notice: Subject to any disclaimer, the term of this patent is extended or adjusted under 35 U.S.C. 154(b) by 77 days.

(21) Appl. No.: 16/958,304

(22) PCT Filed: Dec. 28, 2018

(86) PCT No.: PCT/US2018/067991
§ 371 (c)(1),
(2) Date: Jun. 26, 2020

(87) PCT Pub. No.: WO2019/133894
PCT Pub. Date: Jul. 4, 2019

(65) Prior Publication Data
US 2021/0052261 A1      Feb. 25, 2021

Related U.S. Application Data

(60) Provisional application No. 62/612,000, filed on Dec. 29, 2017.

(51) Int. Cl.
*A61B 17/00* (2006.01)

(52) U.S. Cl.
CPC .... *A61B 17/0057* (2013.01); *A61B 17/00234* (2013.01); *A61B 2017/0034* (2013.01);
(Continued)

(58) Field of Classification Search
CPC .......... A61B 17/00234; A61B 17/0057; A61B 2017/0034; A61B 2017/00557;
(Continued)

(56) References Cited

U.S. PATENT DOCUMENTS

| 7,371,403 B2 | 5/2008 | McCarthy et al. |
| 7,482,503 B2 | 1/2009 | Gregory et al. |
| 7,820,872 B2 | 10/2010 | Gregory et al. |
| 7,897,832 B2 | 3/2011 | McAdams et al. |

(Continued)

FOREIGN PATENT DOCUMENTS

| CN | 104013990 A | 9/2014 |
| CN | 107118357 A | 9/2017 |

(Continued)

OTHER PUBLICATIONS

Peng et al., "Factors Contributing to the Failure of Argon Plasma Coagulation Hemostasis in Patients with Nonvariceal Upper Gastrointestinal Tract Bleeding," *Hepato-Gastroenterology* 57:781-786, 2010.

(Continued)

*Primary Examiner* — Mohamed G Gabr
(74) *Attorney, Agent, or Firm* — Seed IP Law Group LLP

(57) ABSTRACT

The present disclosure relates to a gastrointestinal delivery device of a dressing, where the delivery device is capable of fitting through a narrow channel before expanding and applying the dressing. The gastrointestinal delivery device may be used in all gastrointestinal bleeding applications and (Continued)

can be used with a biocompatible, foldable, thin profile, chitosan dressing. Various aspects of the device and its uses are provided herein.

28 Claims, 23 Drawing Sheets

(52) U.S. Cl.
CPC ............... *A61B 2017/00597* (2013.01); *A61B 2017/00623* (2013.01); *A61B 2017/00818* (2013.01); *A61B 2017/00951* (2013.01)

(58) Field of Classification Search
CPC ........... A61B 2017/00575; A61B 2017/00597; A61B 2017/0061; A61B 2017/00623; A61B 2017/00818; A61B 2017/00951; A61B 2090/037; A61F 2002/045; A61F 2013/00931; A61F 2/04; A61L 2400/04
See application file for complete search history.

(56) References Cited

U.S. PATENT DOCUMENTS

| | | | |
|---|---|---|---|
| 8,269,058 | B2 | 9/2012 | McCarthy et al. |
| 8,313,474 | B2 | 11/2012 | Campbell et al. |
| 8,741,335 | B2 | 6/2014 | McCarthy |
| 8,920,514 | B2 | 12/2014 | Gregory et al. |
| 9,004,918 | B2 | 4/2015 | McAdams et al. |
| 9,204,957 | B2 | 12/2015 | Gregory et al. |
| 9,205,170 | B2 | 12/2015 | Lucchesi et al. |
| 10,086,105 | B2 | 10/2018 | Guo et al. |
| 10,315,023 | B2 | 6/2019 | Mantri et al. |
| 2005/0137512 | A1 | 6/2005 | Campbell et al. |
| 2008/0114286 | A1 | 5/2008 | Hamel et al. |
| 2008/0287907 | A1* | 11/2008 | Gregory ............... A61L 15/28 602/49 |
| 2012/0065674 | A1 | 3/2012 | Levy |
| 2012/0296313 | A1 | 11/2012 | Andreacchi et al. |
| 2016/0030625 | A1* | 2/2016 | Mrozek .................. C08J 9/28 521/64 |
| 2020/0306248 | A1 | 10/2020 | Beeley et al. |
| 2021/0052261 | A1 | 2/2021 | Perry et al. |
| 2021/0052766 | A1 | 2/2021 | Gannett et al. |
| 2021/0059867 | A1 | 3/2021 | McCarthy et al. |
| 2021/0059868 | A1 | 3/2021 | Gannett et al. |
| 2021/0060203 | A1 | 3/2021 | McCarthy et al. |

FOREIGN PATENT DOCUMENTS

| | | |
|---|---|---|
| CN | 107375196 A | 11/2017 |
| EP | 2700419 A1 | 2/2014 |
| EP | 3300669 A1 | 4/2018 |
| GB | 2 514 592 A | 12/2014 |
| WO | WO 9736630 A1 | 10/1997 |
| WO | WO 2007139845 A2 | 12/2007 |
| WO | WO 2009111282 A2 | 9/2009 |
| WO | WO 2013180458 A1 | 12/2013 |
| WO | WO 2015175662 A1 | 11/2015 |
| WO | WO 2017161331 A1 | 9/2017 |
| WO | WO 2017214201 A1 | 12/2017 |
| WO | WO 2018204782 A1 | 11/2018 |

OTHER PUBLICATIONS

Adler et al., "ASGE guideline: the role of endoscopy in acute non-variceal upper-GI hemorrhage," *Gastrointestinal Endoscopy* 60(4):497-504, 2004.

Banerjee et al., "The role of endoscopy in the management of patients with peptic ulcer disease," *Gastrointestinal Endoscopy* 71(4):663-668, 2010.

Boonpongmanee et al., "The frequency of peptic ulcer as a cause of upper-GI bleeding is exaggerated," *Gastrointestinal Endoscopy* 59(7):788-794, 2004.

Crooks et al., "Upper gastrointestinal haemorrhage and deprivation: a nationwide cohort study of health inequality in hospital admissions," *Gut* 61(4):514-520, 2012.

Elta et al., "Chapter 8: Approach to the patient with gross gastrointestinal bleeding," *Principles of Clinical Gastroenterology:*122-151, 2008.

Halkerston et al., "PWE-046 Early Clinical Experience of Endoclot™ in the Treatment of Acute Gastro-Intestinal Bleeding," *Gut* 62(Suppl 1):A149, 2013.

HCUP, "Diagnoses—Clinical Classification Software (CCS), Principal Diagnosis: # 153 Gastrointestinal hemorrhage," U.S. Department of Health and Human Services, 2014. (1 page).

Holster et al., "Hemospray in the treatment of upper gastrointestinal hemorrhage in patients on antithrombotic therapy," *Endoscopy* 45:63-66, 2013.

Jairath et al., "Mortality from Acute Upper Gastrointestinal Bleeding in the United Kingdom: Does It Display a "Weekend Effect"?," *Am J Gastroenterol* 106:1621-1628, 2011.

Jairath et al., "Prevalence, management, and outcomes of patients with coagulopathy after acute nonvariceal upper gastrointestinal bleeding in the United Kingdom," *Transfusion* 53:1069-1076, 2013.

Jairath et al., "Why do mortality rates for nonvariceal upper gastrointestinal bleeding differ around the world? A systematic review of cohort studies," *Can J Gastroenterol* 26(8):537-543, 2012.

Karaman et al., "Endoscopic Topical Application of Ankaferd Blood Stopper® in Gastrointestinal Bleeding," *The Journal of Alternative and Complementary Medicine* 18(1):65-68, 2012.

Kheirabadi et al., "Safety Evaluation of New Hemostatic Agents, Smectite Granules, and Kaolin-Coated Gauze in a Vascular Injury Wound Model in Swine," *The Journal of Trauma Injury, Infection and Critical Care* 68(2):269-278, 2010.

Peng et al., "Factors Associated With Failure of Initial Endoscopic Hemoclip Hemostasis for Upper Gastrointestinal Bleeding," *J Clin Gastroenterol* 40(1):25-28, 2006.

Rockey, "Gastrointestinal bleeding," *Gastroenterol Clin North Am* 34:581-588, 2005.

Ryu et al., "Catechol-Functionalized Chitosan/Pluronic Hydrogels for Tissue Adhesives and Hemostatic Materials", *Biomacromolecules* 12:2653-2659, 2011.

Saraf et al., "Mechanical properties of soft human tissues under dynamic loading," *Journal of Biomechanics* 40:1960-1967, 2007.

Sheibani et al., "Natural history of acute upper GI bleeding due to tumours: short-term success and long-term recurrence with or without endoscopic therapy," *Aliment Pharmacol Ther* 38:144-150, 2013.

Sung et al., "Causes of Mortality in Patients With Peptic Ulcer Bleeding: A Prospective Cohort Study of 10,428 Cases," *Am J Gastroenterol* 105:84-89, 2010.

Sung et al., "Early clinical experience of the safety and effectiveness of Hemospray in achieving hemostasis in patients with acute peptic ulcer bleeding," *Endoscopy* 43:291-295, 2011.

Yau et al., "Safety and efficacy of Hemospray® in upper gastrointestinal bleeding," *Can J Gastroenterol Hepatol* 28(2):72-76, 2014.

Ryu et al. "Bio-inspired adhesive catechol-conjugated chitosan for biomedical application: A mini review", *Acta Biomaterial* 27:101-115, 2015.

* cited by examiner

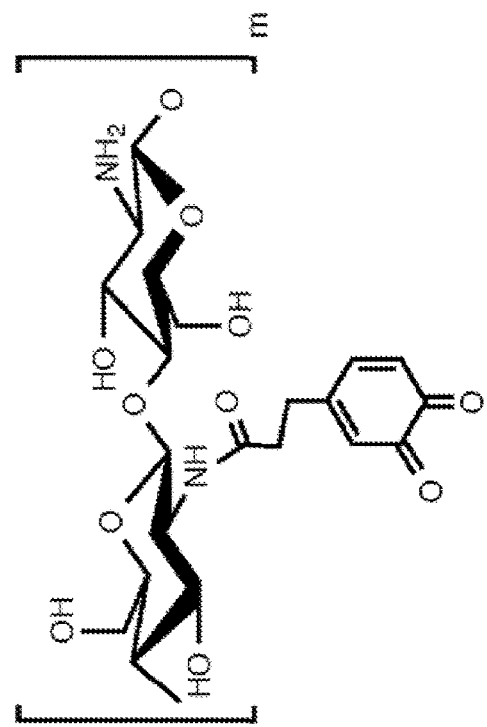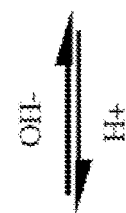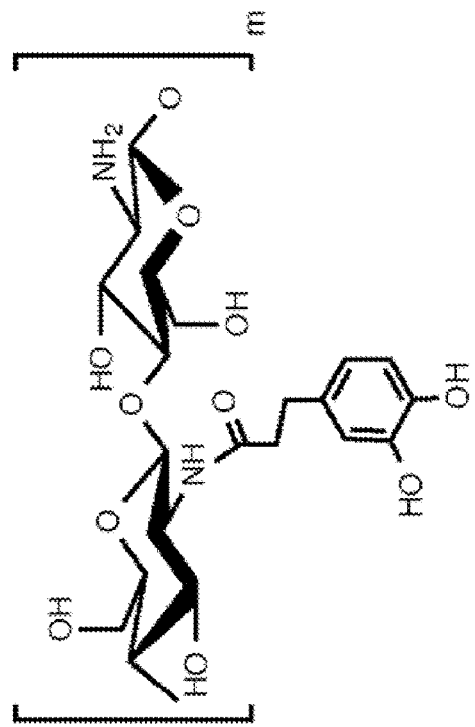
FIG. 3

| Code # | Prototype | Layer | Test tube Test (mins) | Beaker Test (hours) | Fold-ability | In vivo screen #1 | In vivo screen #2 | In vivo screen #3 |
|---|---|---|---|---|---|---|---|---|
| A01 | 2Ch | N | | 0 | Y | | | |
| A02 | 2Ch | N | | 0 | Y | | | |
| A03 | 2Ch | N | | 0 | Y | | | |
| A04 | 4Ch | N | | >8 | Y | | | |
| A05 | 2ChGylcer | N | <15 | | | | | |
| A06 | 2Ch1cell | N | | 0 | Y | | | |
| A07 | 2Ch1Gel | N | | 1 | Y | N | | |
| A08 | 10Gel | N | | | N | | | |
| A09 | 2PAA | N | | 1 | Y | | | |
| A10 | 1PAA | N | | 0 | N | N | | |
| A11 | 2PAA | N | | | N | | | |
| A12 | 0.3PAA | N | | | | | | |
| B01 | 2Ch35DDA1 | N | <15 | | | | | |
| B02 | 2Ch35DDA2 | N | <15 | | | | | |
| B03 | 2Ch40DDA1 | N | <15 | | | | | |
| B04 | 2Ch40DDA2 | N | <15 | | | | | |
| C01 | 5Starch | N | <15 | | | | | |
| C02 | 3Pectin | N | >60 | >7 | N | | | |
| C03 | 3Guar | N | | 24 | N | N | | |
| C03-2 | 3Gu | N | | 0 | N | | | |
| C04 | 3.5Gu | N | | >4 | N | | | |
| C05 | 2Gu1cel | N | | >4 | N | | | |
| C06 | 3Gu0.1Pol | N | | 24 | N | | | |
| C06-2 | 3Gu0.1Pol | N | | 23 | N | Y | | |
| C07 | 3.5Gu0.1Pol | N | | | | | | |

FIG. 6a

| Code # | Prototype | Layer | Test tube Test (mins) | Beaker Test (hours) | Fold-ability | In vivo screen #1 | In vivo screen #2 | In vivo screen #3 |
|---|---|---|---|---|---|---|---|---|
| D01 | 1Ch5Starch1 | N | <15 | 2 | N | | | |
| D02 | 1Ch1Pectin1 | N | <15 | | | | | |
| D03 | 1Ch1Guar1 | N | >60 | 2 | Y | | | |
| D04 | 1Ch5Starch2 | Y | <15 | | Y (cracks) | | | |
| D05 | 1Ch1Pectin2 | Y | <15 | | Y (cracks) | | | |
| D06 | 1Ch1Guar1 | Y | >60 | 0.25/6-17 | Y (cracks) | | | |
| D07 | 4Ch2.5Gu | Y | | 0.25/6-23 | Y (cracks) | | | |
| D08 | 2Ch2.5Gu | Y | | 0.25/3-19 | Y (cracks) | | | |
| D09 | 4Ch2.5Gu | Y | | | Y (cracks) | | | |
| D10 | 2Ch2.5Gu | Y | | | Y (cracks) | | | |
| D11 | 2Ch1Gu | N | | 3 | Y (cracks) | | | |
| D12 | 3Ch0.6Gu | N | | 3 | Y (cracks) | | | |
| D13 | 2Ch1.25Gu | N | | 2 | Y (cracks) | | | |
| D14 | 1Ch1.9Gu | N | | 2 | Y (cracks) | | | |
| D15 | 0.7Ch2.1Gu | N | | 2 | Y (cracks) | | | |
| D16 | 1.5Gu1Cat | N | | 3 | N | | | |
| D17 | 4Ch3Gu | N | | >5 | N | | | |
| D18 | 2Ch2Gu | Y | | 24 | Y (cracks) | N | | |
| D19 | 3Gu4Ch | Y | | 0 | Y | | | |
| D20 | 3Gu0.1Pol4Ch | N | | | Y (cracks) | | | |
| D21 | 0.1PAA2Gu | N | | 31 | N | N, N, N | | |
| D22 | 1PAA3Gu | N | | 48 | N | N | | |
| D23 | 1PAA2Gu | N | | 2-19 | Y | Y, N | Y, Y, Y, Y | N, Y, Y, N |
| D24 | 4Ch0.1Pect | N | | | | | | |

FIG. 6b

| Code # | Prototype | Layer | Test tube Test (mins) | Beaker Test (hours) | Fold-ability | In vivo screen #1 | In vivo screen #2 | In vivo screen #3 |
|---|---|---|---|---|---|---|---|---|
| E1 | ChCatechol | N | | 42 | Y | Y, N, Y, Y | Y, N, N, N | N, N, N, N |
| E2 | ChCatechol | N | | | Y | Y, N | N, N, N, N | N, Y, Y, Y, N, N, N |
| F01 | 2Ch1Cat1Gu | Y | | | Y (cracks) | | | |
| F02 | 1Cat1Gu | N | | | Y | N | | |
| F03 | 1Cat3Gu | N | | >6 | N | N | | |
| F04 | 0.5Cat1Gu0.5Ch | N | | | N | Y | | |
| F05 | 0.5Cat3Gu0.5Ch | N | | >6 | N | N | | |
| F06 | 1Cat1PAA | N | | | N | | | |
| F07 | 1Cat1Gu1PAA | N | | | Y | | | |
| F08 | 1Cat3Gu1PAA | N | | | Y | | | |
| F09 | 1Cat0.25Gu0.25PAA | N | | | Y | | | |
| F10 | 1Cat1Gu0.25PAA | N | | | Y | | | |
| F11 | 0.25Cat1.5Ch | N | | 2 | Y | | N, Y, Y, Y | N, N, Y, Y |
| F12 | 0.75Cat0.5Ch | N | | | N | | Y, N, N, N, N | Y, N, Y, Y |
| F13 | 0.75cat0.5Ch1Gu | N | | | | | | |
| F14 | 0.5Cat1.5Ch | N | | | Y | | N, Y, N, N, Y | |
| G01 | Nanofiber 12GSM | N | | 2 | Y | | Y | Y, Y, Y, Y |
| H01 | PatchPro | NA | | NA | NA | Y | N, N, N, Y, N | N, N, Y |
| H02 | Gauze | NA | | NA | NA | | | |

FIG. 6c

| Code # | Prototype | % Chitosan | Chitosan Lot | % Acetic Acid | %DDA | % Chitosan Catechol | Catechol Approach | %PAA | %Starch | %Pectin | %Guar | Mixture | Layer | Chitin microfiber | Notes 1 |
|---|---|---|---|---|---|---|---|---|---|---|---|---|---|---|---|
| A01 | 2Ch | 2 | A | 2 | 80 | | | | | | | | | | |
| A02 | 2Ch | 2 | B | 1 | 95 | | | | | | | | | | |
| A03 | 2Ch | 2 | B | 2 | 95 | | | | | | | | | | |
| A04 | 4Ch | 4 | B | 2 | 95 | | | | | | | | | | |
| A05 | 2ChGylcer | 2 | A | 2 | 40 | | | | | | | | | | +2% glycerol |
| A06 | 2Ch1cell | 2 | A | 1 | 80 | | | | | | | Yes | | | 1%cellulose |
| A07 | 2Ch1Gel | 2 | A | 1 | 80 | | | | | | | Yes | | | 1% Gelatin |
| A08 | 10Gel | | | | | | | | | | | | | | 10% Gelatin |
| A09 | 2PAA | | | | | | | 2 | | | | | | | |
| A10 | 1PAA | | | | | | | 1 | | | | | | | |
| A11 | 2PAA | | | | | | | 2 | | | | | | | |
| A12 | 0.3PAA | | | | | | | 0.25 | | | | | | | |
| B01 | 2Ch35DDA1 | 2 | A | 2 | 35 | | | | | | | | | | |
| B02 | 2Ch35DDA2 | 2 | A | 2 | 35 | | | | | | | | | | |
| B03 | 2Ch40DDA1 | 2 | A | 2 | 40 | | | | | | | | | Yes | 0.1% chitin |
| B04 | 2Ch40DDA2 | 2 | A | 2 | 40 | | | | | | | | | Yes | 0.1% chitin |
| C01 | 5Starch | | | | | | | | 5 | | | | | | single polymer |
| C02 | 3Pectin | | | | | | | | | 3 | | | | | single polymer |
| C03 | 3Guar | | | | | | | | | | 3 | | | | single polymer |
| C03-2 | 3Gu | | | | | | | | | | 3 | | | | |
| C04 | 3.5Gu | | | | | | | | | | 3.5 | | | | |
| C05 | 2Gu1cel | | | | | | | | | | 2 | Yes | | | 1% cellulose |
| C06 | 3Gu0.1Pol | | | | | | | | | | 3 | Yes | | | 0.1 Polox |
| C06-2 | 3Gu0.1Pol | | | | | | | | | | 3 | Yes | | | 0.1% Polox |
| C07 | 3.5Gu0.1Pol | | | | | | | | | | 3.5 | Yes | | | 0.1% Polox |

FIG. 8a

| Code # | Prototype | % Chitosan | Chitosan Lot | % Acetic Acid | %DDA | % Chitosan Catechol | Catechol Approach | %PAA | %Starch | %Pectin | %Guar | Mixture | Layer | Chitin microfiber | Notes 1 |
|---|---|---|---|---|---|---|---|---|---|---|---|---|---|---|---|
| D01 | 1Ch5Starch1 | 1 | A | 1 | 80 | | | | 5 | | | Yes | | | |
| D02 | 1Ch1Pectin1 | 1 | A | 1 | 80 | | | | | 1 | | Yes | | | |
| D03 | 1Ch1Guar1 | 1 | A | 1 | 80 | | | | | | 1 | Yes | | | |
| D04 | 1Ch5Starch2 | 1 | A | 1 | 80 | | | | 5 | | | | Yes | | |
| D05 | 1Ch1Pectin2 | 2 | A | 2 | 80 | | | | | 1 | | | Yes | | |
| D06 | 1Ch1Guar1 | 2 | A | 2 | 80 | | | | | | 1 | | Yes | | |
| D07 | 4Ch2.5Gu | 4 | B | 2 | 95 | | | | | | 2.5 | | Yes | | |
| D08 | 2Ch2.5Gu | 2 | B | 2 | 95 | | | | | | 2.5 | | Yes | | |
| D09 | 4Ch2.5Gu | 4 | B | 2 | 95 | | | | | | 2.5 | | Yes | | |
| D10 | 2Ch2.5Gu | 2 | B | 2 | 95 | | | | | | 2.5 | | Yes | | 1guar layer |
| D11 | 2Ch1Gu | 2 | B | 2 | 95 | | | | | | 1.25 | Yes | | | |
| D12 | 3Ch0.6Gu | 3 | B | 2 | 95 | | | | | | 0.625 | Yes | | | |
| D13 | 2Ch1.25Gu | 2 | B | 2 | 95 | | | | | | 1.25 | Yes | | | |
| D14 | 1Ch1.9Gu | 1 | B | 2 | 95 | | | | | | 1.875 | Yes | | | |
| D15 | 0.7Ch2.1Gu | 0.68 | B | 2 | 95 | | | | | | 2.075 | Yes | | | |
| D16 | 1.5Gu1Cat | | | | | 1 | 1 | | | | 1.5 | Yes | | | |
| D17 | 4Ch3Gu | 4 | B | 2 | 95 | | | | | | 3 | Yes | | | |
| D18 | 2Ch2Gu | 2 | A | 2 | 80 | | | | | | 2 | Yes | | | |
| D19 | 3Gu4Ch | 4 | B | 2 | 95 | | | | | | 3 | Yes | Yes | | |
| D20 | 3Gu0.1Pol4Ch | 4 | B | 2 | 95 | | | | | | 3 | Yes | | | Gu+0.1% Polox |
| D21 | 0.1PAA2Gu | | | | | | | 0.07 | | | 2.21 | Yes | | | |
| D22 | 1PAA3Gu | | | | | | | 1 | | | 3 | Yes | | | |
| D23 | 1PAA2Gu | | | | | | | 1 | | | 2 | Yes | | | |
| D24 | 4Ch0.1Pect | 4 | B | 2 | 95 | | | | | | | Yes | | | 0.1 Pectin |
| E01 | ChCatechol | | | | | 1 | 2 | | | | | | | | |
| E02 | ChCatechol | | | | | 1 | 3 | | | | | | | | |

FIG. 8b

| Code # | Prototype | % Chitosan | Chitosan Lot | % Acetic Acid | %DDA | % Chitosan Catechol | Catechol Approach | %PAA | %Starch | %Pectin | %Guar | Mixture | Layer | Chitin microfiber | Notes 1 |
|---|---|---|---|---|---|---|---|---|---|---|---|---|---|---|---|
| F01 | 2Ch1Cat1Gu | 2 | B | 2 | 95 | 1 | 3 | | | | 2.5 | | Yes | | |
| F02 | 1Cat1Gu | | | | | 1 | 1 | | | | 1 | Yes | | | |
| F03 | 1Cat3Gu | | | | | 1 | 1 | | | | 3 | Yes | | | |
| F04 | 0.5Cat1Gu0.5Ch | 0.5 | A | 1 | 80 | 0.5 | 1 | | | | 1 | Yes | | | |
| F05 | 0.5Cat3Gu0.5Ch | 0.5 | A | 1 | 80 | 0.5 | 1 | | | | 3 | Yes | | | |
| F06 | 1Cat1PAA | | | | | 1 | 1 | 1 | | | | Yes | | | |
| F07 | 1Cat1Gu1PAA | | | | | 1 | 1 | 1 | | | 1 | Yes | | | |
| F08 | 1Cat3Gu1PAA A | | | | | 1 | 1 | 1 | | | 3 | Yes | | | |
| F09 | 1Cat0.25Gu0.25PAA | | | | | 1 | 1 | 0.25 | | | 0.25 | Yes | | | |
| F10 | 1Cat1Gu0.25PAA | | | | | 1 | 1 | 0.25 | | | 1 | Yes | | | |
| F11 | 0.25Cat1.5Ch | 1.5 | A | 1 | 80 | 0.25 | 2 | | | | | Yes | | | |
| F12 | 0.75Cat0.5Ch | 0.5 | A | 1 | 80 | 0.75 | 1 | | | | | Yes | | | |
| F13 | 0.75cat0.5Ch 1Gu | 0.5 | A | 1 | 80 | 0.75 | 3 | | | | 1 | Yes | | | |
| F14 | 0.5Cat1.5Ch | 1.5 | A | 2 | 80 | 0.5 | 3 | | | | | Yes | | | |
| G01 | Nanofiber 12GSM | | | | | | | | | | | | | | |

*FIG. 8c*

DELIVERY SYSTEMS FOR CONTROL OF GASTROINTESTINAL BLEEDING

GOVERNMENT LICENSE RIGHTS

This invention was made with government support under DK104564 awarded by The National Institutes of Health. The government has certain rights in the invention.

BACKGROUND

Technical Field

This disclosure relates to gastrointestinal medical devices and delivery systems.

Description of the Related Art

Prolonged bleeding, with its associated risks in mortality and morbidity, remains a serious problem in the gastrointestinal (GI) tract. Improved techniques, devices, and dressings that could provide for rapid bleeding control in gastrointestinal bleeding (GIB) for both upper gastrointestinal bleeding (UGIB) and lower gastrointestinal bleeding (LGIB) are needed.

Although there have been advances in bleeding control using advanced dressings for applications outside of GIB bleeding, none of these advances have yet translated to the unique conditions of the gastrointestinal tract and especially the upper gastrointestinal tract where delivery, adhesion, enzyme activity and acidity considerations are highly challenging. Gastrointestinal bleeding (GIB) is a common presentation to the emergency department. According to the U.S. Department of Health & Human Service, from 2000 to 2014, there was an average of over 350,000 discharges from gastrointestinal hemorrhage annually. In the U.S., the direct hospital cost in 2010 due to GIB exceeded $1.1 billion [1]. Upper GIB (UGIB), defined as gastrointestinal bleeding proximal to the ligament of Treitz, is approximately five times more common than lower GIB (LGIB) [2]. Acute UGIB is a potentially life-threatening emergency that necessitates prompt assessment, resuscitation and appropriate medical and endoscopic management. Despite recent advances in management of GIB in western countries, the mortality rate of acute UGIB has not significantly improved, and remains as high as 10-14% [3, 4]. The major cause of death after GIB is death secondary to cardiorespiratory complications, which is not surprising given the burden of comorbidities in such patients; death due to uncontrollable hemorrhage is reported to account for between 20% and 25% of cases [5, 6]. While little can be done to correct comorbidities urgently, more effective and rapid bleeding control will allow significant reductions in the incidence of UGIB related morbidity and mortality. In general, the most common causes of acute UGIB are peptic ulcers, gastroesophageal varices, Mallory-Weiss tears and erosive esophagogastritis [7]. Nonvariceal upper gastrointestinal bleeding (NVUGIB) encompasses all causes of UGIB except bleeding esophageal or gastric varices. The incidence of peptic ulcer disease has decreased because of the development and utilization of proton pump inhibitors as well as the identification, treatment and eradication of *Helicobacter pylori* in individual patients [8]. Despite decreased peptide ulcer incidence, mortality among NVUGIB patients ranges from 3-4% [9]. While rarely life threatening, gastric malignancies can lead to friable tissue with diffuse bleeding that is difficult to address with traditional physical hemostatic methods (clips, bands, ligation) or cautery [10].

Current endoscopic management of patients with acute UGIB includes thermal therapy (e.g., bipolar electrocoagulation, heater probe, monopolar electrocoagulation, argon plasma coagulation, and laser), injection (epinephrine, sclerosants (e.g., absolute ethanol, polidocanol, and ethanolamine), thrombin or fibrin glue (thrombin plus fibrinogen)), and clips [11, 12]. Conventional clips and bands are generally steel or rubber closure systems that require accurate placement and stop or slow bleeding by compressing bleeding blood vessel(s) closed.

In general, the majority of patients with bleeding peptic ulcers, hemostasis is achieved with combination of the above endoscopic therapeutic modalities. However, there remains a subset of patients, approximately 5%, in which endoscopic treatments are not sufficient for hemostasis and thus require interventional radiology or surgical interventions [13, 14].

Endoscopic therapy fails for a variety of reasons including poor visibility of lesion due to active pulsating bleeding, difficult anatomic location of lesion for endoscopy, maximal therapy with currently available tools, and severe coagulopathy.

Only available outside the United States, three different spray-based, hemostatic powder devices, Ankeford Blood Stopper [15], EndoClot™ [16] and HemoSpray™ [17-19] are also being considered to control NVUGIB. A potential concern with Hemospray® is that it is a related product to WoundStat™ which was withdrawn in 2009 in the U.S. due to promotion of diffuse micro-emboli [20] that could cause tissue necrosis and organ failure. Hemospray is generally delivered as an aspirated suspended powder of about 10 g of loose powder into a cavity and takes about 5 minutes after application to achieve satisfactory control (e.g., a purported success rate of about 85%) of Forrest 1a hemorrhage. Although existing tools in the U.S. readily control a significant portion of UGIB, there remains unmet need for the control of brisk arterial bleeding that results in significant mortality and health care expenditure. The devices described herein, for the first time comprise delivery of a hemostatic dressing by, for example, a wire delivery device, for control of GI bleeding, including, particularly, UGIB. The devices described herein, however, represent a substantial improvement in the art for closure of brisk bleeding sites (hemorrhagic), e.g., Forrest 1a bleeding rates at about 25 ml/min or about 20 ml/min, which current technologies do not readily address. Further, the devices described herein may include dressings comprising chitosan that can control hemorrhage in anticoagulated subjects.

BRIEF SUMMARY

The gastrointestinal hemostatic dressing devices described herein are amenable to use in all gastrointestinal bleeding applications and can be used to deliver and apply a dressing to a target tissue site via a narrow channel such as, for example, an endoscopic channel. The devices described herein may be used in minimally invasive procedures. The devices described herein comprise an axis, an expandable support, a dressing and, optionally, a sheath. In some embodiments, a single structure may serve as both the axis and the expandable support. For example, the device may comprise a wire base axis, a balloon catheter expandable support, and a dressing delivered through a standard endoscopic working channel having a diameter of less than or equal to 3.2 mm, or a laser-cut cylinder of nitinol or stainless steel with free ends.

The devices provide for the compact delivery of a splayed high surface area dressing to a target tissue treatment site. In a preferred embodiment, the hemostatic dressing is a chitosan gastrointestinal hemostatic dressing (CGHD). In another preferred embodiment, each dressing weighing, for example, about 0.025 g, when in contact with (or applied directly over) the target tissue site, adheres to the target tissue site in about 30 seconds and may be used to control a Forrest 1a hemorrhage upon serial application of 1 to 3 dressings, i.e., within 30 seconds to 3 minutes.

UGIB bleed rates, or blood flow rates, in ml/min suitable for treatment by the devices described herein may range from about 1 ml/min to about 200 ml/min. In preferred embodiments, the bleeding rates addressed by the devices range from about 1 ml/min to about 150 ml/min. A Forrest 1a UGIB is about 25 ml/min. For subjects suffering a bleed rate of much greater than a Forrest 1a, survival is problematic unless they are already in an operating theater. UGIB bleed rate of between about 20 ml/min and 25 ml/min is considered "brisk" bleeding. Oozing bleeding is generally greater than about 1 ml/min as it is noted that low bleeding rates such as 1 ml/min typically clot and stop of their own accord unless the subject is on anticoagulation therapy or has a disorder of the clotting cascade due to reasons other than taking anticoagulation medication. For such a subject with irreversible anticoagulation medication or with a bleeding disorder, 1 ml/min oozing bleeding remains concerning and needs to be addressed such as by the device of the invention. In some embodiments, the devices described herein are used to address UGIB bleeding rates of between about 1 ml/min and about 25 ml/min, or about 1 ml/min and about 20 ml/min, or about 1 ml/min and about 15 ml/min, or about 1 ml/min and about 10 ml/min, or about 1 ml/min and about 5 ml/min.

The devices disclosed herein provide new treatment approaches involving a dressing material and an opportunity to address or mitigate deficiencies with current modalities, such as clipping, thermal coagulation and injection for treatment of gastrointestinal (GI) bleeding, which necessitate pinpoint accuracy and which are challenging under impaired visibility of brisk, e.g., (Forrest 1a), bleeding conditions.

Further, the devices disclosed herein provide a therapeutic option that promotes or provides hemostasis in a way that allows the body to better heal itself and without inflicting further physical damage to a target tissue site, such as can occur with clipping or thermal coagulation.

In one embodiment, the gastrointestinal delivery devices described herein comprise: an expandable support and a releasable dressing, and the device is capable of fitting through a channel of 4 mm diameter or less. In some embodiments, the device is capable of fitting through one of: a channel of 3.8 mm diameter or less; a channel of 3.5 mm or less; or a channel of 3.2 mm or less. In some embodiments, the releasable dressing attaches to the expandable support. In some embodiments, the device further comprises a sheath that envelopes the expandable support and the dressing. In some embodiments, the sheath constrains an expansion tension from the expandable support. In some embodiments, the expandable support is in an expanded format configuration. In some embodiments, the device further comprises an axis connected to the expandable support. In some embodiments, the expandable support comprises an annular shape in an expanded format configuration. In some embodiments, the expandable support comprises a ribbon spring annular dressing support. In some embodiments, the expandable support comprises more than one wire. In some embodiments, the expandable support comprises a stable balloon in an expanded format configuration. In some embodiments, the expandable support comprises an umbrella style wire frame. In some embodiments, the expandable support comprises at least two articulated spring arms connecting to the releasable dressing. In some embodiments, the expandable support comprises two or more articulated base support spring struts, and the at least two articulated spring arms may connect to both the axis and the base support spring struts. In some embodiments, the axis comprises a wire. In some embodiments, the axis comprises articulated spring arms. In some embodiments, at least one component of the device is selected from the group consisting of: a protective sheath, and an axis formed of ribbon spring wire. In some embodiments, the device further comprises a spring locator positioning arm, wherein the spring locator positioning arm comprises a first end connecting to the axis and a second end connecting to the expandable support. In some embodiments, the axis is also the expandable support. In some embodiments, the releasable dressing is a chitosan dressing attached to the expandable support at a dressing tab, and the one or more dressing tabs are reinforced by at least one of increased dressing density, increased dressing thickness, and/or sewn fibers. In some embodiments, all components of the device other than the releasable dressing consist of wires and, optionally, spring wires. In some embodiments, all components of the device other than the releasable dressing consist of a single wire and, optionally, a spring wire.

In some embodiments, methods of delivering a releasable dressing in vivo to a target tissue site in the gastrointestinal tract using a device described herein, comprises: (a) fitting the expandable support, the releasable dressing, and the axis into a narrow channel of 4 mm diameter or less; (b) expanding the expandable support at a target tissue site; (c) adhering the releasable dressing to the target tissue site; and (d) removing the expandable support and the axis from the target tissue site.

In some embodiments, methods of treating gastrointestinal bleeding using the gastrointestinal delivery device described herein comprises: (a) fitting the expandable support, the releasable dressing, and the axis into a narrow channel of 4 mm diameter or less; (b) expanding the expandable support at a target tissue site; (c) adhering the releasable dressing to the target tissue site; and (d) stopping gastrointestinal bleeding. In some embodiments, the method further comprises applying light pressure on the releasable dressing at the target tissue site. In some embodiments, the light pressure is about 200-300 g. In some embodiments, the light pressure is applied for about 10 to 60 seconds. In some embodiments, the methods further comprise stopping bleeding wherein blood flow rates are between about 1 ml/min to about 150 ml/min. In some embodiments, the methods further comprise providing a releasable dressing in a compact condition, and wherein the releasable dressing comprises chitosan. In some embodiments, the narrow channel is a channel of a gastroscope. In some embodiments, the narrow channel is a delivery port of a gastroscope. In some embodiments, the methods further comprise the step of terminally sterilizing the device, wherein the releasable dressing is terminally sterilized.

BRIEF DESCRIPTION OF THE SEVERAL VIEWS OF THE DRAWINGS

FIG. 3 depicts oxidation of catechol modified chitosan to ortho-quinone modified chitosan under elevated pH and in the presence of oxygen

FIGS. 6A, 6B, and 6C depict a table showing different formulations of dressing, dissolution testing results, foldability testing results & acute in vivo screen results of the different formulations.

FIGS. 8A-8B depict a table showing formulation approaches, hydrophilic polymers, and % w/w of solution hydrophilic polymer components.

FIG. 12a provides schematic drawings of another delivery system for a dressing for controlling gastrointestinal bleeding, including balloon components without the wire components of FIG. 11a.

FIG. 14b provides an end view of the delivery system of FIG. 14a.

FIG. 15b provides an end view of the delivery system of FIG. 15a.

Figure 1:
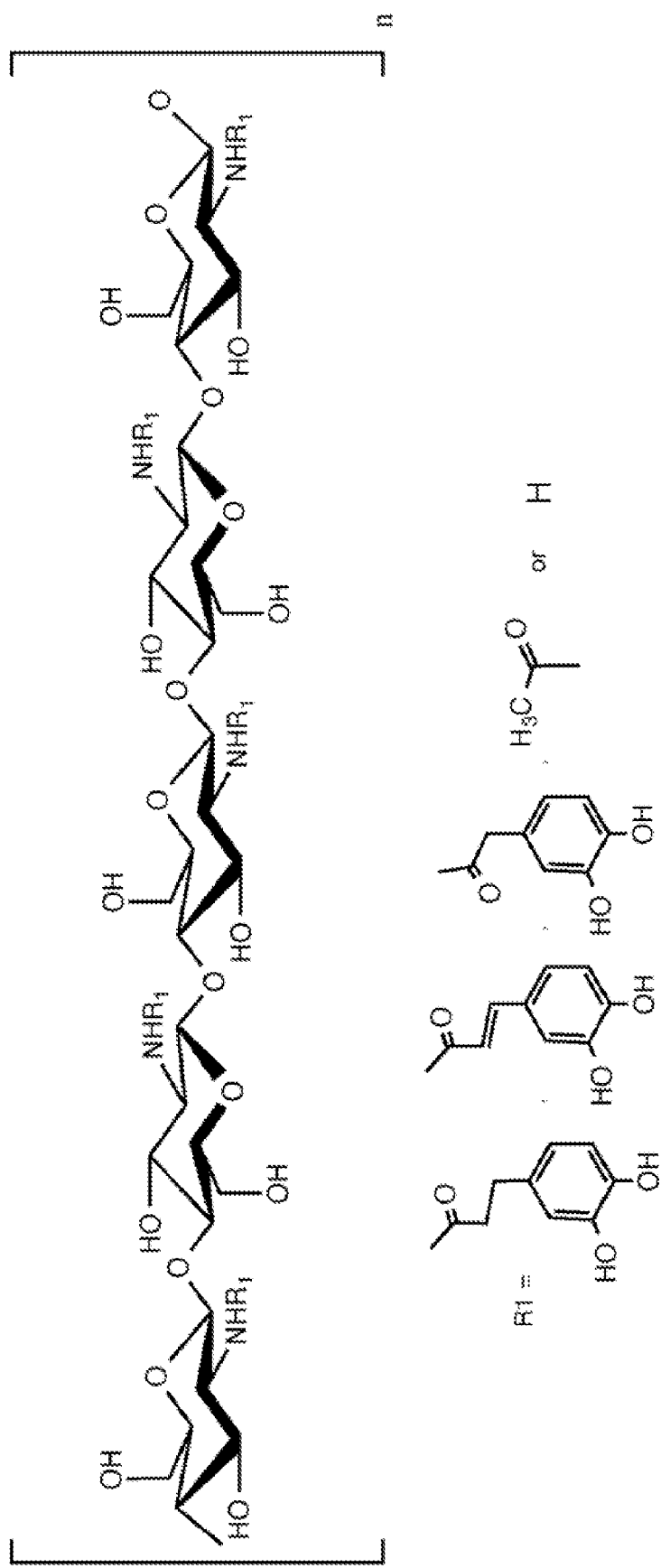
FIG. 1 depicts a chemical structure representation of chitosan (R1=H and acetyl radical) and catechol modified chitosan (R1=H, acetyl, hydrocaffeic acid radical, caffeic acid radical, trans-caffeic acid radical and Homoprotocatechuic acid radical). For chitosan polymer, preferably n>60, more preferably n>300, and most preferably n>600.

Throughout this description it is to be understood that reference identifiers applied in relation to a specific figure feature also relate to like or similar features depicted in other figures regardless of whether such figure features are specifically called out in connection with each figure below.

DETAILED DESCRIPTION

This disclosure generally relates to gastrointestinal hemostatic dressing devices that can be used in all gastrointestinal bleeding applications to deliver and apply a dressing to a target tissue site via a narrow channel such as, for example, an endoscopic channel. The devices described herein comprise an axis, an expandable support, a dressing and, optionally, a sheath. In some embodiments, a single structure may serve as both the axis and the expandable support. The devices provide for the compact delivery of a splayed high surface area dressing to a target tissue treatment site. Suitable dressing materials include, for example, a chitosan gastrointestinal hemostatic dressing (CGHD). The devices described herein are capable of being used alone, i.e., without delivery assisted by passing through a narrow channel. Alternatively, the gastrointestinal delivery device provided herein can be used in combination with other medical devices, including but not limited to, an endoscope, such as an endoscope for gastroscopy. The devices described herein may be suitable for use with non-invasive or minimally-invasive medical procedures. The devices described herein provide a releasable dressing that is left in place at a target tissue site while the remaining device components are removed after the releasable dressing is adhered to a target tissue site.

The devices described herein are capable of being fit through a narrow channel with a dressing before reaching a desired site, or target tissue site, in vivo and delivering the dressing to the target tissue site. The devices described herein include mechanisms to introduce the dressing into the GI environment from the end of a narrow channel. The devices also involve taking the dressing from a compact condition to a splayed condition. In some embodiments, introduction of the dressing into the GI environment from the end of a narrow channel involves introducing the dressing in a compact condition. In alternative embodiments, the introduction of the dressing into the GI environment from the end of a narrow channel involves introducing the dressing in a transition condition or a splayed condition as it emerges from the narrow channel. In some embodiments, the dressing is released from the device after contact with a target tissue site. In some embodiments, the dressing is released upon one or more of expansion of the expandable support into an expanded format and adhesion of the dressing to the target tissue site.

In some embodiments, the dressing seals a target tissue site in gastrointestinal tract. In the case of the GI tract, sealing is complicated by the gel like nature of the mucus of the stomach lining. Attachment to this gel mucus layer is important for efficacy. In some embodiments, the adhered hemostatic dressing promotes bleeding control partly by sealing the wound but also by promotion of local clot formation. For example, mucoadhesive chitosan dressings are highly effective at stopping bleeding by sealing of the target tissue site and by providing local hemostatic promoting capability.

In one embodiment, the dressing provides a unique opportunity for treatment of adherent clots, i.e., by reinforcing and promoting local healing, that could otherwise fail and cause serious hemorrhage if left untreated. Currently there is no treatment for large adherent clots found in the upper GI tract other than keeping subjects under close observation.

In some embodiments, the dressing may further comprise a pharmaceutical active agent (drug or biologic) that may be delivered and applied locally to the target tissue site.

In some embodiments, the dressing stops bleeding at the site in gastrointestinal tract. In one embodiment, the device delivers a CGHD to a target tissue site in the gastrointestinal tract.

A long-felt difficulty and unmet need in the field of delivery hemostatic dressings for treatment of GI bleeding relates to the ability to introduce and apply the dressing at the bleeding site through a non-invasive or minimally-invasive way. The gastrointestinal delivery device of this invention meets this need by providing for a delivery device that can fit through a narrow channel along with a compact dressing and then providing the dressing in a splayed condition for application to a target tissue site. As described herein, the invention comprises a unique expandable support component that provides, in its unexpanded format, for the delivery of the dressing in a compact condition via a narrow channel. The invention also comprises a unique expandable support component that provides, in its expanding format or in its expanded format, for the introduction of a splayed dressing for application to a target tissue dressing site.

In a preferred embodiment, once the splayed dressing is applied to a target tissue dressing site, it is released, and the other delivery components and mechanisms used to deliver the dressing are removed from the target tissue site. The dressing may be releasably attached to one or both of the axis and the expandable support. The expandable support may be collapsed before it is removed from the target tissue site. All device components other than the dressing may then be removed from the target tissue site.

In one preferred embodiment, the gastrointestinal delivery device comprises an expandable support, a wire support axis, and a releasable CGHD dressing, wherein the device is capable of fitting through a channel of 4 mm diameter or less. In some embodiments, the device further comprises a protective sheath.

Definition of Terms

The following terms, including plurals and all tenses thereof, as used in this disclosure have the following meanings.

The term "dressing" means any solid, or semi-solid, or porous, integument, or matrix structure capable of adherence to a target tissue site. Dressings of the present invention comprise dry, compliant, planar porous articles capable of application over a planar target tissue site or capable of compression into non-planar cavity of a target tissue site and may interact uniformly with a surface of the target tissue site.

Dressings of the present invention include, but are not limited to, structures comprising a hydrophilic biopolymer. Preferred dressings of the present invention comprise chitosan or catechol modified chitosan such as, for example, the CGHD described herein.

The term "target tissue site" means a tissue surface that is identified for receipt of a dressing. The target tissue site may or may not include openings, holes, tears, lacerations, damaged or loose injured tissue, or other imperfections that render the tissue surface uneven or incomplete.

The term a "narrow channel" refers to any conduit measuring less than or equal to about 4 mm in diameter. The narrow channel may provide for the safe or controlled passage of the delivery device to a target tissue site.

The term "axis" refers to a structural support of the device. In device embodiments wherein the axis forms a separate component that is distinct from the expandable support and the dressing, it may provide for a point of attachment for either or both of the expandable support and the dressing. The axis may form a core of the device about which the expandable support in its unexpanded format and the dressing in its compact condition may be configured.

The term "expandable support" refers to any structure capable of being transitioned from an unexpanded format into an expanding format and from an expanding format into an expanded format. In some embodiments described herein, expandable supports are also capable of being transitioned from an expanded format into an expanding format and from an expanding format into an unexpanded format. Transition of the expandable support between its various formats (unexpanded, expanding, and expanded) may or may not be automatic or remotely controlled. For example, transition of the expandable support may occur automatically upon removal of a physical barrier or constraint that otherwise suppresses the internal expansion tension of the device, such as when the device exits the narrow channel and/or when a sheath is ruptured. In another example, transition of the expandable support may be controlled remotely by triggering an expansion mechanism that causes the expandable support to go from an unexpanded format towards an expanded format or, alternatively, from an expanded format to an unexpanded format. Expandable supports of the present invention include, but are not limited to, wire structures and balloon catheters. In device embodiments wherein the axis does not form a separate component from the expandable support, reference to the expandable support is meant to include the functional support features of the axis.

The term "sheath" as used herein refers to any cover, membrane, coating, or material used to enclose or envelope, either wholly or partially, one or more of the axis, the expandable support, and the dressing.

The term "wire" refers to a generally elastic to superelastic metallic component with a high aspect ratio (generally >10) of length to width and formed of metals including, for example, nitinol ribbon, round or elliptical gauge wire; stainless steel ribbon round or elliptical gauge wire; longitudinal laser cut nitinol or a stainless steel cylinder.

The term "splayed" means spread out, opened, unfolded, unfurled, uncrimped, or expanded. As used herein, dressings are "splayed" by application of mechanical force, including at the edges or out perimeter of the dressing, that cause its edges to be pulled or pushed apart; thus, splaying the dressing, or changing the configuration of the dressing from a compact condition into a transition condition and/or a splayed condition. It is noted that the dressing described herein are capable of being "un-splayed", i.e., compacted, closed, folded, furled, or crimped. In preferred embodiments, the dressings may be repeatedly splayed and un-splayed.

The term "high surface area" refers to the increased dressing surface area of dressings capable of changing configuration from a compact condition (minimum or near minimum surface area) into a transition condition (larger surface area) and/or a splayed condition (maximum or near maximum surface area). The dressings of the present invention have a splayed configuration that provides a greater surface area relative to any dressing that may be delivered through a narrow channel that is incapable of assuming a transition condition or a splayed condition.

The term "compact condition" refers to the dressing in its closely packed, dense, smallest configuration, which occupies the least amount of space while still being capable of passing through a narrow channel.

The term "splayed condition" refers to the dressing in its spread out, opened, unfolded, unfurled, uncrimped, or expanded. A dressing in its splayed condition is one that has a high surface area and is ready for application to a target tissue site. Dressings of the present invention may be in their splayed condition even if they are not maximally spread out, opened, unfolded, unfurled, uncrimped, or expanded.

The term "transition condition" refers to the dressing that is no longer in its compact condition, but not yet ready for application to a target tissue site.

The term "released" refers to a releasable dressing that is detached, unbound, untethered, or liberated from association with one or both of the axis and the expandable support.

The term "seals" refers to the function of a dressing to fasten or securely close a tissue surface at a target tissue site.

The term "removed" refers to the withdrawal of device components from a target tissue site.

The term "unexpanded format" refers to the expandable support in its closely packed, dense, compact, smallest configuration, which occupies the least amount of space while still being capable of passing through a narrow channel.

The term "expanding format" refers to an expandable support that is no longer in its unexpanded format and increased or enlarged in size, but that is not yet ready to facilitate application of a dressing to a target tissue site.

The term "expanded format" refers to an expandable support that is further increased or enlarged in size relative to the expandable support in its expanding format configuration. The expandable support in its expanded format configuration is ready to facilitate application of a dressing to a target tissue site.

The term "releasably attached" refers to the detachable connection between the dressing and either or both of the axis and the expandable support. Releasable attachment of the present invention may be accomplished, for example, by use of dissolvable threads, weakened and/or perforated connection sites between the dressing and other device component(s), mechanical release or "letting go" of the dressing, etc.

The term "light pressure" refers to the amount of force applied to a dressing upon contact with a target tissue site. For example, light pressure is a pressure at about most preferably 10 kPa or less, more preferably 25 kPa or less, or preferably 50 kPa or less (note 100 g/cm$^2$=9.8 kPa).

The term "contact" means to touch.

The term "adhere" means to hold fast or stick by or as if by gluing, suction, grasping, or fusing to the target tissue site. In one embodiment, dressings comprising chitosan or catechol modified chitosan such as, for example, the CGHD described herein, are held fast and united by molecular forces acting in the area of contact with a target tissue site. After achieving intimate contact with the underlying solid and/or semi-solid tissue and/or mucosal tissue layer by displacement and/or absorption of interfering fluid, the dressing of the invention is united to the said underlying tissue by molecular forces including van der waals (the weakest molecular force but sufficiently strong to provide sealing to hemorrhage at 100 mmHg or 13.3 kPa), electrostatic force between oppositely charge molecules (chitosan is generally positively charge with this positive charge optimized at pH near pH 4.5.—mucosa surface is generally decorated with sialic acid negatively charged species), hydrogen bonding (chitosan has great facility to form hydrogen bonds), and covalent bond (Schiff base or imine functional covalent linkage occurs with chitosan catechol in the presence of tissue groups including an amine, other catechol group covalent reactions can occur with —OH and —SH functional groups at the tissue surface).

The term "rupture" when used to refer to the sheath means to break or burst suddenly, breach, split, separate, or part.

1. Axis

The axis may comprise various materials including, but not limited to, nitinol ribbon, round or elliptical gauge wire, stainless steel ribbon, round or elliptical gauge wire, or a longitudinal laser cut nitinol or stainless steel cylinder. The axis may be a wire or any other structure that functions to deliver the expandable support and dressing and, optionally, the sheath to a target tissue site. In a preferred embodiment, the axis comprises nitinol.

Nickel titanium, also known as nitinol, (a shape memory alloy), is a metal alloy of nickel and titanium, where the two elements are present in roughly equal atomic percentages e.g. Nitinol 55, and Nitinol 60. Nitinol 55 is the most common form of nitinol alloy. Nitinol exhibits shape memory effect and super elasticity. In one embodiment, wire or laser cut cylinder application of nitinol as a device component material relies on the super elasticity effect of nitinol. Superelasticity occurs at a narrow temperature range just above its transformation temperature; in this case, no heating is necessary to cause the undeformed shape to recover, and the material exhibits enormous elasticity, some 10-30 times that of ordinary metal.

In some embodiments, sprung stainless steel round wire or ribbon wire may be used for this elastic recovery device component application. For example, elastic recovery occurs when the sprung material is released from the sheath enclosure and the sprung material returns to its original shape releasing its potential energy as kinetic energy in the process. The kinetic energy is used to splay the dressing.

In some embodiments, a single structure may serve as both the axis and the expandable support. In such embodiments where only an expandable support is referenced, it is to be understood that, in such embodiments, the expandable support serves as both the axis and the expandable support.

The axis serves as an internal support structure for the gastrointestinal device. In some embodiments, the axis comprises one or more wires, e.g. two wires. In some embodiments, the axis comprises one or more spring wires.

In some embodiments, the wire support axis connects to the expandable support either directly or by an intervening structure, e.g., an articulated spring locator positioning arm. The proximal ends of the delivery tube (narrow channel) and delivery wire (axis and/or expandable support), once the device is removed from the packaging are both always outside the proximal end of the endoscope delivery channel. The proximal end of the delivery tube is manually manipulated to position the distal end of the tube in alignment or slightly protruding from the distal end of the endoscope delivery channel. Once the delivery tube is aligned, the tube position is locked inside the endoscope delivery channel so that it cannot progress forward or backward. Once the delivery tube is "locked" in position the proximal end of the delivery wire may be "unlocked" if locked from its positioning inside the delivery tube sheath and forward progression of the delivery wire inside the delivery tube may be accomplished by proximal delivery wire end manipulation.

2. Expandable Support

The expandable support is characterized by an unexpanded format that fits through a narrow channel (e.g. tubing) of 4 mm diameter or less. When in an unexpanded format, the expandable support fits within a dimensional space measuring about 4 mm to 2.8 mm diameter, and/or occupies, as measured by its outermost points, a volume of about 0.38 cm$^3$ to 0.06 cm$^3$. The expandable support is also characterized by an expanded format. When in an expanded format, the expandable support fits within a dimensional cone space of 30 mm to 25 mm height and about 30 mm to 10 mm in diameter, and/or occupies, as measured by its outermost points, a volume of about 7.0 cm$^3$ to 0.65 cm$^3$.

The expandable support may comprise any structure that functions to deliver the dressing and, optionally, the sheath to a target tissue site. The expandable support may comprise various materials including, but not limited to nitinol ribbon, round or elliptical gauge wire; stainless steel ribbon round or elliptical gauge wire; longitudinal laser cut nitinol or stainless steel cylinder, balloons formed of elastomeric integuments such as polyurethane, polyurethane urea, latex rubber, and polybutadiene rubber. In a preferred embodiment, the expandable support is a wire or a balloon.

In one embodiment, the expandable support comprises material formed to have articulated spring ends.

In one embodiment, the expandable support may be repeatedly adjusted between an unexpanded format, expanding format, and expanded format.

The expandable support may attach to the releasably attached dressing.

In one embodiment, the expandable support, upon reaching the desired target tissue site in vivo, can expand from an unexpanded format to an expanded format. When the expandable support is in an expanding format, it may trigger the reconfiguration of the dressing to go from its compact condition, into a transition condition, and then into a splayed condition.

In one embodiment, the expandable support is used to apply a light pressure (e.g. 50 to 400 g) on the dressing, allowing the dressing to contact and adhere to the target tissue site. The expandable support may apply a light pressure to the dressing for a period of time ranging between about ten (10) seconds and five (5) minutes, and more preferably between about twenty (20) seconds and about five (5) minutes. For example, a 20 second to 120 second, or two (2) minute, application time may be suitable for low to moderate bleeding which includes a blood flow rate of about 1 ml/min to about 20 ml/min. Blood flow rates above 20 ml/min may require longer hold application times of about two (2) to five (5) minutes to provide for more secure attachment.

In one embodiment, the deployment and transition of the expandable support from an unexpanded format to an expanding format to an expanded format may take about two (2) to five (5) seconds.

In one embodiment, after contacting and adhering the dressing with the target tissue site, the expandable support releases the dressing, thereby allowing the other (non-dressing) components of the device to be removed and leaving the dressing at the target tissue site. In a further aspect, the expandable support is collapsed into its unexpanded format before being removed from the target tissue site.

In one embodiment, the expandable support is an umbrella structure that can be collapsed and expanded as desired.

In one embodiment, the expandable support may comprise one or more wires. For example, the expandable support comprises an annular shaped wire that can be adjusted between an unexpanded format, an expanding format, and an expanded format at a target tissue site. In some embodiments, the expandable support comprises spring wire structures that form, e.g., a stable balloon, in an expanding format or an expanded format at the target tissue site. In some embodiments, the expandable support comprises multiple substructures, e.g., one or more of a spring wire dressing support loading structure, a base support spring struts, etc.

In some embodiments, the expandable support transitions from an unexpanded format into an expanding format and/or an expanded format, and the device delivers a releasable dressing to a target tissue site. In some embodiments, the expandable support transitions from an unexpanded format into an expanding format and/or an expanded format, and the dressing transitions from a compact condition into a transition condition and/or a splayed condition, and the device delivers a releasable dressing to a target tissue site. In some embodiments, all device components except for the dressing are removed after the dressing is delivered to a target tissue site. In some embodiments, the expandable support in one of an expanding format or an expanded format is collapsed, or returned to an unexpanded format, before all device components except for the dressing is removed.

3. Dressing

The present invention relates to a biocompatible, foldable, thin profile, chitosan-based dressing comprising catechol modified chitosan and characterized by one or more, or all, of the following features, such that it is: (1) able to be delivered intact by balloon or through endoscopic device; (2) is able to wet and adhere intact to gastric mucosa in under 30 seconds with application of light pressure; (3) has capillarity, porosity and absorbency that is able to remove hydrophilic and hydrophobic biological fluids that can interfere with adhesion; (4) is able to stay in place intact and stops moderate to oozing bleeding, e.g., a bleeding rate of between about 20 ml/min to about 100 ml/min, or greater; (5) is able to be released from the delivery device to allow withdrawal of the delivery device from the GI environment; (6) is able to resist detrimental rapid breakdown (<6 hours) in the corrosive enzymes and acidity (≥pH 3) of the GI environment; (7) is able to protect the gastrointestinal injury site for preferably up to 12 hours, more preferably up to 24 hours and most preferably up to 96 hours to assist with its subsequent acute healing and closure; and (8) is able to achieve a controlled, slow dissolution from the attachment site to allow for unassisted complete removal in less than seven days with the dissolved residue passing safely through the alimentary tract.

Chitosan Dressing

Chitosan dressings may refer to compositions that include varying amounts of chitosan. The general contents, general chemical compositions and different forms of a chitosan dressing are described, for example, in U.S. Pat. Nos. 7,820,872, 7,482,503, 7,371,403, 8,313,474, 7,897,832, 9,004,918, 8,920,514, 9,204,957, 8,741,335, 8,269,058, 9,205,170, and 10086105. Such chitosan dressings, due to their chemical and physical properties as described previously, have been used to stop bleeding.

The chitosan used preferably comprises the non-mammalian material poly [.beta.-(1.fwdarw.4)-2-amino-2-deoxy-D-glucopyranose. The chitosan can be processed in conventional ways from chitin obtained, for example, from animal crustacean shells such as shrimp. Chitosan may be biocompatible and biodegradable within the body, and is capable of being broken down into glucosamine, a benign material. The catechol-modified chitosan used herein may include reference to catechol-added chitosan.

A chitosan dressing can be dry or wet. A chitosan dressing is "dry" if the moisture content in the chitosan dressing is less than about 15% by weight, preferably about 10% by weight, and more preferably about 5% by weight. A chitosan dressing is "wet" when the chitosan dressing has come in contact with a source of water, including water in a physiological environments and biological fluids, or in an aqueous solution. For example, a chitosan dressing becomes wet when the chitosan dressing, as described in this disclosure, comes in contact with gastrointestinal tract fluid or a gastrointestinal tract tissue surface (covered by gastrointestinal mucosa). The chitosan dressing, remaining substantially in a solid form absorbs, displaces, redirects or channels water/moisture in the physiological environment of gastrointestinal tract in amounts sufficient to permit adhesion of the chitosan dressing to the tissue surface. The adhered chitosan dressing can be used to seal wound surfaces and slow or stop further bleeding.

In a preferred embodiment, the chitosan gastrointestinal hemostatic dressing of the invention contains preferably greater than or equal to 25% by weight chitosan; more preferably greater than or equal to 50% by weight chitosan and most preferably greater than or equal to 75% by weight chitosan. Chitosan is a generic term used to describe linear polysaccharides that are composed of glucosamine and N-acetyl glucosamine residues joined by β-(1-4) glycosidic linkages (typically the number of glucosamines≥N-acetyl glucosamines) and whose composition is soluble in dilute aqueous acid (Roberts 1991). The chitosan family encompasses poly-β-(1-4)-N-acetyl-glucosamine and poly-β-(1-4)-N-glucosamine with the acetyl residue fraction and its motif decoration (either random or block) affecting chitosan chemistry. The C-2 amino group on the glucosamine ring in chitosan allows for protonation, and hence solubilization of chitosan in water (pKa≈6.5) (Roberts 1991). Other hydrophilic polymers such as, for example, guar, pectin, starch and polyacrylic acid may be used.

In a preferred embodiment, the dressing of the invention is polymeric, thin (preferably dry dressing thickness of about ≤500 microns, more preferably thickness of about ≤200 microns, most preferably thickness of about ≤100 microns), flexible, porous, dry, biocompatible, tissue adherent and hemostatic.

The dressings are not limited in shape, however square, rectangular, circular, or circular petal shaped dressings are preferred. In one embodiment, a maximum size could be up to about 50 mm×50 mm square or 50 mm in diameter. In another embodiment, dressing size could be about 45 mm×45 mm square or 45 mm in diameter, 40 mm×40 mm square or 40 mm in diameter, 35 mm×35 mm square or 35 mm in diameter, 30 mm×30 mm square or 30 mm in diameter, 25 mm×25 mm square or 25 mm in diameter, 15 mm×15 mm square or 15 mm in diameter, 10 mm×10 mm square or 10 mm in diameter, etc. In still another embodiment, each of the length and width may range from about 10 mm to about 50 mm, or from about 10 mm to about 50 mm in diameter. As dressings become larger in size they become increasingly subject to delivery limitations in confined cavities such as the stomach, etc.

Dressings described herein may provide a large dressing surface area in an open, unfurled, or unfolded condition. Alternatively, dressings described herein may provide a small dressing surface are in a closed, furled, or folded condition. The ability of the dressings to be folded, furled, or closed allows them to be more compact and protected for delivery and reduces the likelihood that the dressing surface is prematurely wetted prior to delivery to a target tissue treatment site.

In a preferred embodiment, the dressing is about 50 microns thick, is about 2.5 cm in diameter, and will have an open, unfurled, or unfolded outward facing surface area of about 9.856 $cm^2$. Inside the delivery device sheath (wall thickness of a typical fluorinated ethylene propylene (FEP) delivery tube is about 150 microns), a closed, furled, or folded dressing will have an outward-facing cylindrical surface area (in a 1.25 cm long cylinder) of about 2.07 $cm^2$ inside a 0.45 cm diameter gastroscope channel, or about 1.56 $cm^2$ inside a 0.32 cm diameter gastroscope channel; or about 1.41 $cm^2$ inside a 0.28 cm diameter gastroscope channel. Thus, in one example, a dressing of the present invention may, in an open, unfurled, or unfolded condition, have an outward facing surface area that is about six (6) times greater, about five (5) times greater, or about four (4) times greater than the outward facing surface area of that same dressing when it is in a closed, furled, or folded condition. In some embodiments, the ratio of the outward facing surface area of an open, unfurled, or unfolded to a closed, furled, or folded dressing is about 15:1, or about 14:1, or about 13:1, or about 12:1, or about 11:1, or about 10:1, or about 9:1, or about 8:1, or about 7:1, or about 6:1, or about 5:1, or about 4:1, or about 3:1, or about 2:1.

It is noted that the most common gastroscope channel is 0.28 cm diameter (2.8 mm) and hence this is the most preferred size for the dressing delivery. Alternatively, a more preferred size is 0.32 cm diameter, which is a standard gastroscope channel diameter but less common than the 0.28 cm channel. Another preferred gastroscope channel diameter size is between 0.45 cm and 0.32 cm which is more a custom gastroscope channel size and, thus, less common than the 0.32 or the 0.28 cm gastroscope channel diameter size.

It is able to be folded and unfolded, is not readily soluble in blood or body fluid at about 37° C. within, preferably, the first 6 hours of application, more preferably the first 12 hours of application, and most preferably the first 24 hours of application, and degrades and/or dissolves fully in contact with gastrointestinal fluids at about 37° C. within about 7 days.

It will not adhere to the delivery device, and does not swell or shrink appreciably, i.e., it does not increase or decrease in size by more than about 25% in length and width, or more than about 50% in thickness, in the presence of blood and GI fluid at about 37° C.

In a preferred embodiment, the dressing may be terminally sterilized without affecting dressing characteristics. When it is stored under controlled conditions in its packaging at room temperature of about 21° C. to about 25° C., its tissue adhesion properties, mechanical properties, dissolution properties in gastrointestinal fluid, swelling properties, and hemostatic properties are stable and do not change appreciably over time (e.g., about ≤2 years).

A preferred embodiment, the dressing has a tissue adhesive side and a non-adhesive side. In this embodiment, the non-adhesive side may provide a surface that when wet readily slides away from itself and from any applicator or delivery device surface that is applying pressure against the dressing inside a lumen, and/or in the gastrointestinal tract.

A preferred embodiment of the dressing is that it is formed of a substantially dry chitosan composition with a water content of about <15%, or about <8%. The dry chitosan composition is preferably formed using phase separation and drying of an aqueous solution of chitosan and water. The dry chitosan dressing is preferably prepared in sheet form which may be cut to size.

Preferred embodiments of the biocompatible, bio-dissolvable, tissue adherent chitosan dressing are able to resist dissolution in gastrointestinal (GI) fluid and blood at about 37° C. for at least about 6 hours is tissue adherent and includes materials and material structures that promote resistance to rapid dissolution and degradation in the low pH and strongly enzymatic digestive fluid of the upper gastrointestinal tract. This is a significant advantage of the chitosan dressings disclosed herein because the upper gastrointestinal digestive tract has evolved to rapidly digest most organic materials including chitosan, cellulose and starch.

Chitosan dressings provided herein can be applied to a mucus surface, e.g., in gastrointestinal tract by light pressure. Light pressure applied to the dressing on a tissue surface as used herein indicates a pressure that attaches and keeps a chitosan dressing in contact with an injury site without significant deflection or movement of the tissue so as to allow the chitosan dressing, through its compositional structures and characteristics, to interact to promote adherence with the injury site to stop bleeding. In some embodiments, a light pressure is a pressure at about most preferably 10 kPa or less, more preferably 25 kPa or less, or preferably 50 kPa or less (note 100 g/cm2=9.8 kPa). Typically there is significant deflection on application of load above 100 kPa to soft tissue such as the stomach making application of pressure without a supportive opposite pressure impossible. An exploration of the elastic modulus of the human stomach is provided in Saraf et al. 2007. Saraf, H. et al., *Mechanical properties of soft human tissues under dynamic loading*, J. OF BIOMECHANICS, 40(9), pp. 1960-1967 (2007).

Production of Chitosan Dressing

The chitosan dressings of the present invention may be generated using various methods and processes. In some embodiments, the chitosan dressing may be formed by freeze phase separation and drying. In an alternate embodiment, the dressing is formed by addition of a foaming agent to provide a low density foam before freezing followed by drying. Freeze phase separation followed by removal of frozen solvent by sublimation is called freeze drying. Freeze phase separation is a process of solidification from dilute solution whereby removal of heat and resultant lowering of temperature through a container or mold surface holding the dilute solution results in a localized solid crystal nucleation of pure solvent and subsequent propagation and growth of pure solvent crystal. A result of the pure solvent crystal growth in a dilute solution is that solute diffuses away from the growing crystal front to solidify at the interstices between the growing crystal. Freeze phase separation of dilute polymer aqueous solutions results in alternate layers of thin polymer lamella between thicker layers of ice. Removal of the ice by methods which do not disrupt the polymer lamella results in a low-density polymer dressing with inter-connected porous structure. For example, in one embodiment, low-density polymer dressings may have an initial dressing density from about 0.005 g/cm$^3$ to about 0.05 g/cm$^3$.

In an alternate embodiment, the freeze phase separated dressing is formed by freezing of a foamed dilute solution followed by drying. In an alternate embodiment, the dressing is formed by non-woven fiber spinning processes, such as centrifugal spinning, electrospinning or solvent fiber extrusion into a coagulation bath. In yet another alternate embodiment, the dry dressing of the invention may be formed from a woven fiber process. In yet another alternate embodiment, the dry dressing of the invention may be formed by phase inversion and precipitation with a non-solvent (as is typically used to produce dialysis and filter membranes). In still another alternate embodiment, the dressing of the invention may be formed from an additive 3D printing process.

In a preferred embodiment of the invention, the dressing preparation process may include a compression process that changes the initial dressing density from an initial preferred range of about 0.005 g/cm$^3$ to about 0.05 g/cm$^3$ to a final preferred range of about 0.03 g/cm$^3$ to about 0.7 g/cm$^3$; however, ranges of about 0.08 g/cm$^3$ to about 1.2 g/cm$^3$ are also contemplated. It is noted that a density of about 1.5 g/cm3 is the density of void-free chitosan dressings. The compression process may include application of temperature in the range of about 20° C. to about 150° C. To avoid substantial dressing swelling of the dry compressed dressing on contact with biological fluid, the temperature of the compression is preferably applied by a method that may include but not be limited to convection, conduction and radiation, and the temperature of the compressed dressing should preferably be maintained at least about 80° C. for at least about 15 seconds.

Heat during compression is a tool that allows plasticization and molding of the chitosan without cracking or tearing of the chitosan (non-destructive molding). The first glass transition temperature (Tg) of pure dry chitosan is near 80° C. which if processed near in the case of pure dry chitosan will allow ready non-destructive molding of the chitosan as well as some crystalline annealing of its structure. It is possible to lower the Tg by application of plasticizers such as water or glycerol to the chitosan and hence provide a similar level of non-destructive molding at lower temperature. Here, it is noted that chitosan can be molded non-destructively in the range 20° C. to 150° C. Outside of this range it would still be possible to non-destructively mold the chitosan but much more difficult. Above 150° C. the chitosan begins to thermally degrade while below 20° C., the addition of plasticizers may lead to undesirable loss of chitosan crystallinity which provides for dissolution resistance and resistance to degradative processes such as occur in sterilization.

Preferably, the compression prevents substantial swelling of the dry compressed dressing on contact with biological fluid and is performed with moisture content of the dry dressing during the compression at about <15% w/w. The compression may be applied through twin or multi-roller compression and/or uniaxially between adjacent platens.

The compression may be against a uniform flat or curved surface to provide a smooth finish to the compressed dressing.

Alternatively, the compression may be applied against an etched, machined, ablated or other type of surface treatment that imparts a depleted or added surface texture. The surface texture may be a random or it may be a regular repeated pattern. The pattern of the surface may assist in folding and unfolding or furling and unfurling the dressing and may provide for hinge-like properties in the dressing. Such texture may be used as an adjunct to quickly lock the dressing in place and stop it moving when applied. Movement of the surface of the dressing while positioned against the target tissue surface can cause filming and hence closure of the open surface structure which can lead to loss ability to remove anti-adhesive biological fluid at the surface and hence loss of ability to adhere the dressing to the surface. The timescale of the changes occurring at the dressing surface is very important such that surface uptake of fluid with significant surface dressing channel closure is highly undesirable. A good way to avoid such movement is to physically fix the dressing in place as soon as it contacts the tissue surface.

Prior to the present invention, thin solid chitosan dressings were generally rigid, not flexible enough to be bent or folded or furled without breaking, fracturing, or otherwise losing their intact shape or becoming otherwise unsuitable for use. Chitosan dressings provided herein, due to their compositional structures and characteristics, can be folded and unfolded along a folding axis while still being intact and suitable for use in stopping bleeding. Interestingly, and contrary to expectation, it has been found that chitosan dressings described herein, when folded, become less resistant to tearing or breakage along their folded seams. In some embodiments, the chitosan dressing provided herein, due to its compositional structures and characteristics, can be furled without losing its compositional structures and characteristics and still being intact and able to stop bleeding. In some embodiments, the chitosan dressing provided herein, therefore, is able to be delivered through a narrow working channel while still maintaining their compositional structures and characteristics intact. Exemplary diameters of a narrow working channel through which the chitosan dressing provided herein can be delivered include a diameter of about 3.2 mm or less, and including, but not limited to, 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, and 3.2 mm.

Catechol Modified Chitosan; and its Production

The chitosan dressings described herein relate to chitosan dressings comprising catechol modified chitosan and/or hydrophilic polymers. Other aspects of chitosan dressing comprising catechol modified chitosan are described in more details below.

Preferred embodiments of the chitosan gastrointestinal dressing of the invention include compositions with catechol modified chitosan and/or, optionally, other hydrophilic polymers. Preferably the catechol modified chitosan in the dressing provides prolonged adherence to wetted tissue with tissue adherence ≥about 1 kPa resisting dissolution in water, saline solution, blood and/or GI fluid at about 37° C. for ≥about 6 hours. Preferably the catechol modified chitosan is formed by N-acylation of the C-2 amine on the chitosan glucosamine by 3,4-dihydroxyhydrocinnamic acid (alternatively named 3-(3,4-Dihydroxyphenyl)propionic acid, Hydrocaffeic acid)). Alternatively, the chitosan N-acylation to produce a catechol modified chitosan may include but not be limited to a modification with one of a 3,4-Dihydroxycinnamic acid (caffeic acid); a trans-3,4-Dihydroxycinnamic acid (trans-caffeic acid); and a 3,4-Dihydroxyphenylacetic acid (DOPAC, Homoprotocatechuic acid).

The presence of catechol in the composition provides for some poly-conjugated structure as the catechol is oxidized to o-quinone. This causes visible difference between the unmodified chitosan and catechol modified chitosan compositions, which may be off-white or pink to dark brown in color, respectively. It is noted that the catechol modified chitosan compositions go from pink to brown when oxidation occurs in the catechol.

Pink coloration in the catechol modified chitosan, signifying substantial absence of crosslinking, is provided in the aqueous synthesis by maintaining pH reaction solution at or below pH 5.5. The pink coloration may also be provided in the aqueous synthesis by performing the modification and subsequent processing steps substantially in the absence of oxygen such as by using aqueous systems purged with an inert gas which may include but not be limited to argon or nitrogen. Although the pink coloration is not desirable in the final solution or catechol modified product, it may be desirable in intermediate handling stages (such as immediately after chitosan derivatization with catechol and/or dialysis and/or washing of the subsequent catechol chitosan solution to remove residual unreacted material) because it allows for stable dry product polymer storage and dry product weight determination with subsequent ability to substantially re-dissolve the pure dry catechol modified product in water to a desired dry weight at a later time. This water-soluble chitosan catechol material is then subsequently oxidized and crosslinked (with brown coloration). However catechol modified chitosan which is dried before oxidation is not suitable for use in the chitosan dressing of the invention because dressings including such treated catechol modified chitosan are not readily redissolved and the final solution includes an undesirable mass fraction (>5% w/w) of insoluble particulate (>10 microns in diameter).

Additionally catechol chitosan prepared after an intermediate freeze drying stage is more prone to early dissolution in gastrointestinal fluid.

In a preferred embodiment, the catechol modified chitosan is not removed from solution by an intermediate drying step to allow for storage but rather it is kept in aqueous solution and oxidized in aqueous solution by exposure to higher than about pH 5.5 in the presence of atmospheric oxygen. Preferred pH control is achieved by adjustment of partial pressure of aqueous dissolved carbon dioxide (increased partial pressure reduces pH while decreased partial pressure increases pH to nearer pH 7). An alternative preferred means of pH control is by incremental addition of a strong acid to lower pH and a strong base to raise pH. Examples of strong acids may include, but are not limited to, hydrochloric acid, sulphuric acid and nitric acid. Examples of strong bases may include but not be limited to sodium hydroxide and potassium hydroxide. Subsequent drying of this aqueous water-soluble oxidized catechol modified chitosan results in a preferred level of crosslinking of the catechol chitosan with good resistance to dissolution and degradation in the upper gastrointestinal tract. The catechol chitosan solution may be diluted by addition of water or concentrated by water removal. The water may be removed by the techniques including, but not limited to, ultrafiltration, reverse dialysis and centrifugation. The solid fraction of the solution may be determined by sampling a known volume from the solution and performing analyses including but not limited to gravimetry, Fourier transform infrared spectroscopy, ultraviolet-visible spectroscopy, refractometry, and pycnometry.

Figure 5:
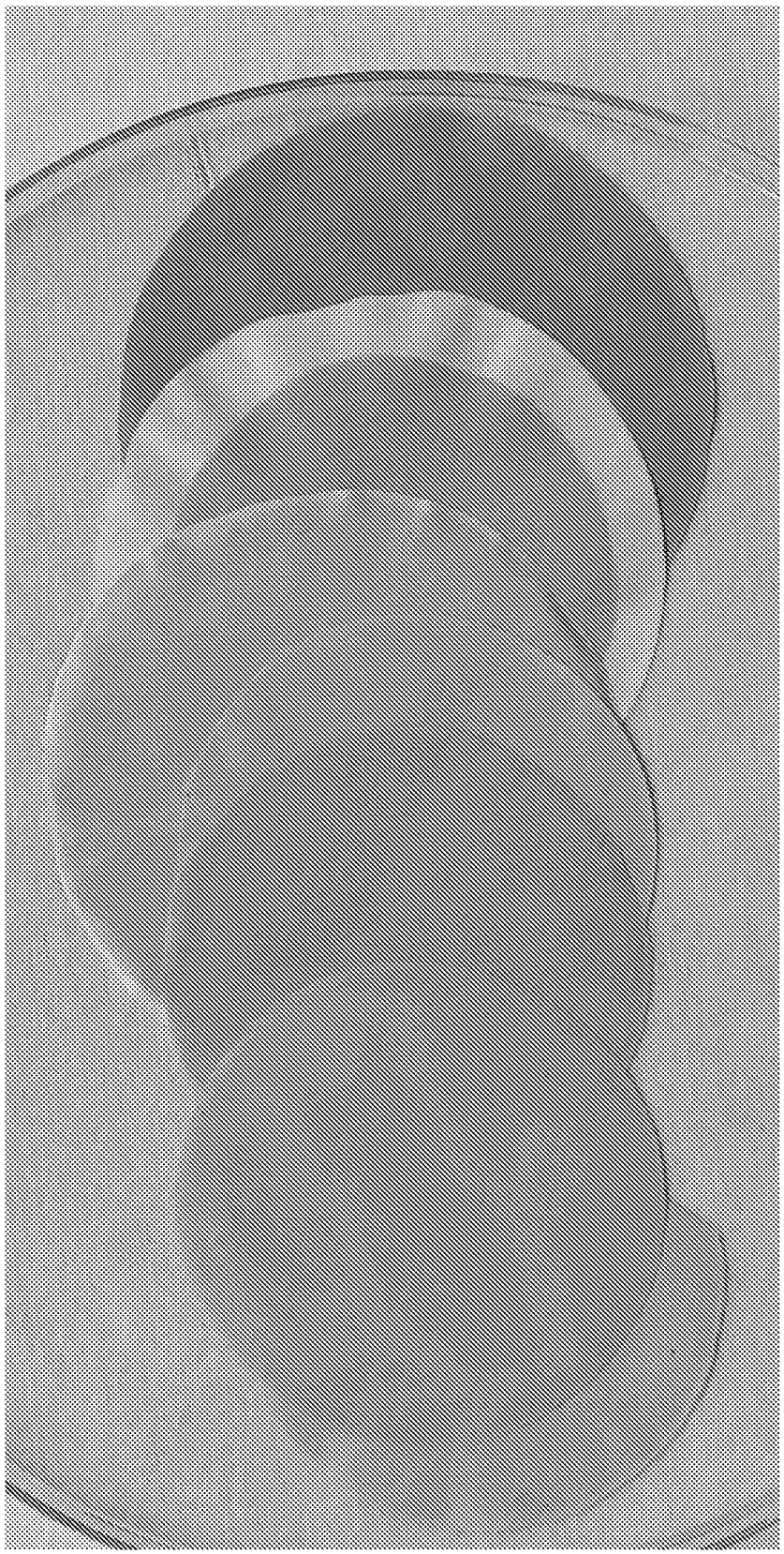
FIG. 5 depicts round-shaped catechol modified chitosan dressing that are (pre-cut) 2.5 inch & 2 inch diameter compressed to near 50 microns. The coloration of these catechol modified chitosan dressing, starting from left to right, ranges from light pinkish brown (first dressing), 2 dressings of darker pinkish brown, 2 tan brown colored dressings (no pink), 1 brown dressing and lastly 1 darker brown. Catechol chitosan dressings 5 & 6 are formed from 2.5" and 2" molds and they are backed with unmodified chitosan dressings both from 2.5" molds and the unmodified chitosan can be seen clearly as the white halo (no brown or pink color) in dressing 6. The catechol chitosan and unmodified chitosan dressings were adhered together during compression to a final shared density >0.4 g/cm3. The pink coloration is associated with unoxidized catechol while the brown color is associated with the oxidized catechol (o-quinone). The lighter browns and lighter pinks are associated with lower degree of substitution of the chitosan with catechol (nearer 10%) while the darker colorations (pinkish brown & brown) are associated with higher degree of substitution of the chitosan with catechol (nearer to 20%).

In a preferred embodiment, the catechol modified chitosan composition is of a brown color resulting from catechol oxidation to o-quinone. The quinone is produced by autoxidation of the catechol hydroxyls in the presence of oxygen and at pH above about 5.5. Schiff base reaction of quinone with chitosan C-2 amine produces crosslinking in the modified chitosan. The color of the catechol modified chitosan composition is controlled during synthesis by controlling pH and oxygen exposure. Maintenance of pH at or below about pH 5.5 inhibits the production of o-quinones. Subsequent conditioning of dialysis solution, final washed, or dialysed catechol chitosan solutions in a preferred pH range 5.8 to 6.2 provides for more dissolution resistant, darker, more oxidized catechol. In some embodiments, the coloration of catechol modified chitosan characterizes one aspect of the catechol modified chitosan dressing. In some embodiments, the coloration reflects the degree of substitution of the chitosan with catechol. In some embodiments, the coloration from pink to brown correlates with the degree of substitution. FIG. 5 shows exemplary embodiments of different colorations reflecting and correlating with different degree of substitution of the chitosan with catechol.

In order to prepare a dry dressing from the catechol chitosan, a preferred light brown to darker brown catechol aqueous chitosan solution is prepared which may be used by itself or may be mixed with other aqueous hydrophilic polymer solutions including but not limited to solutions of chitosan and/or, optionally, hydrophilic polymers. Preferably, the dry phase separated catechol chitosan dressings are prepared as densified dried freeze-phase-separated and fibrous dressing structures.

Preferred crosslinked catechol modified chitosan compositions of the invention provide good tissue adherence and 10 times to 100 times increased resistance to dissolution in the upper gastrointestinal tract compared to dressings formed substantially of unmodified chitosan. For example, FIGS. 6A-6C show dissolution testing results demonstrating that chitosan dressings are gone in 15 minutes while some catechol dressings lasted greater than 24 hours. The catechol modified chitosan compositions described herein, provide hitherto unknown longevity, biocompatibility, and ability to eventually dissolve.

Preferred rapid adherence to gastrointestinal mucosa of the chitosan gastrointestinal dressings of the invention (≤1 minute) is provided in the dry chitosan dressing by the promotion of quaternary ammonium cation formation at the chitosan glucosamine C-2 amine by the presence of an acid in the dry dressing composition. Preferred chitosan acid salts in the dressing may include salts of acetic, lactic, glycolic, citric, succinic, malic, hydrochloric, glutamic, ascorbic, malonic, glutaric, adipic, pimelic, and tartaric acids, and combinations thereof. Preferably the acid salt % weight of the chitosan is greater than about 2% and less than about 15%. To achieve fast adherence (e.g., ≤1 minute) to wet tissue, the moisture in the dry gastrointestinal dressing is preferably less than about 15% by weight; more preferably it is less than about 10% by weight and most preferably it is less than about 5% by weight. In the case of densified freeze-phase-separated and dried chitosan dressings, the chitosan solution is poured into the freeze-phase-separation mold (typically in the shape of a pan with a horizontal flat base) with preferably around a 0.1% w/w, more preferably around 0.5% w/w and most preferably 0.25% w/w hydrophilic polymer chitosan solution. The hydrophilic polymer solution is preferably added to the horizontal flat pan to a vertical depth of preferably about 10 mm, more preferably 2.5 mm and most preferably 5.0 mm mold depth. The solution in the mold is subsequently frozen and dried to remove water by sublimation or freeze phase substitution (solvent extraction of the ice with a non-solvent to the polymer) to a low density (>99% void volume) open or porous dry sponge with a dry density <about 0.01 g/cm$^3$ (or, for example, about 0.005 g/cm$^3$ for a catechol chitosan uncompressed dressing from 0.5% solution, which is about ⅕ or 20% of the density of an uncompressed HemCon Bandage chitosan sponge, which is about 0.025 g/cm$^3$). Lyophilization is typically performed at pressure below 300 mTorr while freeze substitution involving a dry, cold (e.g., <−20° C.) solvent such as ethanol is performed at atmospheric pressure. The dry sponges are then compressed, preferably to greater than about 0.4 g/cm$^3$ density and less than about 100 microns thickness. The preferred compression is not limited to but may include uni-axial compression between aligned flat platens, wherein the platens are heated between 18° C. and 150° C. and are pressure loading up to 10,000 bar.

The preferred compression creates a remarkably thin (e.g., range from about <50 microns to about <200 microns) strong (e.g., 5 MPa to 25 MPa UTS) readily foldable chitosan dressing that may be placed minimally invasively anywhere in the body in a confined folded form that can be reformed without compromised performance to the original unfolded dressing form for accurate and effective high surface area placement and attachment.

Figure 7:
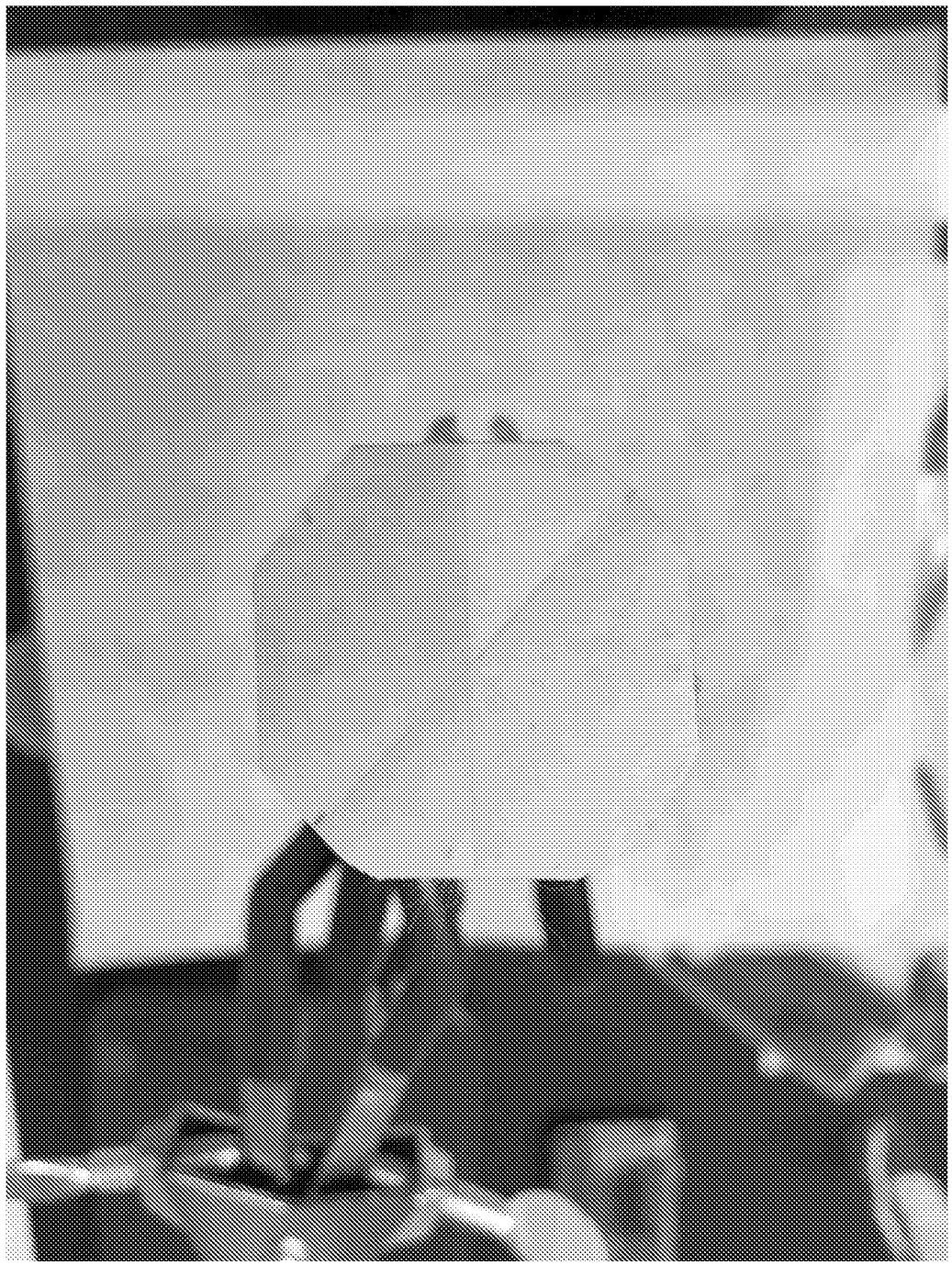
FIG. 7 depicts a catechol modified chitosan dressing that has been folded and unfolded, remaining intact with visible fold axis (crease).
Figure 9:
FIG. 9 depicts a gastroscope digital image of the modified catechol chitosan dressing of the invention intimately adhered to stomach mucosa, demonstrating slight swelling in the stomach environment, and effectively controlling upper gastrointestinal hemorrhage (Forrest 1a) of a lacerated gastroepiploic artery inside the stomach of a heparinized (ACT≥250 s) swine 3 hours after application of the dressing to the arterial injury.
Figure 10:
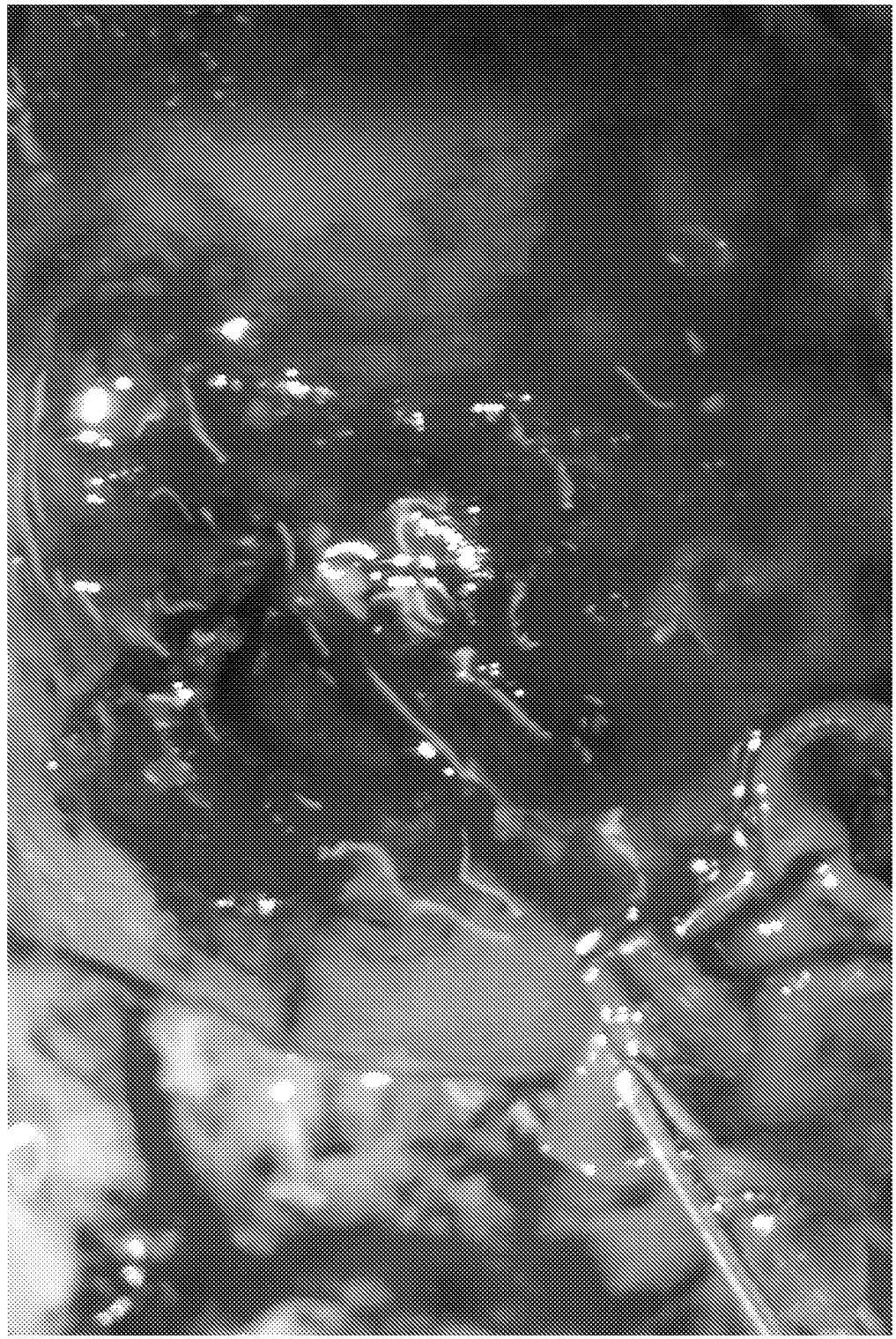
FIG. 10 demonstrates the presence of a strong intact clot under the dressing of FIG. 9 at animal sacrifice which was within 45 minutes of taking the image of FIG. 9. The modified chitosan dressing was shown to be uniformly adhered to the injury and stomach mucosa at sacrifice.

Foldability is addressed in the examples below. In one embodiment, fold testing involved folding the horizontally planar final compressed circular dressing through 180° edge over edge, first in an anticlockwise direction, holding the edges together and compressing firmly in the middle of the dressing to create a single linear fold axis (or crease) in the dressing. The folded dressing is then opened and the edge to edge fold is reproduced in the new fold axis but with the folding in the opposite clockwise direction. Foldability success can be rated as no tears or cracks being visible along the fold axis and no significant loss in tensile properties of the dressing (determined by gentle pulling across the fold of the dressing). FIG. 7 shows a catechol modified chitosan dressing that has been folded and unfolded, remaining intact, with visible fold axis (crease).

Freeze phase separation of dilute aqueous polymeric solutions results in phase separation of micron and submicron thin polymeric chitosan lamella interspersed regularly between ice crystal sheets close to 200 microns in width. Removal of the ice by sublimation (freeze drying) or alternatively by solvent extraction leaves the dry sponge composed of close-to-aligned, thin (≤1 micron), polymeric chitosan lamella. Compression of the polymeric chitosan lamella at close to or greater than their glass transition temperature (Tg for dry chitosan is near 80° C.) allows for their compression into the thin (near 50 microns) dense polymeric structure formed of layers of hundreds of strong compliant polymeric chitosan leaves (lamella) which do not readily propagate cracks and which can be folded repeatably without failure. Such multi-leaf layering achieves remarkable strength. Prior to the present invention, no one has previously investigated high-density freeze-phase-separated chitosan dressings for manufacture and use as described herein and with the aim to address key problems solved by the present invention such as, for example, adhesion by removal of interfering fluids (by absorption, channeling, displacement, and/or re-direction), ability to form a fold axis and ability to resist mechanical failure on repeated folding and unfolding along the fold axis.

In one embodiment, porosity (void space >99%) is complete and uninterrupted in the non-compressed dressing with pore size range of 20-300 microns with substantially most of the pores near 100-200 microns. The un-interrupted pore structure is indicated in the compressed dressings by their ability to absorb biological fluid such as blood.

In some embodiments, crack free, clean edge holes near 500 microns in diameter may be formed in the dressing after compression by localized application of narrow gauge (near 500 microns in diameter), sharp pointed needle through the dressing and into a flat, hard elastomeric surface applied immediately against the dressing which may receive and release the point of the needle. Preferred receiving support flat surfaces include but are not limited to clean, dry thermoplastic elastomers with Shore 55D to 90D in hardness. Alternative methods of hole formation may include but not be limited to use of a small diameter (near 500 microns) hole punch or a laser cut hole.

In com embodiments, chitosan dressing provided herein has holes in the dressing. In some embodiments, the holes receive fiber or other reinforcing attachment elements. Such reinforcing element may be formed by simple local application of a reinforcing fluid to locally bind with the edges of the holes. A reinforcing fluid used in the development of the present invention included cyanoacrylate glue which bound the compressed chitosan lamella of the dressing together and prevented local delamination and fibrillation of the chitosan at the hole stress point. Another embodiment of a hole reinforcing element is micro-molded interlocking parts of plastic or metal (preferably dissolvable and/or degradable in the upper gastrointestinal tract or alternate area in the body of application) that are placed on one side of the hole and the opposite hole side to permanently fit together and be able to support load through the hole without causing dressing delamination, fibrillation or other stress related failure at the dressing hole when loaded. In some embodiments, the micro molded parts may include the part on the side of the attachment to a delivery device that enables convenient snap-on attachment and snap-off detachment of the dressing to the delivery device.

As used herein, the term fold axis is intended as part of the dressing sheet which demonstrates memory in the material of bending stress and or folding and is typically localized to narrow regions of high bending stress and shear. A crease in folded paper is an example of a fold axis.

In a preferred embodiment, the tissue adhesive component of the dressing is formed from a freeze phase separated and dried chitosan sheet with composition including a catechol chitosan. In a preferred embodiment the non-tissue adhesive component of the dressing is formed from a freeze phase separated chitosan dried sheet without any modified chitosan. In a preferred embodiment, both tissue adhesive and non-tissue adhesive dry sheets have density ≤about 0.03 g/cm$^3$ before compression to final density ≥about 0.4 g/cm$^3$.

In order to prepare one dressing from both sheets with the dressing having a tissue adhesive surface layer and a non-adhesive surface layer, the two sheets are bonded together by, for example, placing one sheet on top of the other and applying sufficient uniform pressure over the dressings to compress them to a higher density. In a preferred process, the original densities of each sheet type at ≤about 0.03 g/cm$^3$ is increased to a final dressing density ≥about 0.30 g/cm$^3$. In a more preferred process, the original densities of each sheet type at ≤about 0.015 g/cm$^3$ is increased to a final dressing density ≥about 0.4 g/cm$^3$. In a most preferred process, the original densities of each sheet type at ≤about 0.01 g/cm$^3$ is increased to a final dressing density ≥about 0.5 g/cm$^3$. At the conclusion of the compression, the two compressed sheets are bonded together so that one cannot be readily peeled away from the other and the dressing can be manipulated by folding and furling without any occurrence of separation.

This physical adherence of materials by compression of two or more low density porous materials together to form a final two or more layer porous material of higher density solves a difficult problem of how to adhere such materials together without physical or chemical change to the individual materials and without addition of further bonding agents or adherents. It is contemplated that bonding may be attributed to microsurface impingement and penetration of the dressings through their pores with physical interlocking due to pore compression. This physical interlocking of low density, freeze phase separated, dry sheets is not restricted to two materials of the same thickness or to only two layers since the interlocking effect is neither sidedness nor thickness dependent. Therefore a multi-layered construct of individual freeze phase separated and dried sheets of the same or different materials of the same or different thickness may be formed by layering the low density sheets (preferably with density ≤0.05 g/cm$^3$) and compressing the assembly together to a density ≥0.3 g/cm3). Such a final physically adhered assembly would be expected to provide advantages of thin top and bottom surface layers including but not limited to adhering or anti-adhering materials with layers inside providing including but not limited to structural, physical and chemical elements.

In some embodiments, a chitosan dressing has an adhesive side and a non-adhesive side. In some embodiments, the adhesive side of the chitosan adheres to a tissue and absorbs and/or redirects the surface moisture. In some embodiments, the non-adhesive side detaches from a delivery device upon attachment of the chitosan dressing to the injury site wherein the chitosan dressing has become wet. This is in part because the adhesion strength of the chitosan dressing to the tissue surface controls the dressing location upon detachment of the dressing from the delivery device. Detach or "readily detach" as used herein in a two-sided chitosan dressing indicates that the chitosan dressing, with its adherent side applied to a tissue surface or an injury site and adhered due to absorbance of moisture, stays at the tissue surface or injury site while the non-adherent side releases from the delivery device, thereby allowing the delivery device to be retracted from the injury site without disrupting the position of the chitosan dressing on the tissue surface or injury site. In some embodiments, the chitosan dressing, when dry, attaches to the delivery device, thereby allowing delivery of the chitosan dressing along with the device onto an injury site.

In one embodiment, there is a need to attach the dressing locally to the delivery device. Generally, these local attachment areas are at the extremity of the dressing. For example, one design is to provide for local pinpoint attachment on the dressing extremity tabs at the circumference of the dressing and for no other attachment locations to avoid the risk of attaching the dressing to the delivery sheath, the delivery device, or itself (when furled/folded). The attachment locations may be designed to weaken when wet or alternatively be activated for release by some type of physical release mechanism.

In one mechanism, chitosan dressing provided in this disclosure is able to stop bleeding by absorbing, channeling, and/or redirecting the hydrophilic and hydrophobic fluids at an injury site. The absorption clears enough moisture from the injury site to allow subsequent hemostatic reactions between the chitosan dressing and the tissue at the injury site, which in turn stops bleeding and allows the chitosan dressing to stay attached; thus, sealing the injury site. The porous, dense, and multi-layer structure of chitosan dressing provided herein facilitates the absorption, channeling, and/or redirection of the moisture at the injury site, and the attachment or adherence of the chitosan dressing to the injury site.

The chitosan dressing disclosed herein is biocompatible. In some embodiments, the dissolved residue from a chitosan dressing applied to an injury site in vivo passes safely through the alimentary tract and is excreted along with other bodily waste.

More than one, or multiple, chitosan dressings may be used or applied in serial fashion to a tissue treatment site or injury site. When more than one chitosan dressing is deployed, such dressings may separately adhere to adjacent tissue site or injury site areas, or may overlap with each other to varying extents. Due to the thinness of the chitosan dressing described herein, depending on the application, it is contemplated that multiple chitosan dressings may be used as needed to promote or achieve hemostasis of an injury site.

In one embodiment, the chitosan dressings overlap one another upon application. In such an instance, ideally there would be some adherence of the wetted adhesive side of the subsequent dressing to the wetted dressing backing of the earlier dressing. Accordingly, in one embodiment, the chitosan dressing does not have an anti-adherent backing but does have a backing with a weak wet adherence that provides for sufficient adherence for placement of a subsequent overlapping chitosan dressing.

Freeze phase separated dressings are composed of compacted layers of friable and delamination prone lamella that require special attachment of the dressing to wire and cylindrical laser-cut delivery devices. Each dressing attachment point to the delivery device must be able to withstand at least 50 to 100 g of load (use of units of mass, such as grams, in this and in similar contexts herein, means a load corresponding to the weight of the recited mass) during furling and unfurling of the dressing. Because of the low cohesion strength of surface lamella, direct adhesion (such as by cyanoacrylate glue) of the dressing to the delivery device is not an option for freeze phase separated dressings formed from well dissolved solutions. One embodiment where this is less problematic is where the catechol chitosan is formed from carbonic acid dissolved chitosan wherein the base precipitated and subsequently water-washed pure chitosan aqueous gel before dissolution in the carbonic chitosan contains a dispersion of solid chitosan fibers ($\geq 0.2\%$ w/w of the chitosan) insoluble in the carbonic acid that provide reinforcement to the subsequently catechol modified chitosan from carbonic solution. Besides this carbonic acid chitosan instance of a low fraction (0.2% to 5% w/w of the chitosan) chitosan fiber reinforcement of the freeze phase separated bulk and surface structure of the dressing, the preferred manner of local reinforcement and attachment of the dressing to the delivery device in the case of wire delivery is by placement of small diameter (near 500 microns), through and through holes with reinforcement elements in the dressing at the points of attachment to the delivery device.

Preformed holes in the freeze phase separated, dried dressing sponge are a preferred way to make receiving holes in the uncompressed dressing sponge. Because the low density uncompressed sponges (<0.05 g/cm3) readily delaminate, are highly friable and thus cannot receive normal hole making approaches which involve any load on the sponge, the preferred method to make holes in these sponges without any damage to the sponge lamella structure is to apply insulating, hydrophobic (non-adherent) rod mandrels to the mold solution (from the top of the solution, through the solution to the other side and contacting the base surface of the mold and preferably through the base surface and into the base of the mold) immediately before freeze phase separation of the solution. These mandrels may be tapered to allow ease of removal after drying of the freeze phase separated sponge. It is envisioned that such mandrels would be made of a rigid or semi-rigid hydrophobic material that could be machined or molded. Mandrel materials that would be suitable include but are not limited to the fluorinated materials Teflon™ and Kel-F™ and high density polyethylene (HDPE). The diameter of the hole made after removal of the mandrel is designed to allow thread to be easily placed through friable uncompressed sponge without damage to the sponge. The mandrels may be supported in the mold by slotting into suitably sized receiving holes in the mold base surface. Alternately they may be supported by a sheet of releasable hydrophobic film placed immediately over the upper surface of freeze phase separation mold and the mold solution. This film would be removed from the frozen phase separated surface, leaving the mandrels in place, before drying in the case of drying of the freeze phase separated solution. After drying, the preformed holes are thus ready to receive tie thread for attachment of dressing to delivery/deployment device. The tie thread is positioned in sponge before compression in suitable arrangement to take all the forces on dressing furling, unfurling, and delivery. Compression of sponge (from low density <0.05 g/cm3) to high density (>0.4 g/cm3) locks the tie thread and any other element of reinforcement/attachment in place. The thread may be glued in place before or after dressing compression or the thread may be used to locally apply a liquid reinforcing element such as cynanoacrylate glue locally through the hole with the thread removed after application. An alternate embodiment for forming suitable holes in the uncompressed sponge for taking a supporting thread or other type of supporting element is by laser hole cutting.

Crack free, clean edge holes near 500 microns in diameter may be formed in the dressing after compression by localized application of narrow gauge (near 500 microns in diameter), sharp pointed needle through the dressing and into a flat, hard elastomeric surface applied immediately against the dressing which may receive and release the point of the needle. Preferred receiving support flat surfaces include but are not limited to clean, dry thermoplastic elastomers with Shore 55D to 90D in hardness. Alternative methods of hole formation may include but not be limited to use of a small diameter (near 500 microns) hole punch or a laser cut hole.

Holes in the dressing can receive fiber or other reinforcing attachment elements. Such reinforcing element may be formed by simple local application of a reinforcing fluid to locally bind with the edges of the holes. A reinforcing fluid used in the development of the present invention included cyanoacrylate glue which bound the compressed chitosan lamella of the dressing together and prevented local delamination and fibrillation of the chitosan at the hole stress point. Another embodiment of a hole reinforcing element is micro-molded interlocking parts of plastic or metal (dissolvable in the upper gastrointestinal tract or alternate area in the body of application) that are placed on one side of the hole and the opposite hole side to permanently fit together and be able to support load through the hole without causing dressing delamination, fibrillation or other stress related failure at the dressing hole when loaded. It is envisioned that such micro molded parts may include the part on the side of the attachment to the delivery device that enables convenient snap-on attachment and snap-off detachment of the dressing to the delivery device.

General delivery device release of dressing may be achieved by a number of methods include snap-off detachment. A preferred method of dressing release is by using a delivery device to dressing attachment fiber that is strong when dry and weak when wet. Such fiber includes but is not limited to chitosan fiber that has been treated to become rapidly water soluble. Preferred chitosan fiber is water soluble multifilament fiber with strength >30 MPa when dry and <than 0.1 MPa when wet.

The chitosan dressing provided in this disclosure may be used to stop bleeding in suitable diseases, conditions, disorders, or emergent traumas or injuries. In some embodiments, the dressing may be used to stop bleeding from any wet physiological surface, e.g. mucus. Exemplary applications include, but are not limited to, gastrointestinal tract bleeding, other intraluminal applications, including vascular applications, internal surgical bleeding, internal biopsy bleeding, internal bleeding following parenchymal organ resection, and oral, ocular, auditory or nasal bleeding. Additional applications that might require addition of water or fluid to encourage adhesion of the chitosan dressing to a tissue surface or injury site are also contemplated, for example, use of the chitosan dressing on external body surfaces.

Chitosan dressings of the present invention may be used for treatment of gastrointestinal bleeding that may include but not be limited to treatment of bleeding in esophageal varices, bleeding from peptic ulcers, bleeding from duodenal ulcers, bleeding associated with biopsy of the upper and lower gastrointestinal tracts, resections of the upper and lower gastrointestinal tracts, and tears or ruptures in the upper and lower gastrointestinal tracts. Other diseases, conditions, disorders, or emergent traumas or injuries may include, but are not limited to, internal arterial injury; internal bleeding from the liver, internal bleeding from the vena cava; injury in the thoracic cavity including perforations of the heart and lungs and their vessels; and injuries of the abdominal cavity.

4. Sheath

The sheath is a preferred component of the device. Protective characteristics of the sheath may include, provision of a slidable overcoat to better ensure easy or unobstructed movement of the axis, expandable support, and dressing through and out of a narrow channel, protection of the dressing from premature wetting in the in vivo environment, protection of the device from any contamination that may be introduced upon loading into a narrow channel for delivery, and protection of the subject to treated with the device by limiting exposure to the expandable support and dressing until such component reach a target tissue delivery site.

Because an endoscope delivery channel is also a channel for flushing and irrigating, it may be continuously wet. In some embodiments, the dressing of the present invention cannot be allowed to become wet before its delivery to the target tissue site; thus, a protective sheath may be an essential component of the device. The wire is manufactured to fit inside the delivery tube (or sheath). In preferred embodiments, the sheath is a protective sheath that partially or wholly envelopes (or encloses) the expandable support and dressing. In some embodiments, the sheath overlies or envelopes the entirety or a portion of the expandable support and/or dressing. For example, the sheath may partially or wholly envelop the expandable support and dressing when the expandable support is in an unexpanded format and the dressing is in a compact condition. In some embodiments, the sheath partially or wholly envelopes the axis along with the expandable support and dressing. The distal end of the delivery sheath is preferably sealed from ingress of external moisture by an easily rupturable end. Preferably this rupturable end is formed of a rupturable diaphragm inside the end of the delivery sheath that protects the dressing inside the sheath from premature contact with moisture. The delicate diaphragm is protected inside the distal end of the delivery sheath so that handling or delivery sheath passage down the inside of the endoscope delivery channel cannot cause premature rupture of the diaphragm. The diaphragm protects the inside contents of the sheath but is sufficiently delicate that passage of the dressing through the sheath (even if it is the distal end of the dressing rupturing the diaphragm) does not damage the dressing.

At or prior to introduction at the target tissue site, the sheath distal diaphragm may be ruptured by the wire body driven passage of the wire delivery device end and dressing through the diaphragm. This rupture initiates exit of dressing outside of the sheath and the expansion of the expandable support and dressing once they exit the restrictive space of the sheath.

In one embodiment, the expandable support automatically goes into an expanding format and/or an expanded format upon rupture of the distal end of the sheath. In one embodiment, the sheath may be ruptured when the expandable support goes from an unexpanded format into an expanding format and/or an expanded format. In one embodiment, the sheath may be ruptured remotely by triggering a mechanical rupture mechanism associated with the protective sheath.

Use in Combination with Other Device Components

In some embodiments, the device of the present invention can be used in combination with other device components. For example, the device disclosed herein may comprise an annular ring expandable support that can be used with another device component having a wire expandable support in the form of a stable balloon.

Combining multiple device components can allow for fine control and proper positioning procedures for application of the dressing at a target tissue site.

Embodiments of Gastrointestinal Delivery Device

FIGS. 11a-11c, 12a, 12b, 13a-13f, 14a, 14b, 15a, and 15b depict various aspects of preferred embodiments of the devices described herein.

Figure 11A:
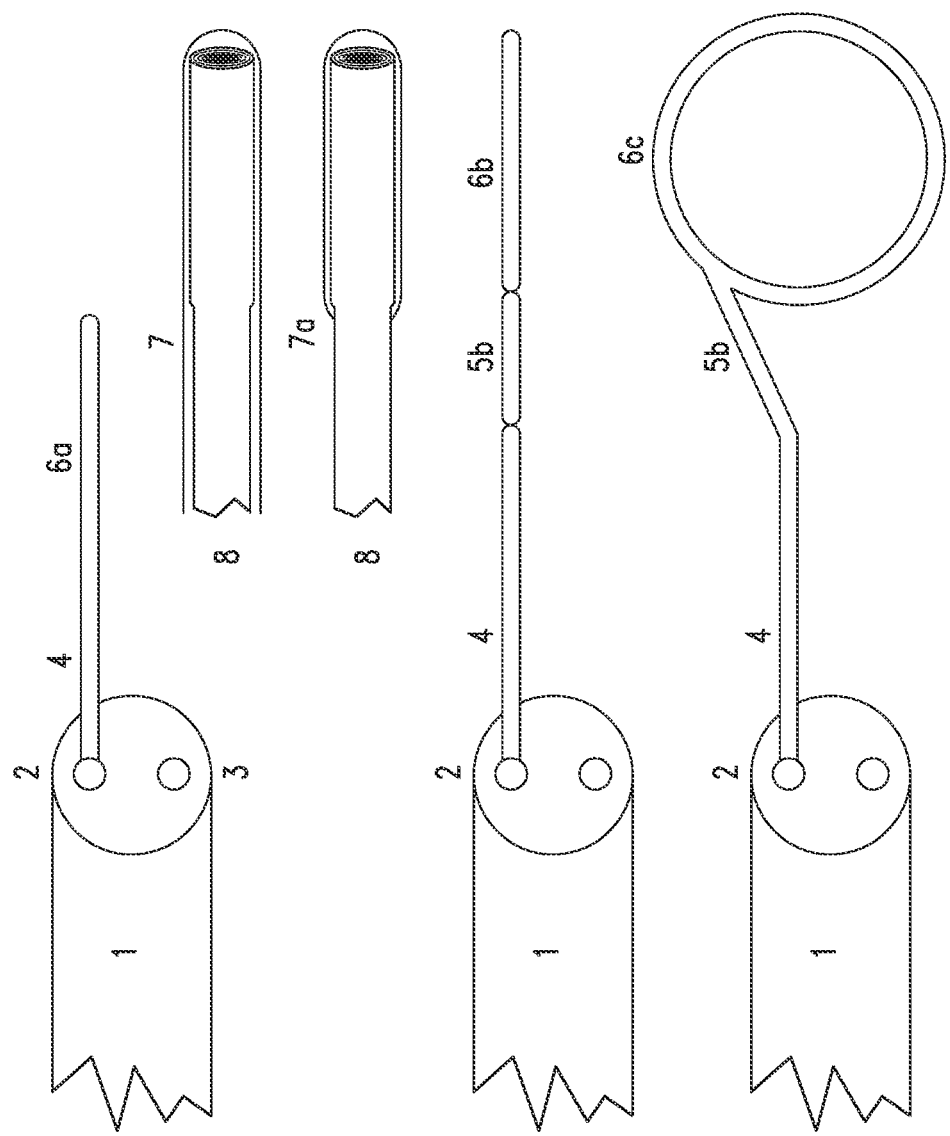
FIG. 11a provides schematic drawings of portions of a delivery system for a dressing for controlling gastrointestinal bleeding, including wire components thereof.
Figure 11B:
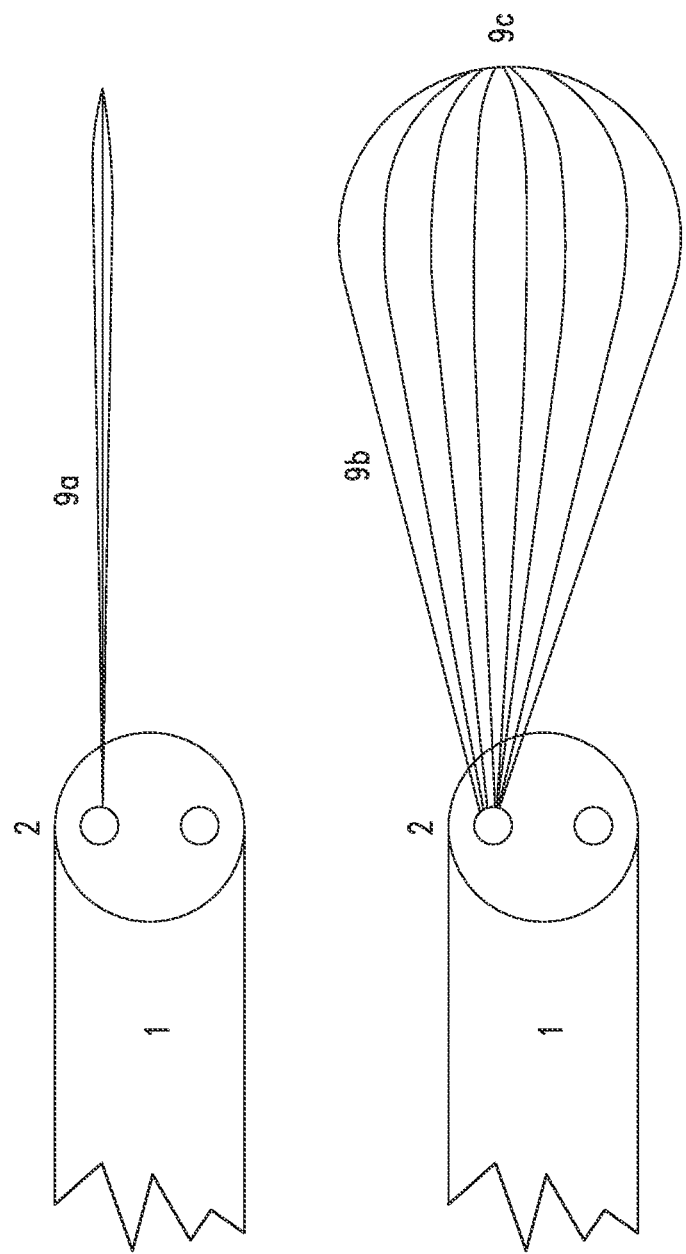
FIG. 11b provides schematic drawings of portions of a delivery system for a dressing for controlling gastrointestinal bleeding, including balloon components thereof.
Figure 11C:
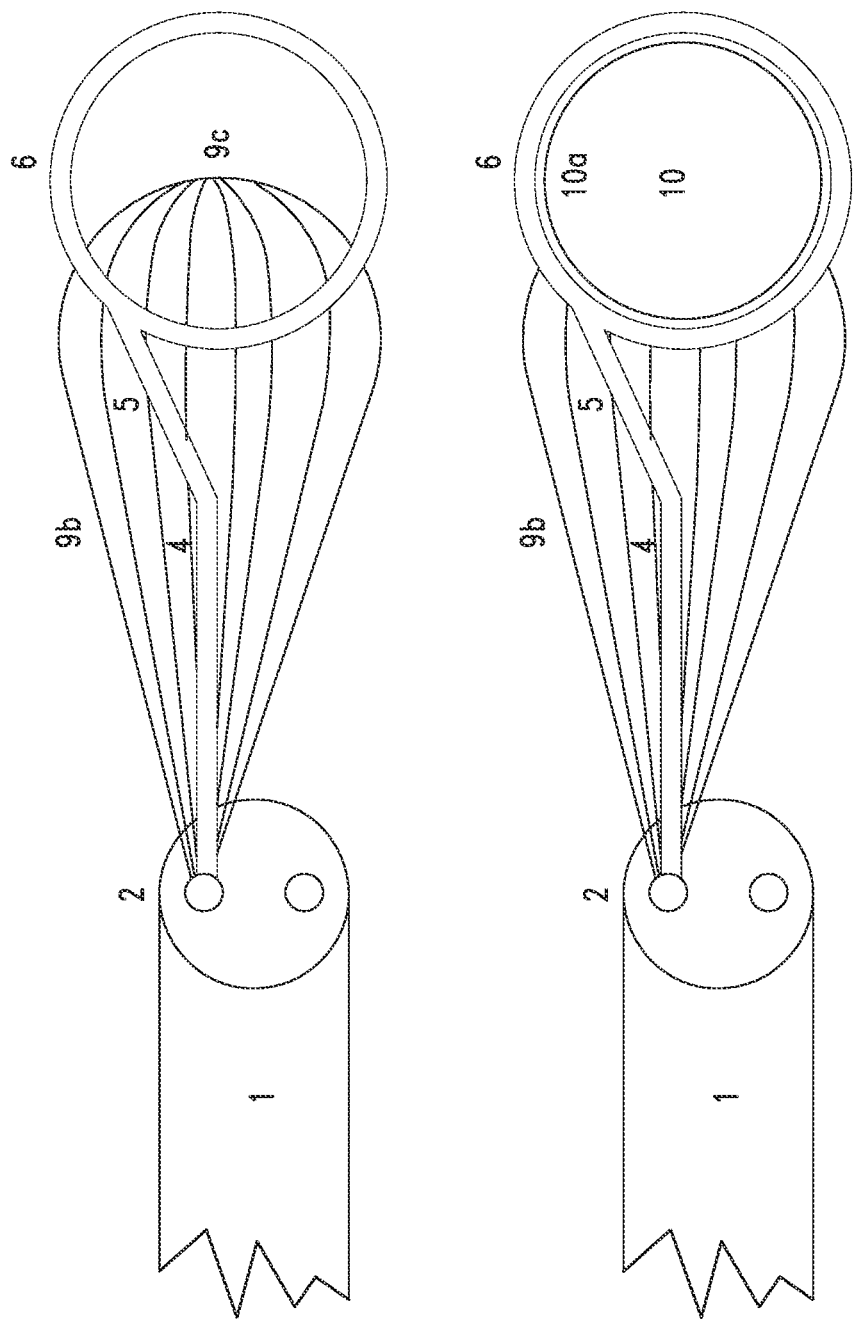
FIG. 11c provides schematic drawings of a delivery system for a dressing for controlling gastrointestinal bleeding, including the wire components illustrated in FIG. 11a and the balloon components of FIG. 11b.

FIGS. 11a-11c show a schematic drawings side on aspect of the end of an endoscope used in gastroscopy and different stages of wire delivery of a preferred delivery method. Chitosan dressing was used in this embodiment (although dressings can be delivered as well). In FIGS. 11a-11c, chitosan dressing is bound to an expandable support (6a-6c). In the depicted end of the gastroscope, there is a base optic fiber viewing port and a top delivery port that is the distal end of a communication channel that runs the length of the gastroscope. Delivery ports and channels in gastroscopes are commonly 2.8 mm in diameter and may also be 3.2 mm in diameter in some specialized gastroscopes. Custom gastroscopes may have larger diameter delivery ports and channels but they are less common.

It is envisioned that the wire delivery device end comprising the chitosan dressing in a compact condition will preferably be able to pass down a 4.0 mm diameter channel, more preferably a 3.2 mm diameter channel, and most preferably be able to pass down a 2.8 mm diameter delivery channel to enable the dressing and delivery device of the invention to be used universally.

FIG. 11a provides a schematic drawing of a preferred device embodiment comprising a spring wire tip, preferably formed of ribbon spring wire. In some embodiments, the device comprising a spring wire tip includes: (1) a wire primary support shaft, or support shaft; (2) an articulated spring locator positioning arm that connects to the wire support shaft at one end, and connecting at the other end; and (3) an expandable support that is a ribbon spring annular dressing support. In some embodiments, the device further comprises a chitosan dressing releasably attached to an expandable support. Inside the gastroscope communication channel, the spring locator positioner is z-folded at articulated spring hinge points at each of tis proximal and distal ends to overlay the support shaft and a tightly furled annular dressing support. The three parts are aligned along the axis of the communication channel in a tight bundle which is supported by an overlaying thin protective sheath tube whose end is ruptured on exiting the delivery port. On rupturing, the end of the protective sheath tube, the annular dressing support opens and the spring locator positioner aligns the annular dressing support orthogonal to the distal exposed primary support shaft. The primary support shaft extends the length of the gastroscope channel enabling the operator to provide the annular dressing support to a bleeding target tissue site, using the visual imaging of the gastroscope viewport and flexibility in the gastroscope tip. Delivery of the dressing using this approach requires a second wire (dual wires in the gastroscope communication channel) which is described in FIG. 11b.

FIG. 11b provides a schematic drawing of another embodiment of the device of the present invention. In some embodiments, the expandable support is a spring wire tip in the form of a balloon or spring wire frame, that on exiting the distal end of the gastroscope communication channel may open (or inflate) into one of an expanding format or an expanded format to provide a "cushion" end that may also provide a dressing attachment location. In some embodiments, the cushion end of the expandable support aligns orthogonally with the annular dressing support noted above in connection with FIG. 11a. When used together with the embodiment provided in FIG. 11a, this alignment provides for hand operated or spring actuated loading centrally onto a chitosan dressing supported within the annular dressing frame support on the first wire (the spring wire tip in FIG. 11a). This loading along the second wire tip onto the cushion end provides for release and removal of the dressing from the annular support frame by tearing of perforations at the outer circumference of the dressing and delivery and brief holding (10 to 60 seconds) of the dressing with application of pressure onto the targeted injury site. In this embodiment, the spring wire tip serves as both the expandable support and the wire support shaft.

FIG. 11c provides a schematic drawing of combined use of the embodiments provided in FIGS. 11a and 11b, where the first (FIG. 11a embodiment) and second wire (FIG. 11b embodiments) ends applied together with and without a dressing present on the annular dressing support.

Figure 12A:
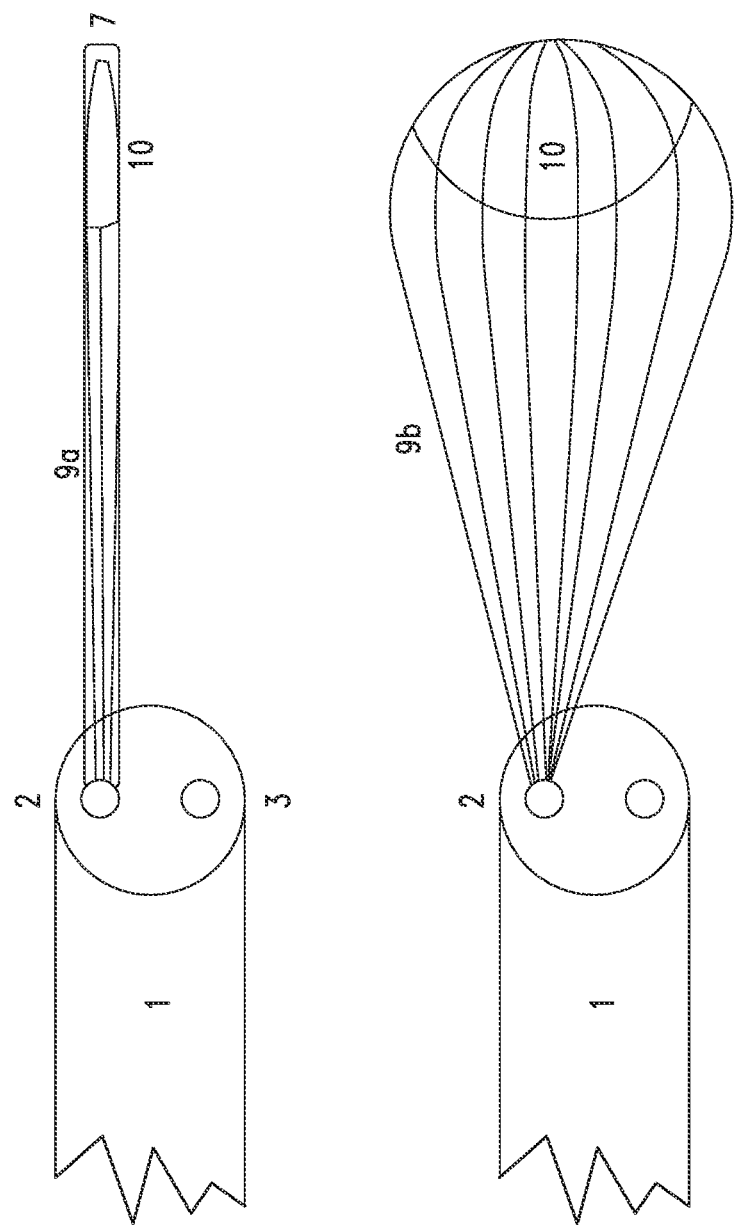
Figure 12B:
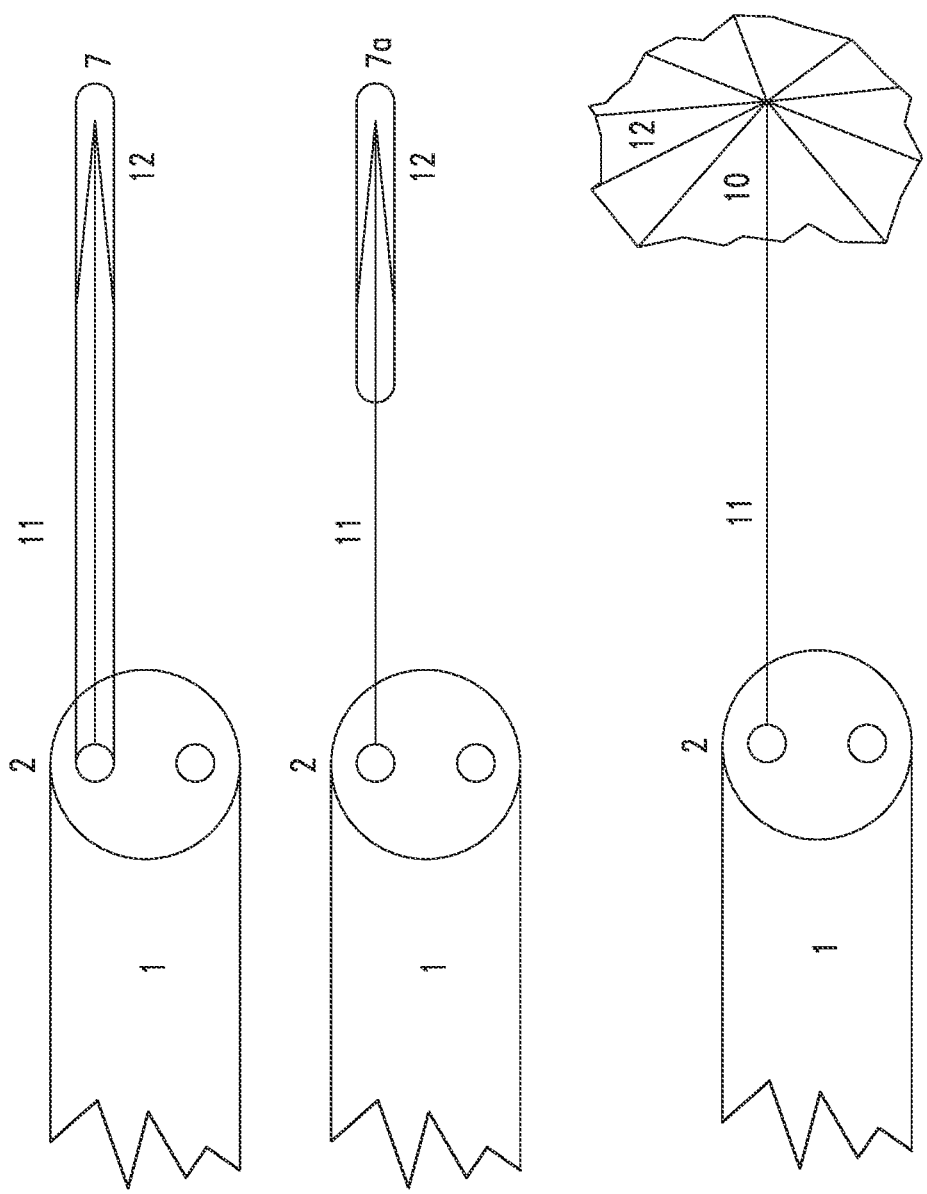
FIG. 12b provides schematic drawings of another delivery system for a dressing for controlling gastrointestinal bleeding, including an umbrella-like structure that can be expanded or collapsed to control deployment of the dressing.

FIG. 12a and FIG. 12b provide two alternate embodiments of wire delivery of the dressing using only single wire delivery in each. FIG. 12a involves attachment of the dressing to the cushion end of the embodiment provided in FIG. 11b. FIG. 12b involves an opening "umbrella style" wire frame with multiple spring wire "umbrella style" spokes that open about 90° and serve as the expandable support on sheath removal and provide for orthogonal alignment of the dressing in a splayed condition relative to the axis of the gastroscope delivery port. The dressing is sufficiently loosely attached in both alternate embodiments after removal of the protective sheath on exiting the delivery port that the wet tissue adhesion on placement allows for release of the dressing from the delivery end.

FIGS. 13a-13f depict preferred embodiments of the delivery device formed of an assembly of spring wire expandable support whereby at least three corners of the releasable dressing are attached to individual arms (alternatively spokes) of the spring wire. The individual arm attachment is preferably at articulated dressing tabs radiating from the dressing edge. The tabs may be reinforced which may include, but not be limited to, localized additional dressing density, additional dressing thickness and sewn fiber at the tabs and with the reinforcement radiating from the tabs to the dressing center. In some embodiments, the expandable support comprises the spring wire arms which are attached to the dressing tabs. The attachment may be achieved through eyelet holes in the tabs accommodating wire arm ends, by fiber, by glue and by pinched fitting, and other suitable ways. The spring wire assumes its expanding format and/or expanded format when it is freed from the sheath tube. The outer diameter of the sheath tubing is sufficiently small to pass down the delivery channel of the endoscope. The inner diameter of the delivery sheath tubing is sufficiently large to accommodate the folded spring wire assembly and the dressing attached to the end of the spring wire assembly. Once freed from its supportive sheath tubing, the spring wire arms enable unfurling of the supported chitosan gastrointestinal dressing, while locating the unfurled dressing orthogonal to the distal end of the endoscope channel ready for deployment on the wound, or target tissue site. Release of dressing from the wire delivery device may include but not be limited to draw string release, tearing pre-perforated regions of dressing, using localized moisture contact to weaken material in the dressing, and eyelets in corners of the dressing from which the delivery wire may be removed away from the target tissue site once the dressing placed and adhered.

Figure 13A:
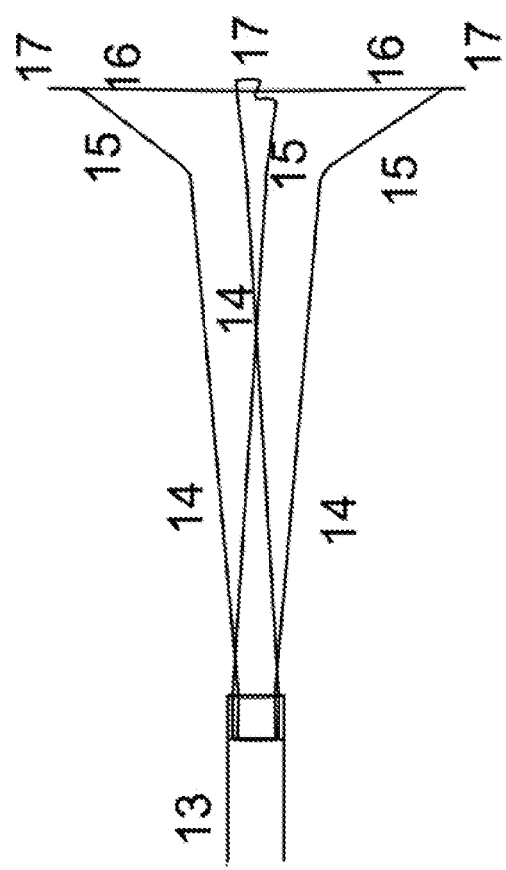
FIG. 13a provides a schematic drawing of a side view of another delivery system that includes a plurality of radially-spaced apart arms in an expanded format.
Figure 13B:
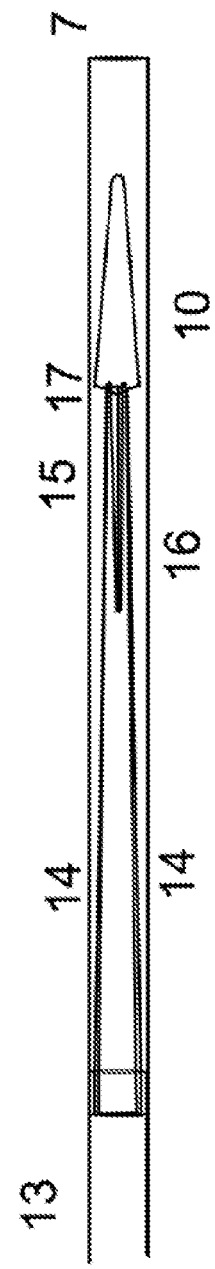
FIG. 13b provides another schematic drawing of a side view of the delivery system of FIG. 13a in an unexpanded format.
Figure 13C:
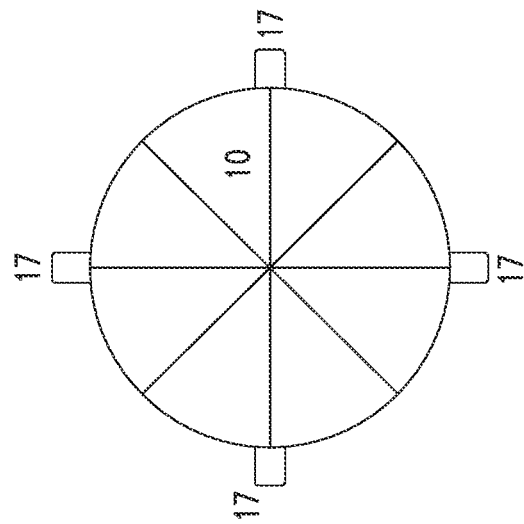
FIG. 13c provides a schematic drawing of an end view of the delivery system of FIGS. 13a-13b in the expanded format without a dressing coupled thereto.
Figure 13D:
FIG. 13d provides a schematic drawing of another end view of the delivery system of FIGS. 13a-13c in the expanded format with a dressing coupled thereto (normally the four attachment tabs (17) would be hidden & folded back behind the front of the dressing to provide attachment to the delivery device. The tabs are shown here extended for completeness of the image of the dressing form).
Figure 13E:
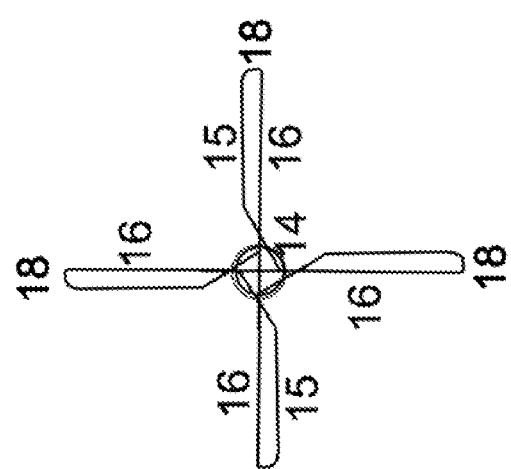
FIG. 13e provides a schematic drawing of another end view of the delivery system of FIGS. 13a-13d in a partially expanded format with a dressing coupled thereto, the dressing partially folded.
Figure 13F:
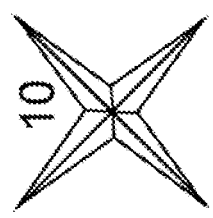
FIG. 13f provides a schematic drawing of another end view of the delivery system of FIGS. 13a-13e in an unexpanded format with a dressing coupled thereto, the dressing folded and partially wrapped about components of the delivery system.

FIG. 13a depicts the preferred embodiment viewed side-on and with the spring wire in its expanding format and/or expanded format and with four point dressing attachment. FIG. 13b depicts the preferred embodiment of FIG. 13a viewed side-on with the spring wire and dressing in its unexpanded format and compact condition, respectively, inside the sheath tubing. FIG. 13c shows the embodiment of FIG. 13a without an attached dressing viewed looking along the delivery wire support axis towards the gastroscope delivery port. FIG. 13d depicts a planar view of a circular dressing with eight folds at 45° to each other and four attachment tabs radiating from the circumference of the dressing and at 90° to one another. FIG. 13e depicts a planar view of a partially folded dressing of FIG. 13b. FIG. 13f depicts a planar view of 13b with wrapped folding of the 4 fluted fold arms of FIG. 13e to accommodate the dressing within the narrow confines of the tube sheath.

The following reference identifiers for FIGS. 11a-11c, 12a, 12b, and 13a-13f are provided with further narrative description as follows: 1—Gastroscope body; 2—Gastroscope delivery port at distal end of gastroscope communicating channel; 3—Gastroscope optic fiber illumination and viewing port; 4—Primary support wire shaft (a type of wire support axis); 5—Articulated spring locator positioning arm; with 5a (hidden) as z-folded positioning arm aligned with 4; with 5b as released spring locator positioning arm providing for orthogonal alignment of 6 with 4; 6—dressing support frame (a type of expandable support) (represented here as annular but it may include different shapes); with 6a furled and aligned with 4; with 6b released from alignment with 4 and allowed to unfurl; with 6c fully unfurled and presenting its annular face centrally and orthogonally with 4; 7—Thin plastic protective sheath tubing overlying and encompassing the wire delivery device and chitosan dressing before delivery; 7a—Alternate short length thin plastic protective sheath tubing overlying the chitosan dressing before delivery; 8—Expanded view of the folded and collapsed wire end; 9—9a shows the collapsed wire tip of the embodiment provided in FIG. 11b, that is suitable for use with the embodiment provided in FIG. 11a—the dual wire delivery method; 9b shows the expanded wire tip of the embodiment provided in FIG. 11b that expands on exiting the distal end of the delivery tube; 9c provides a cushioned end formed of expanded spring wire frame or inflated and directional stable balloon (different types of expandable support) that loads the dressing supported in 6c to provide for its detachment and application on an injury site; 10 shows the dressing, e.g. chitosan dressing (represented here as round in shape, however it's shape may include different shapes including, but not limited to, circular, circular and petal-shaped, triangular, square, rectangular, pentagonal, hexagonal and octagonal); 10a shows a perforated circumference of the dressing to provide for release from the annular support frame 6 on application of 9c orthogonal to the dressing face; 10—shows the chitosan dressing in different states: either folded/furled or unfolded/unfurled, and either inside a protective sheath or not within a protective sheath; 11—wire support axis in alignment with gastroscope delivery channel axis acting as a delivery shaft and support for umbrella style dressing delivery; 12—Wire spring spokes of the umbrella (expandable support) that open about 90° relative to 11 on release from the protective sheath 7 and act in concert to present the dressing orthogonal to 11; 13—wire device body that conforms to endoscope delivery channel inside tubing sheath with distal end supporting sprung delivery wire and dressing; 14—articulated spring arms that together act as the wire support axis 11; 15—articulated spring arms connecting 14 to the dressing 10; 16—articulated base support spring struts (expandable support) that connect ends of 15 together and, when released from 7, provides for base dressing support loading against injury site and together with 15 provide for 12; 17—tab attachment points to 15 (and 12); 18—extremity wire ends of wire delivery device to attach to folded back dressing tab attachment points.

The delivery systems illustrated in FIGS. 11a-11c, 12a, 12b, and 13a-13f can be described in other ways. For example, the delivery system illustrated in FIG. 11a may include an outer sheath 1, which may be an outer sheath of an endoscope such as a gastroscope. The outer sheath 1 may have a first opening or port 2 at a distal end thereof, through which a wire or other support shaft 4 may extend. The outer sheath 1 may have a second opening or port 3 at the distal end thereof, which can function as an eyepiece to allow an operator to view operation of the support shaft 4 and other components coupled thereto. The delivery system illustrated in FIG. 11a may also include the support shaft 4, which can be extended distally or retracted proximally, and/or rotated with respect to the outer sheath 1. Thus, a distal end portion of the support shaft 4 can be surrounded and protected by the outer sheath 1 while the delivery system is inserted into a patient's body, and the distal end portion of the support shaft 4 can be moved outside of the outer sheath 1 through the port 2 for use once the delivery system has been inserted into a patient's body.

The delivery system illustrated in FIG. 11a also includes a positioning arm 5b that may be coupled, such as rigidly and/or integrally coupled, to a distal end of the support shaft 4. When the delivery system illustrated in FIG. 11a is in a fully deployed configuration, the positioning arm 5b may be coupled to the distal end of the support shaft 4 at an oblique angle, so that the positioning arm 5b extends both longitudinally, in a direction aligned with the distal end of the support shaft 4, and radially, in a direction transverse to the distal end of the support shaft 4. The delivery system illustrated in FIG. 11a also includes a support frame 6, identified in different configurations in FIG. 11a by reference numerals 6a, 6b, and 6c. The support frame 6 may be coupled, such as rigidly and/or integrally coupled, to a distal end of the positioning arm 5b. When the delivery system illustrated in FIG. 11a is in a fully deployed configuration, the support frame 6 may comprise a circular piece of wire or other material, and may be coupled to the distal end of the positioning arm 5b at an angle such that its circular shape is oriented perpendicular to the distal end portion of the support shaft 4.

The delivery system illustrated in FIG. 11a also includes an inner sheath that is located inside the outer sheath 1 and that extends around and protects at least the distal end portion of the support shaft 4, the positioning arm 5b, and the support frame 6. As illustrated in FIG. 11a, the delivery system may include a relatively short inner sheath 7a that covers a relatively small distal end portion of the support shaft 4, the positioning arm 5b, and the support frame 6, or the delivery system may include a relatively long inner sheath 7 that covers an entirety of or a relatively long distal end portion of the support shaft 4, the positioning arm 5b, and the support frame 6.

FIG. 11b illustrates that the delivery system of FIG. 11a may also include a balloon 9, portions of which are identified in different configurations in FIG. 11b by reference numerals 9a, 9b, and 9c. The balloon 9 may extend out of the first port 2 at the distal end of the outer sheath 1. The balloon 9 can be extended distally or retracted proximally with respect to the outer sheath 1. Thus, the balloon 9 can be deflated and surrounded and protected by the outer sheath 1 while the delivery system is inserted into a patient's body, and the balloon 9 can be moved outside of the outer sheath 1 through the port 2 and inflated for use once the delivery system has been inserted into a patient's body. FIG. 11c illustrates the delivery system of FIG. 11a with both the support shaft 4 and the balloon 9 extending out of the first port 2 at the distal end of the outer sheath 1 at the same time, or simultaneously or concurrently. In such embodiments, the inner sheath that encloses the components as described above may also enclose the balloon 9, or the delivery system may include a second inner sheath distinct from the inner sheath described above, that encloses the balloon 9. FIG. 11c also illustrates that a dressing 10 having a generally circular shape may be mounted to the support frame and may span across a circular opening of the circular support frame 6.

To assemble and prepare the delivery system of FIGS. 11a-11c for use, an operator may begin with the delivery system in the configuration illustrated in the upper portion of FIG. 11c. The operator may then deflate the balloon 9. The operator may then couple the dressing 10 to the support frame 6 such that the dressing 10 spans across the circular opening of the circular support frame 6 in accordance with the description of such features provided elsewhere herein. The dressing 10, the support frame 6, and the positioning arm 5b may then be folded up, such as so that the positioning arm 5b is bent backwards and lays flush against the distal end portion of the support shaft 4. The distal end portion of the support shaft 4, the positioning arm 5b, the support frame 6, and/or the deflated balloon 9 can then be positioned within an inner sheath such as the inner sheath 7 or the inner sheath 7a. Such components can then be retracted with respect to the outer sheath 1 until they are inside of, and covered and protected by, the outer sheath 1.

To use the delivery system of FIGS. 11a-11c, an operator such as a physician may insert the outer sheath 1, which may be an outer sheath of an endoscope such as a gastroscope, into a patient's body, such as through the patient's mouth and into the patient's stomach. Once the distal end of the outer sheath 1 is located at a desired position within a patient's body, such as in the patient's stomach, the operator can move the balloon 9 and support shaft 4 distally with respect to the outer sheath 1. In some cases, while the operator does so, the inner sheath remains stationary, and moving the support shaft 4 distally punctures or ruptures the distal end of the inner sheath so that the distal end portion of the support shaft 4 and other associated components, including the balloon 9, can extend distally out of both the outer sheath 1 and the inner sheath.

As the support shaft 4 moves distally with respect to the outer and inner sheaths in this manner, the positioning arm 5b and the support frame 6 are released and are allowed to unfold with respect to one another within the patient's body. The operator can then view the position of such components, and of the dressing 10, through the eyepiece 3, and can move the support shaft 4 along the length of the outer sheath 1, and/or rotate the support shaft 4 with respect to and about the length of the outer sheath 1, so as to position the dressing 10 at a desired location, for example, such that a first side of the dressing 10 lies against an internal wall of an internal lumen inside the patient's body, such as a wall of the patient's stomach. Once the dressing 10 has been desirably positioned in this manner, the operator can inflate the balloon 9 and position the balloon 9 adjacent to and in abutting contact with a second side of the dressing 10 opposite the first side thereof, and can urge the inflated balloon to press against the second side of the dressing 10. In this manner, the dressing 10 may be pressed against the wall of a lumen inside the patient's body, thereby causing the dressing 10 to stick to the wall in accordance with the description of such features provided elsewhere herein.

Once the dressing 10 has been pressed against the wall, the dressing 10 can be released from the support frame 6 in accordance with the description of such features provided elsewhere herein. The balloon 9 can then be deflated and retracted longitudinally and proximally into the outer sheath 1. The support shaft 4 can then be retracted longitudinally and proximally into the outer sheath 1. In some cases, retracting the support shaft 4 into the outer sheath 1 can automatically induce the positioning arm 5b and/or the support frame 6 to fold up as they are pulled into the outer sheath 1 through the first port 2. The outer sheath 1, and the endoscope or gastroscope of which it is a part, can then be retracted out of the patient, such as out of the patient's stomach through the patient's mouth.

As another example, the delivery system illustrated in FIG. 12a may include an outer sheath 1, which may be an outer sheath of an endoscope such as a gastroscope. The outer sheath 1 may have a first opening or port 2 at a distal end thereof, through which a balloon 9, identified in the drawings in deflated and inflated configurations as 9a and 9b, respectively, may extend. The outer sheath 1 may have a second opening or port 3 at the distal end thereof, which can function as an eyepiece to allow an operator to view operation of the balloon 9 and other components coupled thereto. The delivery system illustrated in FIG. 12a may also include the balloon 9, which can be extended distally or retracted proximally, and/or rotated with respect to the outer sheath 1. Thus, a distal end portion of the balloon 9 can be surrounded and protected by the outer sheath 1 while the delivery system is inserted into a patient's body, and the distal end portion of the balloon 9 can be moved outside of the outer sheath 1 through the port 2 for use once the delivery system has been inserted into a patient's body.

The delivery system illustrated in FIG. 12a can omit, or not include, and function without, the support shaft 4, the positioning arm 5b, and/or the support frame 6 illustrated in FIGS. 11a-11c. FIG. 12a also illustrates that a dressing 10 having a generally circular shape may be mounted to the balloon 9 and may span across a circular or generally dome-shaped distal end portion of the balloon 9 when the balloon 9 is in an inflated configuration. The delivery system illustrated in FIG. 12a also includes an inner sheath 7 that is located inside the outer sheath 1 and that extends around and protects at least the distal end portion of the balloon 9.

To assemble and prepare the delivery system of FIG. 12a for use, an operator may begin with the delivery system in the configuration illustrated in the lower portion of FIG. 12a. The operator may then couple the dressing 10 to the balloon 9, such as to a generally dome-shaped distal end portion of the balloon 9. The operator may then deflate the balloon 9, and as the balloon 9 deflates, the dressing 10 may be folded up, such as in accordance with related description provided elsewhere herein. The distal end portion of the balloon 9 and the folded-up dressing 10 can then be positioned within the inner sheath 7. Such components can then be retracted with respect to the outer sheath 1 until they are inside of, and covered and protected by, the outer sheath 1.

To use the delivery system of FIG. 12a, an operator such as a physician may insert the outer sheath 1, which may be an outer sheath of an endoscope such as a gastroscope, into a patient's body, such as through the patient's mouth and into the patient's stomach. Once the distal end of the outer sheath 1 is located at a desired position within a patient's body, such as in the patient's stomach, the operator can move the balloon 9 distally with respect to the outer sheath 1. In some cases, while the operator does so, the inner sheath 7 remains stationary, and moving the balloon 9 distally punctures or ruptures the distal end of the inner sheath 7 so that the distal end portion of the balloon 9 and other associated components, including the dressing 10, can extend distally out of both the outer sheath 1 and the inner sheath 7.

Once the balloon 9 is moved distally with respect to the outer and inner sheaths 1, 7 in this manner, the operator can inflate the balloon 9. The operator can then move the balloon 9 longitudinally, such as distally or proximally, and/or rotate the balloon 9, with respect to the outer sheath 1, while keeping the outer sheath 1 stationary, to position the dressing 10 at a desired location. The operator can then view the position of such components through the eyepiece 3, and can continue to move and/or rotate the balloon 9 with respect to the outer sheath 1 so as to position the dressing 10 at a desired location, for example, such that a side of the dressing 10 opposite the balloon 9 lies against an internal wall of an internal lumen inside the patient's body, such as a wall of the patient's stomach. Once the dressing 10 has been desirably positioned in this manner, the operator can urge the inflated balloon 9 to press the side of the dressing 10 into the wall. In this manner, the dressing 10 may be pressed against the wall of a lumen inside the patient's body, thereby causing the dressing 10 to stick to the wall in accordance with the description of such features provided elsewhere herein.

Once the dressing 10 has been pressed against the wall, the dressing 10 can be released from the balloon 9 in accordance with the description of such features provided elsewhere herein. The balloon 9 can then be deflated and retracted longitudinally and proximally into the outer sheath 1. The outer sheath 1, and the endoscope or gastroscope of which it is a part, can then be retracted out of the patient, such as out of the patient's stomach through the patient's mouth.

As another example, the delivery system illustrated in FIG. 12b may include an outer sheath 1, which may be an outer sheath of an endoscope such as a gastroscope. The outer sheath 1 may have a first opening or port 2 at a distal end thereof, through which a support wire 11 may extend. The outer sheath 1 may have a second opening or port 3 at the distal end thereof, which can function as an eyepiece to allow an operator to view operation of the support wire 11 and other components coupled thereto. The delivery system illustrated in FIG. 12b may also include the support wire 11, which can be extended distally or retracted proximally, and/or rotated with respect to the outer sheath 1. Thus, a distal end portion of the support wire 11 can be surrounded and protected by the outer sheath 1 while the delivery system is inserted into a patient's body, and the distal end portion of the support wire 11 can be moved outside of the outer sheath 1 through the port 2 for use once the delivery system has been inserted into a patient's body.

The delivery system illustrated in FIG. 12b also includes a plurality of wire support arms 12 that may be coupled, such as rigidly and/or integrally coupled, to a distal end of the support wire 11. When the delivery system illustrated in FIG. 12b is in a fully deployed configuration, the support arms 12 may be coupled to the distal end of the support wire 11 at oblique and/or right angles, so that the support arms 12 extend either both longitudinally, in a direction aligned with the distal end of the support wire 11, and radially, in a direction transverse to the distal end of the support wire 11, or purely radially, in the direction transverse and perpendicular to the distal end of the support wire 11.

The delivery system illustrated in FIG. 12b also includes an inner sheath that is located inside the outer sheath 1 and that extends around and protects at least the distal end portion of the support wire 11 and the support arms 12. As illustrated in FIG. 12b, the delivery system may include a relatively short inner sheath 7a that covers a relatively small distal end portion of the support wire 11 and the support arms 12, or the delivery system may include a relatively long inner sheath 7 that covers an entirety of or a relatively long distal end portion of the support wire 11 and the support arms 12. FIG. 12b also illustrates that a dressing 10 having a generally circular shape may be mounted to the support arms 12 and may span across a distal end portion of the delivery system. In some cases, an overall shape of the distal end portion of the delivery system may be defined by the outer terminal ends of the support arms 12, and may have an approximately circular shape.

To assemble and prepare the delivery system of FIG. 12b for use, an operator may begin with the delivery system in the configuration illustrated in the lower portion of FIG. 12b. The operator may then couple the dressing 10 to the support arms 12 such that the dressing 10 spans across the generally circular shape of the distal end of the delivery system in accordance with the description of such features provided elsewhere herein. The dressing 10 and the support arms 12 may then be folded up, such as so that the support arms 12 are bent backwards and lay flush against the distal end portion of the support wire 11. The distal end portion of the support wire 11, the support arms 12, and the dressing 10 can then be positioned within an inner sheath such as the inner sheath 7 or the inner sheath 7a. Such components can then be retracted with respect to the outer sheath 1 until they are inside of, and covered and protected by, the outer sheath 1.

To use the delivery system of FIG. 12b, an operator such as a physician may insert the outer sheath 1, which may be an outer sheath of an endoscope such as a gastroscope, into a patient's body, such as through the patient's mouth and into the patient's stomach. Once the distal end of the outer sheath 1 is located at a desired position within a patient's body, such as in the patient's stomach, the operator can move the support wire 11 distally with respect to the outer sheath 1. In some cases, while the operator does so, the inner sheath remains stationary, and moving the support wire 11 distally punctures or ruptures the distal end of the inner sheath so that the distal end portion of the support wire 11 and other associated components can extend distally out of both the outer sheath 1 and the inner sheath.

As the support wire 11 moves distally with respect to the outer and inner sheaths in this manner, the support arms 12 are released and are allowed to unfold with respect to one another within the patient's body. The operator can then view the position of such components, and of the dressing 10, through the eyepiece 3, and can move the support wire 11 along the length of the outer sheath 1, and/or rotate the support wire 11 with respect to and about the length of the outer sheath 1, so as to position the dressing 10 at a desired location, for example, such that a side of the dressing 10 lies against an internal wall of an internal lumen inside the patient's body, such as a wall of the patient's stomach. Once the dressing 10 has been desirably positioned in this manner, the operator can urge the support wire 11 to press the dressing 10 against the wall of the lumen inside the patient's body, thereby causing the dressing 10 to stick to the wall in accordance with the description of such features provided elsewhere herein.

Once the dressing 10 has been pressed against the wall, the dressing 10 can be released from the support arms 12 in accordance with the description of such features provided elsewhere herein. The support wire 11 can then be retracted longitudinally and proximally into the outer sheath 1. In some cases, retracting the support wire 11 into the outer sheath 1 can automatically induce the support arms 12 to fold up as they are pulled into the outer sheath 1 through the first port 2. The outer sheath 1, and the endoscope or gastroscope of which it is a part, can then be retracted out of the patient, such as out of the patient's stomach through the patient's mouth.

As another example, the delivery system illustrated in FIGS. 13a-13f may include an outer sheath 13, which may be an outer sheath of an endoscope such as a gastroscope. The outer sheath 13 may have a first opening or port at a distal end thereof, through which a plurality of support wires 14, 15 may extend. In the embodiment illustrated in FIGS. 13a-13f, the plurality of support wires 14, 15 includes exactly four support wires 14, 15, but in other embodiments, the plurality of support wires 14, 15 may include any suitable number of support wires 14, 15, such as exactly three, five, six, seven, eight, nine, ten, twelve, fifteen, or more support wires 14, 15. The outer sheath 13 may have a second opening or port at the distal end thereof, which can function as an eyepiece to allow an operator to view operation of the support wires 14, 15 and other components coupled thereto. The delivery system illustrated in FIGS. 13a-13f may also include the support wires 14, 15, which can be extended distally or retracted proximally, and/or rotated with respect to the outer sheath 13. Thus, distal end portions of the support wires 14, 15 can be surrounded and protected by the outer sheath 13 while the delivery system is inserted into a patient's body, and the distal end portions of the support wires 14, 15 can be moved outside of the outer sheath 13 through the port for use once the delivery system has been inserted into a patient's body.

As illustrated in FIGS. 13a and 13c, when the delivery system of FIGS. 13a-13f is in a deployed configuration, each of the support wires 14, 15 has a proximal portion 14 that extends out of the port at the distal end of the outer sheath 13, and a distal portion 15 that extends from the proximal portion 14 to the distal end of the support system. The distal portion 15 may be coupled to, such as rigidly and/or integrally coupled to, the proximal portion 14 at an angle and at a joint. As further illustrated in FIGS. 13a and 13c, the proximal portions 14 extend at oblique angles with respect to the distal end portion of the outer sheath 13, so that the proximal portions 14 extend both longitudinally, in a direction aligned with the distal end portion of the outer sheath 13, and radially, in a direction transverse to the distal end portion of the outer sheath 13. As further illustrated in FIGS. 13a and 13c, the distal portions 15 also extend at oblique angles with respect to the distal end portion of the outer sheath 13, so that the distal portions 15 extend both longitudinally, in a direction aligned with the distal end portion of the outer sheath 13, and radially, in a direction transverse to the distal end portion of the outer sheath 13. As illustrated in FIG. 13a, the oblique angle between the orientation of the distal portions 15 and the distal end portion of the outer sheath 13 is greater than the oblique angle between the orientation of the proximal portions 14 and the distal end portion of the outer sheath 13.

The delivery system illustrated in FIGS. 13a-13f also includes a plurality of wire support arms 16 that may be coupled, such as rigidly and/or integrally coupled, to distal ends of the distal portions 15 of the support wires 14, 15, such as at attachment locations or points 17, 18. When the delivery system illustrated in FIGS. 13a-13f is in a fully deployed configuration, the support arms 16 may be coupled to the distal ends of the support wires 14, 15 at oblique angles so that the support arms 16 extend purely radially, in a direction transverse and perpendicular to the distal end portion of the outer sheath 13.

As illustrated in FIG. 13b, the delivery system illustrated in FIGS. 13a-13f also includes an inner sheath 7 that is located inside the outer sheath 13 and that extends around and protects at least the distal end portion of the support wires 14, 15 and the support arms 16. FIG. 13b also illustrates that a dressing 10 having a generally circular shape may be mounted to the support arms 16 and may span across a distal end portion of the delivery system. In some cases, an overall shape of the distal end portion of the delivery system may be defined by the outer, terminal ends of the support arms 16, and may have an approximately circular shape.

To assemble and prepare the delivery system of FIGS. 13a-13f for use, an operator may begin with the delivery system in the configuration illustrated in the side and end views of FIGS. 13a and 13c. The operator may then couple the dressing 10 to the support arms 16, such as at the attachment locations 17, 18, and such that the dressing 10 spans across the generally circular shape of the distal end of the delivery system in accordance with the description of such features provided elsewhere herein, as illustrated in FIG. 13d. The dressing 10, the support arms 16, and the support wires 14, 15 may then be folded up, such as so that the support wires 14, 15 extend generally linearly and the angle between their proximal portions 14 and their distal portions 15 is approximately zero, such as so that the support arms 16 are bent backwards and extend proximally, and lay flush against the distal end portions 15 of the support wires 14, 15, and such that the dressing 10 is folded up and extends distally with respect to the distal ends of the support wires 14, 15, and of the support arms 16, as illustrated in FIG. 13b.

As illustrated in FIG. 13d, the dressing may have an overall circular shape and four fold lines, each of which extends along a diameter of the circle and through the center of the circle, and which together evenly divide the circular shape into eight equal-area segments of the overall circular shape. As illustrated in FIG. 13e, as the dressing 10 folds up, the dressing 10 folds along all four of the fold lines, folding to form peaks along two perpendicular fold lines and valleys along the other two perpendicular fold lines when viewed on-end, thus, forming a shape generally resembling a four-point compass rose. As the dressing 10 folds up in this manner, the dressing 10 eventually forms four dual-layered arms that extend radially outward from a centerline of the delivery system. As illustrated in FIG. 13f, once the dressing 10 folds up in this manner, the four arms of the dressing can be wrapped in a spiral configuration about the rest of the delivery system to reduce the overall profile of the delivery system. Distal end portions of the support wires 14, 15, the support arms 16, and the dressing 10 can then be positioned within an inner sheath 7, as illustrated in FIG. 13b. Such components can then be retracted with respect to the outer sheath 13 until they are inside of, and covered and protected by, the outer sheath 13.

To use the delivery system of FIGS. 13a-13f, an operator such as a physician may insert the outer sheath 13, which may be an outer sheath of an endoscope such as a gastroscope, into a patient's body, such as through the patient's mouth and into the patient's stomach. Once the distal end of the outer sheath 13 is located at a desired position within a patient's body, such as in the patient's stomach, the operator can move the support wires 14, 15 distally with respect to the outer sheath 13. In some cases, while the operator does so, the inner sheath 7 remains stationary, and moving the support wires 14, 15 distally punctures or ruptures the distal end of the inner sheath 7 so that the distal end portion of the support wires 14, 15 and other associated components can extend distally out of both the outer sheath 13 and the inner sheath 7.

As the support wires 14, 15 move distally with respect to the outer and inner sheaths in this manner, the distal portions 15 are allowed to unfold with respect to the proximal portions 14, and the support arms 16 are released and are allowed to unfold with respect to one another within the patient's body. The operator can then view the position of such components, and of the dressing 10, through the eyepiece, and can move the support wires 14, 15 along the length of the outer sheath 13, and/or rotate the support wires 14, 15 with respect to and about the length of the outer sheath 13, so as to position the dressing 10 at a desired location, for example, such that a side of the dressing 10 lies against an internal wall of an internal lumen inside the patient's body, such as a wall of the patient's stomach. Once the dressing 10 has been desirably positioned in this manner, the operator can urge the support wires 14, 15 to press the dressing 10 against the wall of the lumen inside the patient's body, thereby causing the dressing 10 to stick to the wall in accordance with the description of such features provided elsewhere herein.

Once the dressing 10 has been pressed against the wall, the dressing 10 can be released from the support arms 16 in accordance with the description of such features provided elsewhere herein. The support wires 14, 15 can then be retracted longitudinally and proximally into the outer sheath 13. In some cases, retracting the support wires 14, 15 into the outer sheath 13 can automatically induce the support wires 14, 15, and the support arms 16 to fold up as they are pulled into the outer sheath 13 through the port. The outer sheath 13, and the endoscope or gastroscope of which it is a part, can then be retracted out of the patient, such as out of the patient's stomach through the patient's mouth.

Figure 14B:
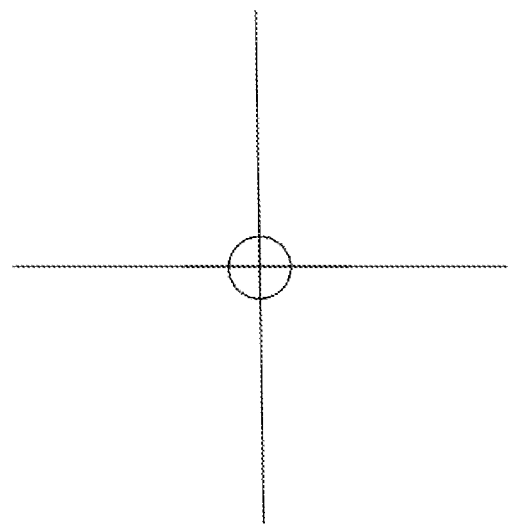
Figure 14A:
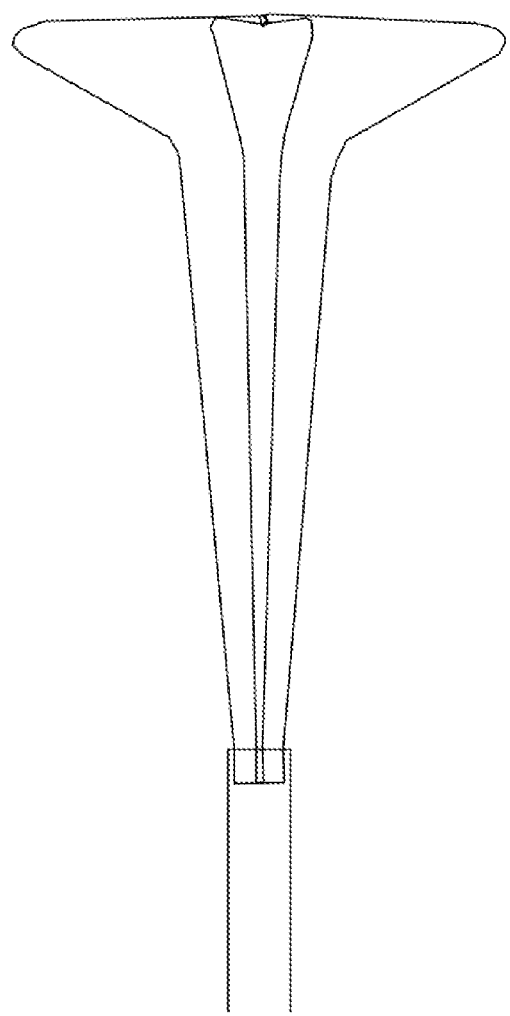
FIG. 14a provides a side view of another delivery system for a dressing for controlling gastrointestinal bleeding.
Figure 15B:
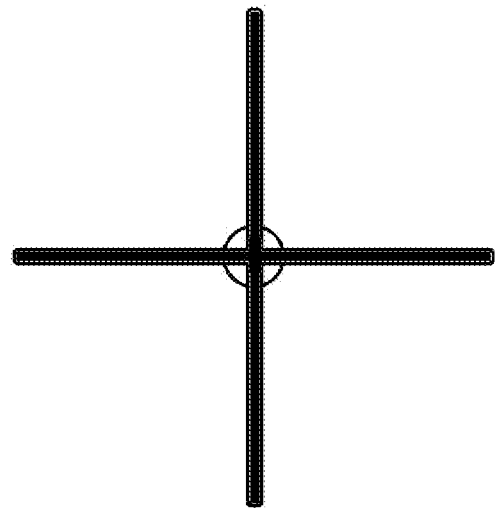
Figure 15A:
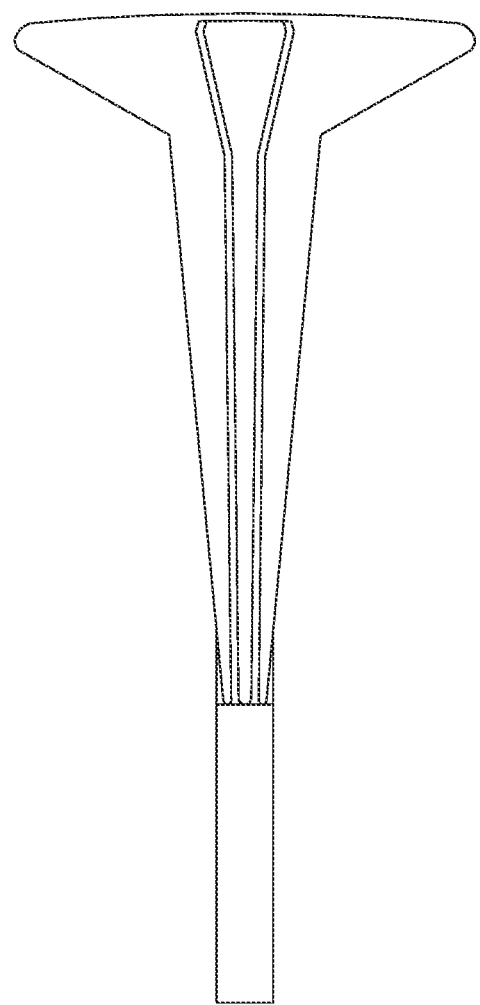
FIG. 15a provides a side view of another delivery system for a dressing for controlling gastrointestinal bleeding.

FIGS. 14a and 14b illustrate side and end views, respectively, of a wire-based delivery system similar to that illustrated in FIGS. 13a-13f, and that is operated and functions in a manner similar to that described above for the system illustrated in FIGS. 13a-13f. The delivery system of FIGS. 14a and 14b differs from that of FIGS. 13a-13f in that it includes a central interlocking loop restriction coupled to the support arms 16 (which may also be referred to as "dressing support struts") and doesn't include the tabs described above at the attachment locations 17, 18 (which may also be referred to as "wire looping of the corners"). FIGS. 15a and 15b illustrate side and end views, respectively, of another wire-based delivery system similar to those illustrated in FIGS. 13a-13f, 14a, and 14b, and that is operated and functions in a manner similar to that described above for the systems illustrated in FIGS. 13a-13f, 14a, and 14b. In some implementations, components of the delivery system illustrated in FIGS. 15a and 15b may be laser cut from larger pieces of material.

A preferred delivery system for the chitosan gastrointestinal hemostatic dressing (CGHD) comprises wire delivery (WD). In such a system, inside the delivery channel of the endoscope, the CGHD is present as a furled or folded and compacted dressing, i.e., in its compact condition, that is attached to an expandable support having a wire tip with spring memory. It is preferred that that the CGHD in its compact condition is constrained within a closely fitting, moisture resistant, thin-walled, protective tubing sheath. The closely fitting tubing sheath also provides so that the expandable support wire tip and CGHD in its compact condition are covered by the sheath and fit within and slide through the bore of the endoscope delivery channel to be delivered to a target tissue site by projecting the expandable support and dressing through and out of the distal end of tubing sheath. Preferably, the distal end of the tubing sheath is sealed with a delicate protected membrane that is ruptured on projection of the expandable support and dressing through and out of the distal end of tubing sheath. On exiting the endoscope delivery channel for application to a target tissue site, the expandable support in its unexpanded format and the dressing in its compact condition are freed from the sheath, the expandable support having spring memory that is now unconfined by the sheath and/or endoscope delivery channel, transitions into its expanding format and/or its expanded format and the dressing transitions into its transition condition and/or its splayed condition. As the wire tip expandable support springs open, the dressing, preferably a CGHD, is positioned to allow its application to the target tissue site with a pressure application of, for example, about 100 g/cm$^2$ and with an application time of, for example, up to about 30 seconds or up to about 60 seconds. On removal of the expandable support wire tip from the wound, the dressing, preferably a CGHD, is left in place and adhered uniformly to the target tissue site to provide hemostasis and wound protection.

This exemplary WD design provides an expandable support with spring wire tips in a flat or, alternatively, a circular wire profile that can be tightly folded into and unexpanded format and which can spring quickly back to an original unfolded state, or expanded format, upon release of physical constraint such as removal of the outer sheath protection and/or exit from the endoscope working channel. A secondary WD spring wire or an alternative inflated balloon pressure applicator end may be included with the primary WD to provide a cushion delivery design behind the dressing, preferably a CGHD, attached to the primary WD. That is, the secondary WD applicator "cushion" is formed either from the interconnected spring wire or inflatable balloon or bladder which springs into its inflated cushion shape on exiting the delivery tube and is used to apply uniform pressure orthogonally and centrally behind the dressing, preferably a CGHD, and primary WD upon its application to the injury. It is not depicted here, but the primary WD applicator wire delivery body connecting to the proximal end of the delivery channel is formed of a tube through which the secondary device can be passed. The secondary WD applicator may be used to detach the dressing from perforated attachment points on the primary support shaft.

Chitosan Dressing; and its Production

In certain embodiments, the chitosan dressing comprising a catechol modified chitosan, wherein the dressing is hemostatic and has a thickness that is 500 microns or less. The dressing may have a dry dressing thickness that is one of: (i) about 200 microns or less; (ii) about 100 microns or less; or (iii) about 50 microns or less. The dressing may have a density that is in the range of about 0.03 g/cm$^3$ to about 0.7 g/cm³, in the range of: (i) about 0.3 g/cm³ to about 0.4 g/cm³; (ii) about 0.4 g/cm³ to about 0.5 g/cm³, or in the range of about 0.35 g/cm³ to about 0.55 g/cm³. The dressing may be compressed. The dressing may be square, rectangular, circular, or circular petal shaped and measurements, for each of the length and width for a square or rectangular shape, may range from about 10 mm to about 50 mm, or for a circular or circular petal shape from about 10 mm to about 50 mm in diameter. In certain embodiments, the dressing measures as one of: (i) 10 mm by 10 mm; (ii) 20 mm by 20 mm; or (iii) 25 mm by 25 mm. The dressing, when dry, has a moisture content of: (1) 15% or less by weight (w/w); (2) 8% or less by weight (w/w); or (3) 4% or less by weight (w/w). The dressing may have an adhesive side and a non-adhesive side. The dressing may have an adhesive side provided on a first layer and a non-adhesive side is provided on a second layer. The adhesive side of the dressing adheres to a tissue surface when the dressing is wet. The non-adhesive side of the dressing does not adhere to a delivery device when the dressing is wet. The dressing can adhere to a gastrointestinal mucosa in 1 minute or less. The dressing can form a quaternary ammonium cation at the chitosan glucosamine C-2 amine at a tissue site. The dressing may comprise catechol oxidized to o-quinone and cross-linked in the chitosan dressing. The chitosan dressing may have a brown coloration, including a dark brown coloration. In one embodiment, the dressing may comprise catechol that is not oxidized, and wherein the chitosan dressing has a pink coloration. The dressing may comprise freeze-dried lamella. The dressing may comprise a freeze-dried structure has a thickness of 50 microns or less. The dressing may comprise a freeze-dried structure that includes more than one freeze-dried layer. The dressing may comprise spun fibers. The dressing may comprise a porous surface. The dressing may comprise a porous surface wherein the porous surface provides one or more of: (i) and absorbent surface; and (ii) channels to redirect moisture away from a target tissue surface site. The dressing may adhere to wet tissue when in a wet condition. The dressing adherence strength may be greater than or equal to about 1 kPa. The dressing resists dissolution in water, saline solution, blood, or GI fluid at about 37° C. for at least about 6 hours. The dressing can be folded or furled without cracking or tearing. The dressing may, in an open, unfurled, or unfolded condition, have an outward facing surface area that is one of about six times greater, about five times greater, or about four times greater than the outward facing surface area of that same dressing when it is in a closed, furled, or folded condition. The dressing may have a ratio of the outward facing surface area of an open, unfurled, or unfolded condition relative to a closed, furled, or folded condition that is about 15:1, or about 14:1, or about 13:1, or about 12:1, or about 11:1, or about 10:1, or about 9:1, or about 8:1, or about 7:1, or about 6:1, or about 5:1, or about 4:1, or about 3:1, or about 2:1. The dressing can be punctured or sewn without cracking or tearing. The dressing can be cross-linked. The dressing is able to be delivered intact by a balloon device, a wire device, or an endoscopic device, wherein said device may comprise a working channel having a diameter of 3.2 mm or less, and wherein the dressing is delivered through the working channel. The dressing is able to wet and adhere intact to gastric mucosa in less than 30 seconds with application of light pressure, e.g., about 200-300 g. The dressing is able to remove hydrophilic and hydrophobic biological fluids that can interfere with adhesion. The dressing is able to stay in place intact and stop moderate to oozing bleeding ranging from between about 20 ml/min to about 100 ml/min. The dressing readily detaches from a delivery device after adherence to a target tissue site. The dressing is able to resist dissolution for at least six hours after adhering to an injury site in presence of corrosive enzymes and acid environment of about pH 3. The dressing is able to seal and protect a target tissue site for at least 12 hours. The dressing is able to achieve a controlled, slow dissolution from the attachment site over a period of time not exceeding seven (7) days. The dressing is able to be folded and unfolded. The dressing is able to be furled and unfurled. The dressing is not readily soluble in water, saline solution, blood, or GI fluid at about 37° C. for at least 12 hours following application. The dressing is not readily soluble in water, saline solution, blood, or GI fluid at about 37° C. for at least 24 hours following application. The dressing does not adhere to a delivery device. The dressing does not does not increase or decrease in size by more than about 25% in length and width, or more than about 50% in thickness in the presence of water, saline solution, blood, or GI fluid at about 37° C. The dressing comprises an adhesive side that interacts with an injury site, and wherein the chitosan dressing comprises a non-adhesive side that interacts with one of a delivery device or the adhesive side when the dressing is in a dry and folded or a dry and furled condition. The dressing is capable of being terminally sterilized without affecting dressing characteristics. The chitosan dressing is capable of being stored under controlled conditions over time without affecting dressing characteristics.

In some embodiments, the dressing can be used for treatment of a disease, condition, disorder, trauma, or injury. For example, the use of the dressing in the treatment of a disease, condition, disorder, trauma, or injury, comprising directly adhering the dressing at an injury site upon wetting, and applying pressure to the dressing for about 30 seconds. The dressing for use in treatment of a disease, condition, disorder, trauma, or injury, may remove hydrophilic and hydrophobic biological fluids upon adherence. The dressing for use in treatment of a disease, condition, disorder, trauma, or injury, may comprise leaving the dressing in place at a target tissue site and the dressing may remain at the target tissue site for at least 24 hours. The dressing for use in treatment of a disease, condition, disorder, trauma, or injury, may be capable of slow dissolution at the target tissue site and dissolves completely without human intervention in seven days or less.

In some embodiments, the invention disclosed herein comprises methods of producing the chitosan dressing. In one embodiment, the method comprises: performing synthesis with chitosan and catechol in an aqueous reaction solution; maintaining a pH of the reaction solution at or below pH 5.5; increasing the pH of the reaction solution, and controlling oxygen exposure to the reaction solution, to provide catechol oxidation and cross-linking; and drying the reaction solution. In certain embodiments, the methods do not comprise an intermediate drying step between step. In certain embodiments, the methods comprise increasing the pH of the reaction solution from about 5.8 to about 6.2. Another embodiment of a method of producing the chitosan dressing comprises a method of producing a chitosan dressing comprising: freeze-drying a first aqueous solution comprising chitosan; freeze-drying a second aqueous solution comprising chitosan; obtaining a low-density chitosan dressing with inter-connected porous structure from each of the above steps; and compressing the low-density chitosan dressing from each of steps; and preparing a two-layer chitosan dressing from the compressed low-density chitosan dressing. In certain embodiments, the low-density chitosan dressings from each of above-mentioned freeze-drying steps are combined prior to compression. In certain embodiments, the compressing of step may occur at temperature ranging from about 20° C. to about 150° C. In certain embodiments, the dressing is dried to a moisture content of less than about 15% (w/w).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/612,000 filed on Dec. 29, 2017, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

Example 1

In the development of the chitosan gastrointestinal hemostatic dressing (CGHD) of the invention different prototype dressing compositions were investigated to prepare foldable, mucoadhesive and cohesive chitosan dressings with sustained hemostatic efficacy at pH close to 4. Such thin high-surface area hemostatic dressings which are uniquely well-suited for use in extreme physiological environments, including (but not limited to) the stomach and other parts of the GI tract, and capable of delivery using minimally invasive techniques due to their small volume relative to strength and treatment surface area capacity, have not been previously described. There is an urgent need for such dressings. The CGHD dressings disclosed herein defied conventional expectations as to what may be expected from, or achieved using, chitosan based materials to form hemostatic, thin, high surface area, low volume, foldable, strong, low pH dissolution resistant, adherent, biocompatible dressings.

CGHD formulations were assessed in vitro for long-term, mechanical resilience, ability to be delivered, low pH/wet adherence, hemostatic ability and ability to be left in place, and to be digested or dissolved in less than 168 hours, or one week (7 days). Prototypes were screened in an acute stomach injury model before down selection to best performing dressings for ≥3 hour application control of non-variceal upper gastrointestinal bleeding (UGIB). In vivo swine models of gastric arterial bleeding were used to assess acute and prolonged (≥3 hours) control of brisk (class 2A) non-variceal UGIB.

The following materials were used in the gastrointestinal chitosan hemostatic dressing development:
Chitosan A: Primex ChitoClear 65010, TM 4375, MW=250-300 kDa, Brookfield viscosity in 1.0% w/w chitosan solution in 1.0% acetic acid at 25° C. and spindle LV1=390 cPs, DDA=80% (by colloidal titration).
Chitosan B: Primex ChitoClear 43000, TM 4167, MW=110-150 kDa, Brookfield viscosity in 1.0% w/w chitosan solution in 1.0% acetic acid at 25° C. and spindle LV1=9 cPs, DDA=95% (by colloidal titration).
Glacial acetic acid: Fisher Scientific, Catalog No. A38-212.
Hydrochloric acid: 1.0 M aqueous solution Sigma Aldrich, Catalog No. H9892.
L-Lactic acid: JT Baker, Catalog No. 0196-01.
Glycolic acid: JT Baker, Catalog No. M821-05.
Sodium hydroxide: 5.0 M NaOH aqueous solution Sigma Aldrich, Catalog No. 58263-150 ml.
Potassium hydroxide: 0.1 M KOH in methanol (BDH).
Ethanol: 200° Proof Sigma Aldrich, Catalog No. 459844-1L.
Microfiber chitin: ~10 micron diameter of aspect ratio ~100/1 of 100% acetylated. Weifang
Centrifugal spun chitosan nanofiber Lot G01 of basis weight 12 g/m$^2$
Tricol Medical Grade non-woven microfiber.
De-ionized water: Ricca ACS Reagent Grade deionized water, Catalog No. 9152-5.
Acetic anhydride: ACS reagent grade obtained from Sigman Aldrich, Catalog No. 320102-1L.
3,4-dihydroxyhydrocinnamic acid (Mw=182.17 g/mo): 98% Sigma Aldrich, Catalog No. 102601.
1-ethyl-3-(-3-dimethylamino-propyl)-carbodiimide: (alternatively N-(3-dimethylaminopropyl)-N'-ethylcarbodiimide hydrochloride with common acronym EDC) Sigma Aldrich, Cat. #E7750.
Sodium Chloride: Sigma Aldrich, Catalog No. 793566-500g.
Synthetic gastric solution: Pepsin—Sigma Aldrich P7000-25G, NaCl—Sigma Aldrich 793566-500G, H$_2$O ACS Reagent grade, NaOH—Sigma Aldrich, Catalog No. S8263-150 ml.
Tissue: fresh swine bladder mucosa, fresh swine stomach mucosa from Animal Biotech Industries Inc.
Citrated bovine whole blood: Lampire Biological Laboratory Bovine CPD, Catalog No. 7720010.
Cynaoacrylate: Permabond 910 Tissue Adhesive, Catalog No. 72590.
Dialysis Tubing: 3,500 Da MWCO Snakeskin Dialysis Tubing (Fisher Scientific), Cat. #PI88244.
Pectin: MP Biomedicals LLC, Catalog No. 102587.
Glycerol: Sigma Aldrich, Catalog No. G-8773.
Polyethylene glycol: Spectrum, Catalog No. P0108.
Polyethylene oxide: Mw 400,000 da, Sigma Aldrich Catalog No. 372773-500G.
Poloxamer 407: Spectrum, Catalog No. P1166.
Guar: Sigma Aldrich, Catalog No. G4129.
Cellulose (microcrystalline powder): Sigma Aldrich, Catalog No. 435236.
Polyacrylic acid: My 1,250,000 Sigma Aldrich, Catalog No. 306215-100G.
HemCon Patch® Pro, highly effective commercial chitosan hemostatic dressings, were used as positive control dressing in acute hemostatic studies.
Standard surgical gauze was used as a negative control in acute hemostatic studies.

Preparation of Catechol Chitosan and Characterization
Approach 1.

Chitosan A (9.0 g) was dissolved in deionized water (148 g) and HCl (28 ml, 1.0 M HCl). A 1:1 (150 ml) solution of water:ethanol was prepared. 3,4-dihydroxyhydrocinnamic acid (25.9 mmol) and N-(3-dimethylaminopropyl)-N'-ethyl-carbodiimide hydrochloride (51.8 mmol) were dissolved in the water/alcohol solution. The water/alcohol solution was added to the chitosan solution. The solutions were vigorously mixed. The reaction mixture was controlled to pH 5.4 using dropwise addition of 0.1 M HCl and 0.1 NaOH solution and left to react with overhead stirring for at least 12 hours. Following this, the chitosan solution (~300 ml) was dialyzed against 5 liters of water acidified with 1 drop of 1.0 M HCl solution for six days and against non-acidified water for at least 3 hours. Dialysate was changed at –24 hour intervals throughout the duration of the dialysis with at least 5 changes of water.

Approach 2

Chitosan A (1.5 g) was dissolved in water (140 g) and HCl (5 ml, 1.0M HCl). A 1:1 solution (145 ml) of water:ethanol was prepared. 3,4-dihydroxyhydrocinnamic acid (10.5 mmol) and N-(3-dimethylaminopropyl)-N'-ethylcarbodiimide hydrochloride (13.0 mmol) were dissolved in the water/alcohol solution. The water/alcohol solution was slowly added to the chitosan solution and the reaction mixture was stirred with an overhead mechanical stirrer at low stirrer speed. The reaction mixture was controlled to pH 5.5 using dropwise addition of 0.1 M NaOH and 0.1 M NaOH solution and left to react for ~12 hours under stirring. After the reaction process, the solution was dialyzed as described in approach 1.

Approach 3

Chitosan A (9.0 g) was dissolved in water (126 g) acidified with HCl (30 ml, 1.0M). A 1:1 solution (150 ml) of water:ethanol was prepared with N-(3-dimethylaminopropyl)-N'-ethylcarbodiimide hydrochloride (31.3 mmol) dissolved in the water/alcohol solution. Following this, 3,4-dihydroxyhydrocinnamic acid (15.7 mmol) was dissolved in 15 ml of water and this solution was added slowly to the chitosan solution under moderate overhead mechanically stirring. The water/alcohol solution containing the N-(3-dimethylaminopropyl)-N'-ethylcarbodiimide hydrochloride was slowly added to the chitosan solution and the reaction mixture was stirred with an overhead mechanical stirrer at low stirrer speed. The reaction mixture was controlled to pH 5.5 using dropwise addition of 0.1 M KOH (in methanol solution) and 0.1 M HCl solution and left to react for ~12 hours under stirring. After the reaction process, the solution was dialyzed as described in approach 1.

Approach 4

Chitosan A (9.0 g) was dissolved in water (126 g) acidified with HCl (30 ml, 1.0M). The solution was then adjusted to near pH 5.1 using 0.1 M HCl and 0.1 M NaOH aqueous solution. A 1:1 solution (150 ml) of water:ethanol was prepared with N-(3-dimethylaminopropyl)-N'-ethylcarbodiimide hydrochloride (31.3 mmol) dissolved in the water/alcohol solution. Following this, 3,4-dihydroxyhydrocinnamic acid (15.7 mmol) was dissolved in 15 ml of water and this solution was added slowly to the chitosan solution under moderate overhead mechanically stirring. The water/alcohol solution containing the N-(3-dimethylaminopropyl)-N'-ethylcarbodiimide hydrochloride was slowly added to the chitosan solution and the reaction mixture was stirred with an overhead mechanical stirrer at low stirrer speed. The reaction mixture was controlled to pH 5.0 using dropwise addition of 0.1 M KOH (in methanol solution) and 0.1 M HCl solution and left to react for ~12 hours under stirring. After the reaction process, the solution was dialyzed as described in approach 1.

Degree of Substitution of Catechol Chitosan

Quartz UV test cells, 1 cm path length, ×2 (HACH Co., cat #48228-00) were used in acquiring UV/vis spectra. The UV/Vis spectrophotometer was a Varian Cary Bio 100.

Standard solutions of 3,4-dihydroxyhydrocinnamic acid were prepared in water and absorbance at 280 nm was plotted against concentration. The extinction coefficient $\varepsilon$ in the Beer Lambert relationship shown below for absorbance in dilute solution $$A = \varepsilon \cdot c \cdot l$$

A is absorbance (dimensionless) and l is the path length (Absorbance <0.5) was determined as 2,540±50 liter/(mol·cm). This value was used to determine degree of substitution in the modified chitosan in dilute aqueous solution of known mass of modified chitosan, known volume of solution and measured peak absorbance at 280 nm.

The chitosan catechol solution is diluted so that its absorbance at 280 nm is less than 0.5 (usually about 1:50 or 1:100). The absorbance, the weight of the solution used in the dilution, and the percent solids (CS-catechol) were used to find the fractional degree of substitution ($f_{DS}$) of the HCA with respect to free amines on the chitosan backbone according to the equations:—

$$f_{DS} = \frac{n_{HCA}}{F_{DDA} \cdot n_{total\ Chitosan\ mers}}$$

$$f_{DS} = \frac{A \cdot V \cdot \{(f_{DDa} \cdot 161) + (1 - f_{DDA} \cdot 203)\}}{\varepsilon \cdot l \cdot \left\{m_{cc} - \left(\frac{A \cdot V}{\varepsilon \cdot l} \cdot 165.17\right)\right\} \cdot f_{DDA}}$$

where A is UV/vis absorbance at 280 nm of the modified chitosan; V is the volume (liters) of the modified chitosan solution taken to dry to constant dry mass; $m_{CC}$ is the measured dry mass (g) of the catechol modified chitosan; $f_{DDA}$ is the fractional degree of deacetylation of the chitosan.

Results

The chitosan-catechol syntheses yielded 50-300 mL of chitosan catechol solution that ranged from milky to clear, light pink to brown, and with viscosity ranging from thin liquid consistency (e.g. water near 1 cps viscosity) to thick liquid consistency (e.g. honey: viscosity >100,000 cps). The synthetic results (see Table 1) were dependent on the initial concentration of chitosan, avoidance of precipitation of chitosan in the pH adjustment step from near pH 2 to pH 5, maintenance of pH near 5.0 to 5.5 during reaction, and thorough removal of low molecular weight components in the dialysis washing step.

TABLE 1

Summary of Characterization Results

| Cs-Cat Approach | Percent Solids (w/w)¶ | Percent Substitution |
|---|---|---|
| 1 | 0.72 ± 0.1 | 17.2 ± 2 |
| 2 | 0.42 ± 0.1 | 132* |
| 3 concentrated† | 0.63 ± 0.1 | 29.0 ± 3 |
| 4 concentrated† | 1.80 ± 0.1 | 26.4 ± 3 |

¶Percentage dry solid in the solution was determined gravimetrically
*Synthesis in approach 2 resulted in excessive Uv/vis absorbance in determination of degree of substitution
†Catechol chitosan was concentrated by heat assisted drying removal of water from the solution suspended within its dialysis membrane.

Example 2

Freeze Phase Separated Hydrophilic Polymer Dressings

Hydrophilic polymer aqueous solutions were prepared inside 500 ml, 1000 ml or 2000 ml Nalgene LDPE bottles or polypropylene beakers by addition of components including, but not limited to, pre-prepared solution, hydrophilic polymer, water, acid, and additional components. FIGS. 8A-8B list formulation approaches, hydrophilic polymers, and % w/w of solution hydrophilic polymer components. Some of the formulations in FIGS. 8A-8B do not contain chitosan. Formulation strategies are listed in FIGS. 8A-8B as A, B, C, D, E, F, and G. Strategy A was primarily as a control of materials such as chitosan which were expected not to resist dissolution in the stomach as tested by in vitro simulated gastrointestinal fluid. Reacetylation (Strategy B) was one of the proposed strategies to reduce rate of dissolution/degradation until in vitro simulated gastrointestinal fluid testing in the presence of pepsin demonstrated faster rate of degradation and dissolution of chitosan with lower degree of deacetylation. Strategy C was investigation of compositions of known polysaccharides (guar, pectin and starch) without chitosan which resist in vitro simulated gastrointestinal fluid digestion. Strategy D was strategy C with chitosan and possibly other hydrophilic polymers. Strategy E was use of catechol modified chitosan as the only hydrophilic polymer. Strategy F was use of catechol modified chitosan with other hydrophilic polymers. Strategy G was use of a centrifugal spun chitosan fiber.

The main problems experienced when formulating for the gastrointestinal hemostatic dressing application were: (1) unexpected and rapid (<10 mins) pepsin promoted degradation of chitin and chitosan in synthetic gastric fluid, wherein pepsin promoted a rate of chitosan degradation at increasing rates corresponding with lower degrees of deacetylation; (2) unexpected interference from blood in achieving adherence with the pure catechol modified chitosans; (3) susceptibility in dressing cracking and tearing when making changes to formulations to address other problems.

The final hydrophilic polymer solution % w/w was between 0.1% to 4% polymer. Capped bottles and their contents were mixed continuously at room temperature over 12 to 24 hours to achieve full solution homogeneity using IKA KS260 orbital shaker or a Wheaton bench top bottle roller. Beaker solutions were mixed on a magnetic stirrer plate with magnetic stirrer bead at room temperature for 12 to 24 hours to achieve solution homogeneity. Parafilm was used to close the beaker from the external environment during mixing. The solutions prepared for freeze phase separation were substantially homogeneous and clear when suspension conditions were not present (exceptions with A06, B02, B04 and C05). The catechol chitosan solutions demonstrated some haze and milky appearance indicating presence of some dispersed fine catechol chitosan globular particles.

Except in the case of Strategy G, chitosan solutions were prepared as freeze phase separated dressings with final solution % weight of hydrophilic polymer in the range 0.25% to 4% w/w aqueous solution. Freeze phase separation was performed in Teflon coated aluminum mold wells with horizontal flat bases. The solutions were poured into the wells to a height from the mold base of preferably not more than about 10 mm, more preferably 2.5 mm and most preferably 5.0 mm. The solutions initially at a temperature in the molds before freezing between 15° C. and 30° C. were then frozen by application of cooling through the base of the molds. Although other cooling temperatures may be applied to achieve suitable freeze phase separated structure, preferably the applied cooling temperature of the shelf was −40° C., more preferably the cooling temperature was −55° C. and most preferably the cooling temperature was −45° C. After the solution achieved freezing phase separation and the temperature of the frozen solution equilibrated at the freezing temperature, the system was allowed to further freeze phase separate and equilibrate for at least an additional hour before drying. In a modified freezing and mold filling method to accommodate layers of different freeze phase separated solutions, a first layer was added to the mold to a preferred depth and frozen, a second layer was then added and frozen, a multi-layered freeze phase separated dressing could be prepared in this manner. Care was needed to ensure there was no frost between an (n−1)th frozen and nth poured solution and differences in layer frozen structure could result in cracking. The discovery of the successful method of layering and adhering of single layer previously freeze dried hydrophilic polymer matrices to a single co-adhered compressed multilayered composite sheet during this investigation was an unexpected and significant finding. It is also possible to combine separately prepared freeze dried compositions using compression.

A 24 square foot shelf Virtis Benchmark 2000 pilot scale freeze dryer was used for sublimation freeze drying of the freeze phase separated frozen solution plaques. In the primary freeze drying (removal of ice not hydrogen bonded to the hydrophilic polymers), the equilibrated frozen plaques in their molds were subjected to reduction in pressure ≤300 mTorr within the freeze dryer, the freeze dryer condenser was set to ≤−65° C. and the freeze dryer shelves were heated to promote sublimation of the ice from the freeze separated plaques without increasing plaque temperature above −15° C. After removal of substantially all the non-bonded ice, the shelf temperature was raised to near 25° C. for removal of the hydrogen bonded ice and reduction of moisture content in the dried dressing to not more than about 4% residual water in the dried dressing. Final dried matrices conformed to the original shape of the filled mold with close to 5% shrinkage in length and width and density between 0.005 g/cm$^3$ and 0.04 g/cm$^3$. They contained void space of more than 95% and they were interconnected porous structure (e.g., 20-300 micron) with fine polymer lamella (e.g., submicron to 5 micron thickness) and pore spacing between adjacent lamella of, for example, 20 microns to 300 microns.

After freeze phase separation and drying, the dried matrices were compressed from their original thicknesses (10 mm to 2.5 mm) to a final thickness preferably near 50 microns. If two uncompressed dressings were compressed one on top of the other then they would be permanently bonded together at the conclusion of the compression process. Calibrated uniform thickness thin shims may be used in the compression to achieve a desired thickness of compressed dressing substantially the same thickness as the shim. There are a number of ways to achieve this compression with a desired compression set near 50 microns. The preferred compression method used in the investigation was compression of the whole dried uncompressed dressing (dimensions typically close to 100 mm long×100 mm wide×2.5 mm high or 50 mm diameter×2.5 mm high) with uniaxial compression rate at ≤10 mm/min, or about ≤0.5 mm/min, to ≤100 microns thickness between aligned platens. While lower compression rates lead to better mechanical properties of the final dressings, dressings prepared with initial compression rates near, for example, about 10 mm/min are acceptable. The platens (Teflon coated Mic 6 Aluminum 300 mm×300 mm×90 mm) were machined to flat planar faces (≤5 microns in 300 mm). The temperature of platens during compression was maintained preferably near 80° C. over 3 to 5 minutes of uniaxial compression. Compression was achieved by screw loading at the four corners of the platens at up to four tonnes (tonnes meaning 1000 kilograms) loading at each corner. Compression was held for at least 2 minutes before release of load. The novel compressed hydrophilic polymer matrices were measured for compression thickness and weight. Final densities were between 0.35 and 0.55 g/cm³. After compression, the dressings were further processed. This additional processing included die cutting into 2.5 cm diameter test pieces and in some cases thermal annealing heat treatment (heated in a convection oven at 60° C. to 150° C. for 5-30 minutes). At the conclusion of processing the dressings were placed in foil pouches with thermal sealing. Packaged dressings intended for animal and biocompatibility testing were gamma-irradiated at 25 kGy.

Example 3

In Vitro Testing of Gastrointestinal Hemostatic Dressing Prototypes

Synthetic Gastric fluid preparation: Pepsin (1.6 g), NaCl (1 g), water (500 ml) was added to a Nalgene LDPE 1000 ml bottle and mixed. The acidity was adjusted to be between pH 3 to 4 using Millipore pH 0-14 universal indicator strips and dropwise addition of 3.0 M HCl. Dropwise addition of 1.0 M NaOH was used to raise the pH if required.

1. Test Tube Method

For rapid screening of test article resistance to dissolution/fragmentation in synthetic gastric fluid, a 0.5 cm×0.5 cm piece of test article sheet was added to the base of a labeled 15 ml Falcon tube and 5 ml of gastric fluid was added to the tube before capping and placing upright in an incubator at 37° C. with gentle shaking. The tube was monitored until demonstrable dissolution/fragmentation of the sample was observed and the time to dissolution/fragmentation was recorded. The results of test tube testing are provided in FIGS. 6A-6C.

2. Beaker Method

For materials showing resistance in the test tube test, a modified test method was developed whereby a 38 mm×38 mm piece of fresh stomach mucosa was adhered inside a polystyrene beaker (250 ml, Fisher Catalog No. 08-732-124) at its base using a thin layer of cyanoacrylate adhesive applied using a cotton swab. The mucosa surface prior to gluing was dabbed dry using Texwipe tissue. The adhesive was allowed to dry over 2-5 minutes. After becoming fully adhered to the beaker, the top exposed tissue surface was wetted drop-wise (generally 2 drops) with citrated whole bovine blood, and a 20 mm×20 mm piece from a test article sheet was adhered to the blood covered mucosa surface by application of 500 g of load applied orthogonally to the mucosa surface for 1 minute through a 25 mm diameter PVC flat head probe. Synthetic gastric fluid at room (~90 ml) was added to the beaker. Parafilm was used to seal the beaker and the beaker was placed upright on an IKA KS260 orbital shaker in an incubator at 37° C. under mild shaking (130 rpm). The inside of the beaker was monitored at minutes and then hourly until demonstrable separation from mucosa and/or dissolution/fragmentation of the sample was observed and the time to separation/dissolution/fragmentation was recorded.

During test method development, the load applied (up to 5 kg) and time of application for attachment was up to 5 minutes. In comparison to minimally invasive in vivo application the gastrointestinal surgery team advised that an application not be more than 300 g load applied uniformly over a 2.5 cm diameter dressing for not more than 30 seconds. The original conditions of 5 kg and 120 seconds were modified to 500 g for 1 minute. The application of 300 g load for 30 seconds application is now applied. Results of beaker testing are provided in FIGS. 6A-6C.

3. Mechanical Fold Testing

Sample sheets were folded 180° along length and width axes and the crease line was compressed. Dry test sheets (25 mm×25 mm) were folded and unfolded and observation of resistance to tearing and cracking was recorded. Results of fold testing are provided in FIGS. 6A-6C.

4. Mechanical Tissue Adherence

A uniaxial mechanical tester (Instron Model 5844) with 10 N load cell was used to investigate wet adhesion to mucosa. Adhesion testing was performed using ASTM F2258-03 "Standard Test Method for Strength: Properties of Tissue Adhesives in Tension". Testing was performed with a testing configuration with lower and upper PVC probes uni-axially aligned in the z vertical direction so that the edges of their x-y horizontal, 15.2 mm diameter faces would accurately (±0.2 mm) coincide with each other with uniaxial lowering of the top probe which was supported on the upper, movable Instron crosshead in chuck fixture. The lower PVC probe was supported in a stationary, bottom, chuck fixture. The bottom PVC horizontal surface was used to support a 10 mm×10 mm mucosal tissue sample adhered at least 5 minutes before testing by cyanoacrylate glue to the PVC surface. The top PVC horizontal surface was used to support a 10 mm×10 mm CGHD test piece that was adhered by a 3M double side tape at least 5 minutes before testing. The square tissue piece was wetted with 0.25 ml of the de-citrated bovine whole blood CPD prior to lowering the probe onto the test surface. The probe was lowered at 10 mm/min until a maximum load of 0.98 N was reached. At contact, the test and tissue pieces contacted accurately (±0.2 mm) and were mutually co-planar. The uniaxial probe load at 0.98 N was maintained for 30 seconds after which the probe was removed at 10 mm/min and maximum failure stress was recorded. The results of adherence testing are shown in Table 2.

TABLE 2

| Probe Adherence Results | | |
|---|---|---|
| G01-Nanospun CS (6-layer) (kPa) | F11-25% CS-cat, 22-1 conc'd/2% CS AcOH soln (kPa) | PVC Probe (No Dressing) (kPa) |
| 1 | 0.86 | 2.07 | 0.30 |
| 2 | 1.47 | 3.53 | 0.26 |
| 3 | 2.13 | 4.46 | 0.08 |
| 4 | 1.82 | 6.82 | 0.25 |
| 5 | 0.92 | 3.69 | |
| Mean | 1.44 | 4.11 | 0.22 |
| Std. Dev. | 0.55 | 1.74 | 0.10 |

Example 4

In Vivo (Swine Model of Upper Gastrointestinal Bleeding) Screening Study Animals A total of 4 crossbred adult domestic swine, body weight from 40 to 50 kilograms, were used in this study.

All experiments were performed in accordance with the 2011 National Research Council, "Guide for the Care and Use of Laboratory Animal" and applicable federal regulations. The protocol for the animal is in accordance with the NIH Guidelines for the Care and Use of Laboratory Animals and was approved by the Institutional Animal Care and Use Committee. All procedures and care of the animals were performed at the approved animal research facility.

Veterinary staff inspected all of the animals to ensure baseline health. Animals were removed from all bedding 72 hours prior to the procedure and not permitted food 24 hours prior to surgery. Animals were allowed to drink water ad libitum. Twenty minutes prior to the procedure, the animals were given 500 mg of intravenous Cefotetan and a 250 ml fluid bolus of Ringer's Lactate. After premedication with glycopyrrolate and a combination of tiletamine HCl and zolazepam HCl (Telazol®, Fort Dodge Laboratories, Fort Dodge, Iowa), anesthesia was induced by mask using 5% isoflurane. The swine was intubated, placed on a ventilator, and maintained with 2-3% isoflurane with endotracheal intubation. The right femoral artery was surgically isolated and cannulated with a 6 Fr catheter to facilitate continuous blood pressure monitoring and retrieval of blood for laboratory studies. To induce a state of coagulopathy, 5000 units of heparin, was given intravenously (IV). A continuous infusion of heparin of 50 units/kg was used during the procedure to maintain anticoagulation. An activated clotting time (ACT) level was tested after 10 minutes and then every 20 minutes during the procedure with additional heparin (50% of the original dose, 2500 units) given IV as needed to maintain ACT>250 seconds anticoagulation. ECG, blood pressure, and oxygen saturation were monitored during surgery and recovery. Vitals including blood pressure, % isoflurane, O2 flow, respiratory rate, heart rate, SpO2, capillary refill time, blood pressure and mean arterial pressure, and body temperature were recorded every 15 minutes.

At the completion of the experiment, while under anesthesia, the animals were euthanized with IV administration of Euthasol (1 mg/10 lbs). Death was confirmed by flat-wave ECG and absence of heart beat by stethoscope.

Gastric Bleeding Model

The swine were prepared using Chlorhexadine and draped in a sterile fashion. A midline laparotomy was performed to expose the stomach. A 5-cm segment of the gastroepiploic vessels were dissected free from the gastric wall. For each segment, a 1-cm gastrotomy was made adjacent to the free but intact blood vessels. The artery was then pushed through the gastrotomy and positioned so that it is exposed to the gastric lumen. The gastric incision was then closed in a standard manner along with the abdominal wall. An upper endoscopy (GIF Type Q180, Olympus) was performed to identify the gastric wound site in the stomach. The wound site and gastric vessels were then located and incised with an endoscopic biopsy forceps to create a pulsatile bleeding.

The chitosan gastrointestinal hemostatic dressings (CGHD) identified in Table 3, below, were applied with manual application by hand. In brief, an approximate 12 cm incision was made on anterior gastric wall to expose gastric cavity and to apply the CGHD prototype dressing (20 mm×20 mm) on the gastric bleeding site. Before dressing application, bleed rate was determined using dry pre-weighed folded gauze sponges to absorb any blood from the wound over a 15 second period and weighed, multiplied ×4 to calculate bleed rate (weight of blood) per minute. The CGHD dressing was placed over the wound with a gauze sponge on top. Manual pressure is applied evenly with light pressure near 200-300 g over the patch for 30 seconds, with a local pressure in the vicinity of 100 g/cm$^2$ or near 10 Kpa (assuming application over the center of a 4 cm$^2$ patch) (use of units of mass, such as grams, in this and in similar contexts herein, means a pressure corresponding to the weight of the recited mass evenly distributed over the area of the patch). At 30 seconds the gauze was removed and the area was observed for initial hemostasis and followed for signs of rebleeding for up to 10 minutes. At completion of application, the CGHD dressing was removed and dressing tissue adherence was ranked according to an adherence score in accordance to how the dressing adhered to tissue surface using the Adherence Score System (Table 3).

TABLE 3

Adherence Score

| Score | Description |
|---|---|
| 0 | No adherence |
| 1 | Little adherence |
| 2 | Moderate adherence |
| 3 | Moderate to strong adherence |
| 4 | Strong adherence |

Results

| | | Gastric Vascular Injury | | |
|---|---|---|---|---|
| Type of Dressing | Code # | Bleed rate (g/min) | Hemostasis Rate (%) | Adhesion score |
| 4Ch01.Pect | D24 | 8 | 70% | 2 |
| ChCatechol | E1 and E2 | NA | 29% | 2.5 |
| 0.25Cat1.5Ch | F11 | NA | 63% | 2 |
| 0.75Cat0.5Ch | F12 | NA | 50% | 1.5 |
| Nanofiber 12GSM | G01 | 5 | 67% | 1 |
| Patch Pro | H01 | NA | 100% | 3.5 |
| Gauze | H02 | 13 | 33% | 0 |

Three CGHD family prototypes (D24, F11, and G01) demonstrated good hemostatic properties in terms of immediate hemostasis and acceptable adhesion scores in the gastric vascular injury model. Slow wound tissue adherence for pure catechol modified chitosan was addressed by combination of unmodified chitosan with the catechol chitosan. Final heat treatment of these compressed freeze phase separated dressings for 15 minutes to 30 minutes at close to 80° C. resulted in dressings with good immediate tissue adherence and thus promising hemostatic performance in rapidly controlling pulsatile hemorrhagic gastrointestinal bleeding with short (30 seconds) low pressure applications. It is noted that the Patch Pro is not suitable for use in the gastroscope delivery as it cannot be folded as required and is too thick. Also, the Patch Pro is formed of standard chitosan which is degraded in about 15 minutes or less in the upper GI.

Example 5

In Vivo (Swine Model of Upper Gastrointestinal Bleeding) 3 Hour Study Animals

A total of 4 crossbred adult domestic swine, body weight from 40 to 50 kilograms, were used in this study.

Animal preparation, surgical preparations, animal anesthesia and animal sacrifice were the same as presented in Example 4.

Gastric Bleeding Model

Figure 2:
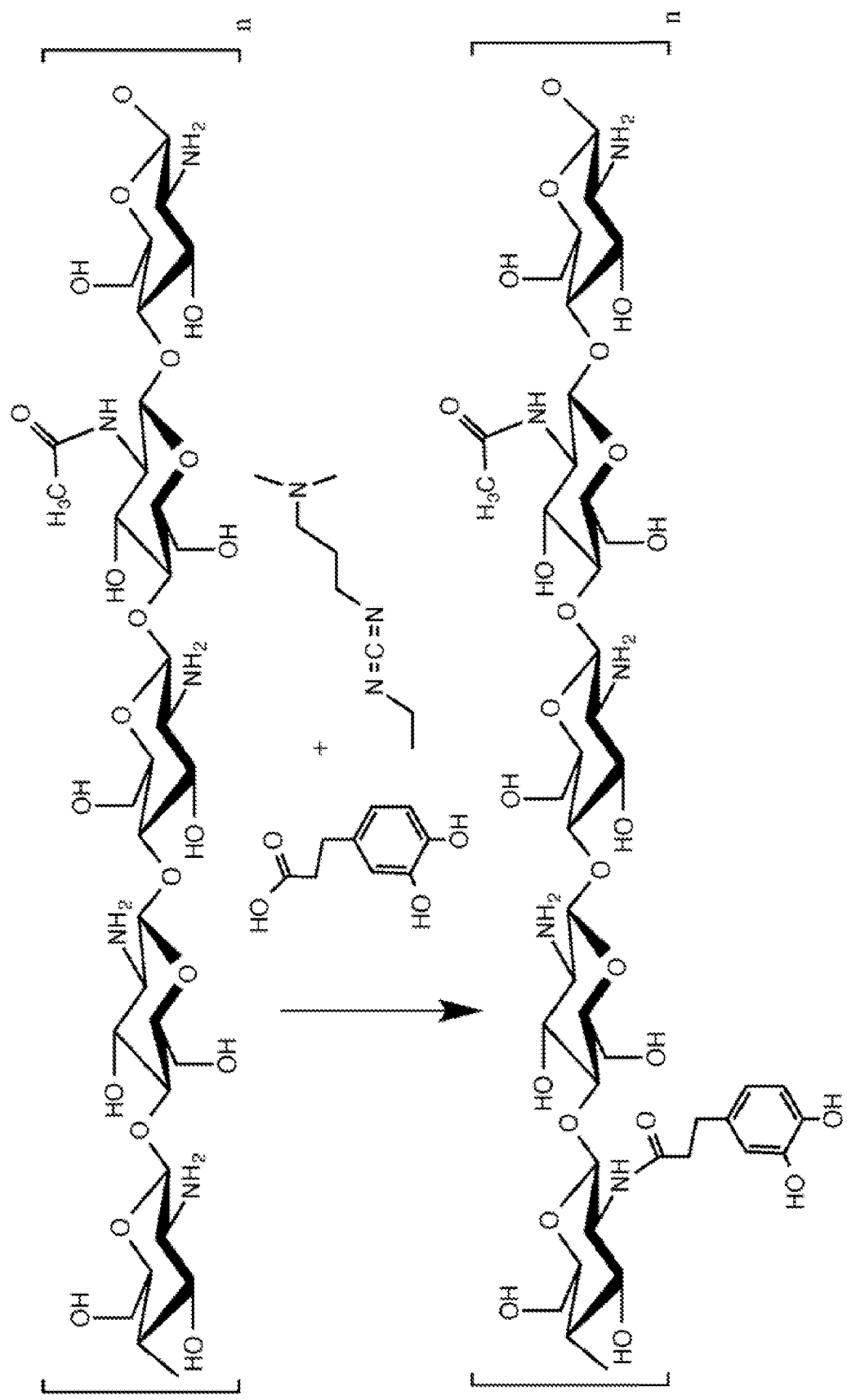
FIG. 2 depicts an N-acylation addition reaction in the presence of 1-ethyl-3-(-3-dimethylamino-propyl)-carbodiimide (EDC) where 3,4-dihydroxyhydrocinnamic is covalently attached to a chitosan C-2 amine with a degree of substitution of 25% in aqueous solution at pH 5.5.
Figure 4:
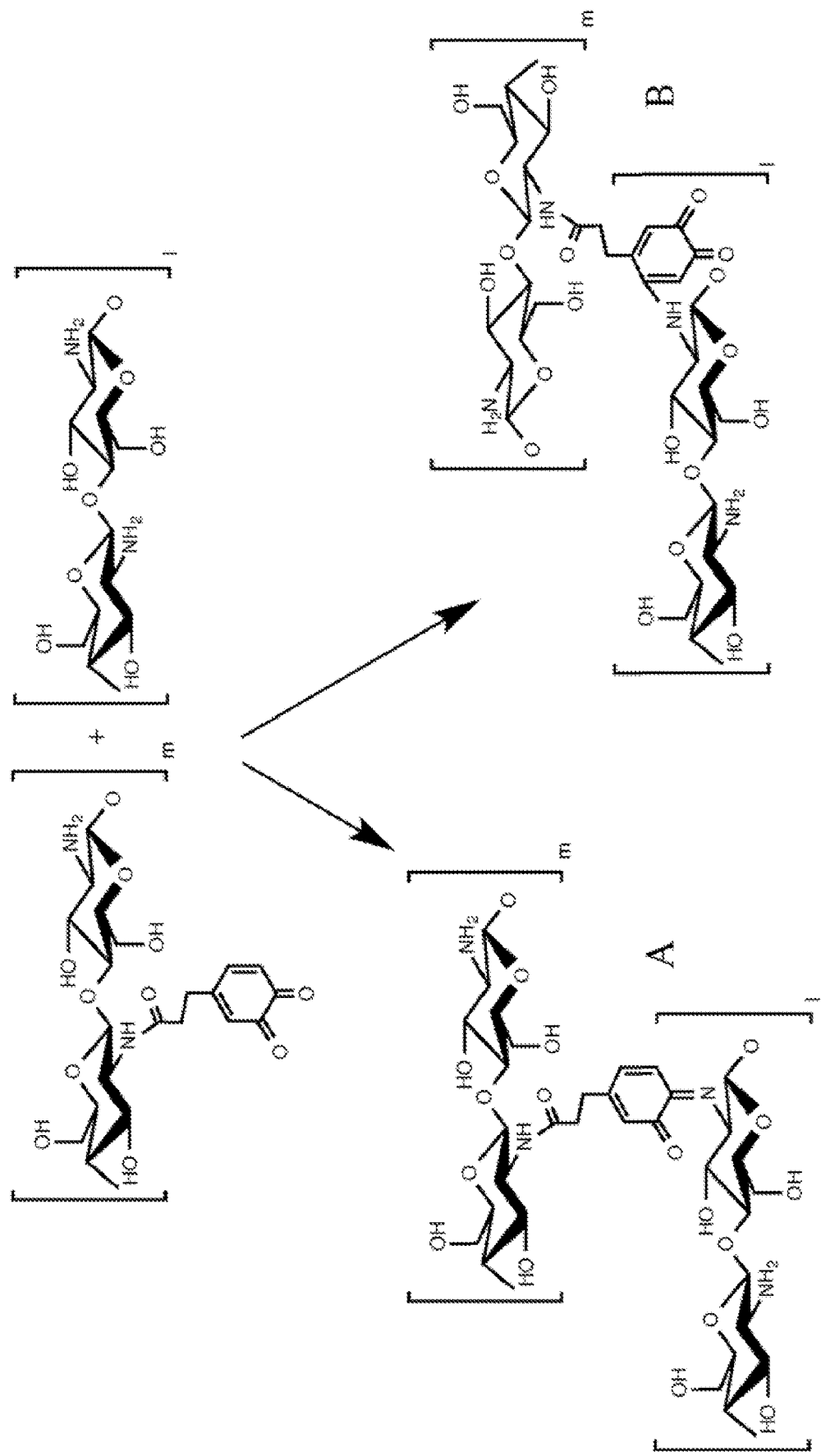
FIG. 4 depicts Schiff base (A) and Michael addition (B) reactions causing crosslinking between catechol modified chitosan and chitosan.

The swine are prepared using Chlorhexadine and draped in a sterile fashion. A midline laparotomy was performed to expose the stomach. Two 5-cm segment of the gastroepiploic vessels were dissected free from the gastric wall. For each segment, a 1-cm gastrotomy was made adjacent to the free but intact blood vessels. The artery was then pushed through the gastrotomy and positioned so that it is exposed to the gastric lumen. The gastric incision was then closed in a standard manner along with the abdominal wall (FIG. 2). An approximate 12 cm incision was made on anterior gastric wall to expose gastric cavity. The wound site and gastric vessels were then located and incised with a forceps to create a pulsatile bleeding. Before applied, the dressing bleed rate was determined using premeasured folded gauze sponges to absorb any blood from the wound over a 15 second period and weighed, multiplied ×4 to calculate bleed rate. The CGHD dressing was then placed over the bleed wound with a gauze sponge on top. Manual pressure is applied evenly over the patch for 30 seconds. At 30 seconds the gauze was removed and the area was observed for hemostasis initially and for up to 10 minutes. After 10-minutes observation, if achieved hemostasis, the gastric incision was closed in a layer fashion, i.e., wherein the surgeon sutures incised layers together consecutively. Then the abdominal wall was closed for 3-hours observation. At completion of 3-hours application, an upper endoscopy (GIF Type Q180, Olympus) was performed to identify the wound dressings for a visual examination. Then the incisions of abdomen and stomach were reopened for gross examination of the dressings. The CGHD dressings were removed and gave an adhesion score in accordance to how the dressing adhered to tissue surface using the Adherence Score System (Table 3).

At completion of these procedures, the wound sites were re-prepared by removal of old clots and residual of wound dressing to re-applied second sets of dressing as described above. Each wound site was used to test 2 dressings in this study phase.

Bleed Rate

Metzenbaum scissors were used to make a semi-transected vascular injury at gastric vessels to create a pulsatile bleeding. Bleed rate was measured with a pre-weighed gauze and recorded in g/min. Bleed rate for each injury was determined and recorded prior to dressing application.

Test Pieces were 20 mm×20 mm.

Eight dressings were tested from each type of Nanospun Chitosan (G01) and Chitosan Catechol Blend (F11).

Application of Test Pieces

The 30-second timer was started as the test piece was applied centrally over the injury and with sufficient pressure from fingers to stop bleeding. One piece of 50 mm×50 mm gauze was folded into two and applied over the 20 mm×20 mm test piece. Any subsequent pooled blood was suctioned from the site. After 30 seconds of light digital pressure (near 300 g load), fingers were removed and the test dressing observed for any sign of bleeding. If bleeding was observed, pressure was re-applied for 30 seconds. If hemostasis was achieved upon the release of the pressure, dressing was observed for 10 minutes. If there is no bleeding recurrence, the stomach wall was closed and observed through GI scope for 3 hours. If there was no bleeding recurrence after 3 hours, the dressing test piece was considered successful. If bleeding recurred within 5 minutes, the dressing was removed and a new dressing applied. Up to two reapplications were utilized.

TABLE 4 below summarizes the result of the study.

| Dressing Code# | # of dressing passed | | | # of dressings tested | % success |
|---|---|---|---|---|---|
| | 1st app | 2nd app | 3rd app | | |
| F11 | 3 | 1 | 2* | 13 | 46 |
| G01 | 0 | 3** | 1* | 12 | 31 |

*1 dressing from each group had extra dressing to stop oozing after 3$^{rd}$ pressure application
**1 dressing was held for extra 30 seconds Nanospun chitosan dressing (G01) had 4 successful application out of 12 dressings applied. While the 25% catechol/75% 2% chitosan dressing (F11) had 6 successful application out of 13 dressings tested. Two deviations were noted for the dressing applications: one dressing from each group had extra dressing to stop oozing that did not stop on swine #4; and one of nanospun chitosan dressing was held for extra 30 seconds.

On all applications, an endoscope was inserted to evaluate if the dressing was still present and hemostatic. In all cases, all dressings were confirmed as present, hemostatic and visible through the scope. After more than 3 hours of dressing application, the stomach was opened to allow the injury sites and dressings to be examined. All dressings were intact. Clot formation was observed on all wounds. It was noted in all cases of initial dressing success that there was no subsequent bleeding observed from the wounds at the 3 hour timepoint.

The final best dressing prototypes identified through testing in Examples 3, 4, and 5 demonstrated prolonged efficacy once they were adhered under light manual pressure with short duration application hold necessary for delivery through a standard gastroscope delivery port. The best dressings that were developed were amenable in a folded (or furled) configuration to be delivered through a standard diameter 2.8 mm diameter delivery channel from a standard gastroscope.

All CGHD dressings that achieved successful hemostasis (complete cessation of bleeding) in the first 10 minutes of application with no more than 3×30 second hold applications remained fully hemostatic through the 3 hour test period inside the closed porcine stomach. Success was achieved for 31% of g01 prototype applications and for 46% of the f11 prototype applications. The challenging nature of this study made success near 50% (i.e. F11 prototype) relevant to clinical application especially when it is noted that all initial successful mucoadhesive applications resulted in 100% success in the longer term. The mixed chitosan and catechol chitosan dressings provide for substantial resistance to digestive fluid digestion, are able to be folded/furled into the most complex and compact forms, and provide for good adhesive properties in conjunction with mixing with unmodified chitosan references.

Example 6

Demonstration of Dressing Deployment by Wire Device from Inside a 3.5 mm Diameter Channel The devices in this example comprise an expandable support that also serves as an axis.

Six prototype wire delivery devices of the invention depicted by FIG. 13 were prepared. Two thicknesses of nitinol wire were employed with three devices made using 0.32 mm diameter wire and three devices made using 0.24 mm diameter wire. The prototype wire device support body was acrylic rod 63 mm long and 3.2 mm diameter. The clear plastic sheath tubing was 72 mm long with internal diameter 3.5 mm and outer diameter 3.8 mm. Two pairs of nitinol wires (each 117 mm in length) were used for each device. The wires were set to fixed angles and articulated lengths in a salt oven in folding fixtures. Each wire was formed to contain two 2 mm long rod attachment points; two articulated spring arms, 30 mm long (14), to act in concert as the wire device support axis; two articulated 10 mm long dressing support connectors (15); and one base support spring strut 25 mm long (16). The folded wire pairs, oriented 90° to each along the wire support axis, were connected and glued to the acrylic support rod in 4×90° offset, 2 mm deep fines holes at the end of the rod so that the connected whole appeared as shown in FIG. 13c when looking down the wire axis.

An exemplary paper dressing (FIG. 13d) was attached by its back-folded tab attachment points (17) to the extremity wire ends (18) of FIG. 13c by cyanoacrylate glue. The dressing with wire delivery ends attached was folded to appearance of FIGS. 13e and 13f (looking down the wire axis) and the whole assembled and folded device was placed easily within the tube sheath of FIG. 13b with the side-on appearance of the whole close to that depicted of furled dressing and compacted wire device in the tubing of FIG. 13b.

Pushing of the compacted wire and furled dressing about 3 cm out of the confines of the tubing sheath resulted in repeatable, rapid (about 1 second) full opening and of the dressing.

Example 7

Demonstration of Dressing Deployment by Wire Device from Inside a 3.5 mm Diameter Channel. Nitinol Wire Delivery Device with Dressing Application Cross Struts with Central Loop Wire Connection Six prototype wire delivery devices of the invention depicted by FIGS. 14a & 14b were prepared. Two thicknesses of nitinol wire were employed with three devices made using 0.32 mm diameter wire and three devices made using 0.24 mm diameter wire. The prototype wire device support body was acrylic rod 63 mm long and 3.2 mm diameter. The clear plastic sheath tubing was 72 mm long with internal diameter 3.5 mm and outer diameter 3.8 mm. Two pairs of nitinol wires (each 117 mm in length) were used for each device. The wires were set to fixed angles and articulated lengths in a molten salt bath in folding fixtures. Each wire was formed to contain two single wire width rod attachment points; two articulated spring arms, 30 mm long (14), to act in concert as the wire device support axis; two articulated 10 mm long dressing support connectors (15); and one base support spring strut 25 mm long (16) with central small diameter (1.5 mm diameter) 360° coil for fixing the struts together centrally to remove possibility of slippage. The folded wire pairs, oriented 90° to each along the wire support axis, were connected (central strut coils intertwined) and glued to the acrylic support rod in 4×90° offset, 2 mm deep fines holes at the end of the rod so that the connected whole appeared as shown in FIG. 13b when looking down the wire axis.

A 2.5 cm diameter catechol chitosan dressing was attached by its back-folded tab attachment points (17) to the extremity wire ends (18) of FIG. 14b by either of two methods. Direct cyanoacrylate gluing of the dressing surface to the nitinol wire strut as used in example 1 was not effective in attaching the freeze phase separated, dry, compressed catechol chitosan dressing because the surface of the chitosan dressing was not sufficiently strong (<5 g) to hold the load of the attachment. Because of the problem of surface fibrillation/delamination, small needle holes (near 500 microns diameter) were made using a sharp needle point through the dressing tabs without creation of any tearing or cracking and the edges of the holes were reinforced with a micro-application (by sharp tipped wooden probe) of cyanoacrylate glue on the surfaces of the holes including small areas around the extremity edges of the holes without closing the perforations with cyanoacrylate. After curing of the cyanoacrylate treated catechol chitosan in the holes, the holes demonstrated at least 10× greater strength than the chitosan catechol surface. The reinforced through and through holes were then used as fiber attachment points to the nitinol wire ends (18) of the delivery device with the fiber being tied in a loop around the nitinol wire ends and the fiber glued by cyanoacrylate to the wire to resist any possibility of the fiber loop sliding along the wire. Direct cyanoacrylate glue attachment of the nitinol wire ends to the cyanoacrylate reinforced holes was also demonstrated as an option to provide good local attachment of around 50-100 g to a nitinol end.

The dressing attached by chitosan microfiber looped through the cyanoacrylate reinforced holes to the wire delivery ends of the device of FIG. 14 was folded to appearance of FIGS. 13e and 13f (looking down the wire axis) and the whole assembled and folded device was placed within the 3.5 mm internal diameter tube sheath with the side-on appearance of the whole close to that depicted of furled dressing and compacted wire device in the tubing of FIG. 13b. Pushing of the compacted wire and furled dressing about 3 cm out of the confines of the tubing sheath resulted in full opening of the catechol chitosan dressing in about 3 seconds.

REFERENCES

1. HCUP, Outcomes by 153 Gastrointestinal hemorrhage, in U.S.Department of Health & Human/HCUPnet2014, U.S.Department of Health & Human Services: Washington D.C.
2. Rockey, D. C., Gastrointestinal bleeding. Gastroenterol Clin North Am, 2005. 34(4): p. 581-8.
3. Crooks, C. J., West, J., and Card, T. R., Upper gastrointestinal hemorrhage and deprivation: a nationwide cohort study of health inequality in hospital admissions. Gut, 2012. 61(4): p. 514-20.
4. Jairath, V., Kahan, B. C., Logan, R. F., Hearnshaw, S. A., Travis, S. P., Murphy, M. F., and Palmer, K. R., Mortality from acute upper gastrointestinal bleeding in the United kingdom: does it display a "weekend effect"? Am J Gastroenterol, 2011. 106(9): p. 1621-8.
5. Sung, J. J., Tsoi, K. K., Ma, T. K., Yung, M. Y., Lau, J. Y., and Chiu, P. W., Causes of mortality in patients with peptic ulcer bleeding: a prospective cohort study of 10,428 cases. Am J Gastroenterol, 2010. 105(1): p. 84-9.
6. Jairath, V., Kahan, B. C., Stanworth, S. J., Logan, R. F., Hearnshaw, S. A., Travis, S. P., Palmer, K. R., and Murphy, M. F., Prevalence, management, and outcomes of patients with coagulopathy after acute nonvariceal upper gastrointestinal bleeding in the United Kingdom. Transfusion, 2013. 53(5): p. 1069-76.
7. Elta, G. H., Approach to the patient with gross gastrointestinal bleeding. Textbook of Gastroenterology, 2003. In: Yamada T., Alper, D. H., Editors (Lippincott Williams & Wilkins): p. 698-723.
8. Boonpongmanee, S., Fleischer, D. E., Pezzullo, J. C., Collier, K., Mayoral, W., Al-Kawas, F., Chutkan, R., Lewis, J. H., Tio, T. L., and Benjamin, S. B., The frequency of peptic ulcer as a cause of upper-GI bleeding is exaggerated. Gastrointest Endosc, 2004. 59(7): p. 788-94.
9. Jairath, V., Martel, M., Logan, R. F., and Barkun, A. N., Why do mortality rates for nonvariceal upper gastrointestinal bleeding differ around the world? A systematic review of cohort studies. Can J Gastroenterol, 2012. 26(8): p. 537-43.

10. Sheibani, S., Kim, J. J., Chen, B., Park, S., Saberi, B., Keyashian, K., Buxbaum, J., and Laine, L., Natural history of acute upper GI bleeding due to tumours: short-term success and long-term recurrence with or without endoscopic therapy. Aliment Pharmacol Ther, 2013. 38(2): p. 144-50.
11. Adler, D. G., Leighton, J. A., Davila, R. E., Hirota, W. K., Jacobson, B. C., Qureshi, W. A., Raj an, E., Zuckerman, M. J., Fanelli, R. D., Hambrick, R. D., Baron, T., and Faigel, D. O., ASGE guideline: The role of endoscopy in acute non-variceal upper-GI hemorrhage. Gastrointest Endosc, 2004. 60(4): p. 497-504.
12. Banerjee, S., Cash, B. D., Dominitz, J. A., Baron, T. H., Anderson, M. A., Ben-Menachem, T., Fisher, L., Fukami, N., Harrison, M. E., Ikenberry, S. O., Khan, K., Krinsky, M. L., Maple, J., Fanelli, R. D., and Strohmeyer, L., The role of endoscopy in the management of patients with peptic ulcer disease. Gastrointest Endosc, 2010. 71(4): p. 663-8.
13. Peng, Y. C., Chen, S. Y., Tung, C. F., Chou, W. K., Hu, W. H., and Yang, D. Y., Factors associated with failure of initial endoscopic hemoclip hemostasis for upper gastrointestinal bleeding. J Clin Gastroenterol, 2006. 40(1): p. 25-8.
14. Peng, Y. C., Tung, C. F., Chow, W. K., Chen, S. Y., and Chang, C. S., Factors contributing to the failure of argon plasma coagulation hemostasis in patients with non-variceal upper gastrointestinal tract bleeding. Hepatogastroenterology, 2010. 57(101): p. 781-6.
15. Karaman, A., Baskol, M., Gursoy, S., Torun, E., Yurci, A., celikbilek, M., Guven, K., Ozbakir, O., and Yucesoy, M., Endoscopic topical application of ankaferd blood Stopper® in gastrointestinal bleeding. Journal of Alternative and Complementary Medicine, 2012. 18(1): p. 65-68.
16. Halkerston, K., Evans, J., Ismail, D., Catnach, S., Chaudhary, R., Fullard, M., King, A., and Leahy, A., PWE-046 Early Clinical Experience of Endoclot™ in the Treatment of Acute Gastro-Intestinal Bleeding. Gut, 2013. 62(Suppl 1): p. A149.
17. Holster, I. L., Kuipers, E. J., and Tjwa, E. T. T. L., Hemospray in the treatment of upper gastrointestinal hemorrhage in patients on antithrombotic therapy. Endoscopy, 2013. 45(1): p. 63-66.
18. Sung, J. J. Y., Luo, D., Wu, J. C. Y., Ching, J. Y. L., Chan, F. K. L., Lau, J. Y. W., MacK, S., Ducharme, R., Okolo, P., Canto, M., Kalloo, A., and Giday, S. A., Early clinical experience of the safety and effectiveness of Hemospray in achieving hemostasis in patients with acute peptic ulcer bleeding. Endoscopy, 2011. 43(4): p. 291-295.
19. Yau, A. H. L., Ou, G., Galorport, C., Amar, J., Bressler, B., Donnellan, F., Ko, H. H., Lam, E., and Enns, R. A., Safety and efficacy of Hemospray® in upper gastrointestinal bleeding. Canadian Journal of Gastroenterology and Hepatology, 2014. 28(2): p. 72-76.
20. Kheirabadi, B. S., Mace, J. E., Terrazas, I. B., Fedyk, C. G., Estep, J. S., Dubick, M. A., and Blackbourne, L. H., Safety Evaluation of New Hemostatic Agents, Smectite Granules, and Kaolin-Coated Gauze in a Vascular Injury Wound Model in Swine. Journal of Trauma and Acute Care Surgery, 2010. 68(2): p. 269-278.

The invention claimed is:

1. A gastrointestinal delivery device comprising:
an expandable support; and
a releasable dressing;
wherein the device is capable of fitting through a channel of 4 mm diameter or less when the expandable support is in an unexpanded format, wherein the releasable dressing comprises a catechol modified chitosan, wherein the dressing is tissue adhesive, hemostatic, and has a thickness that is 500 microns or less, and wherein the dressing is at least one of (i) resistant to substantial swelling in presence of biological fluid or (ii) porous.

2. The gastrointestinal delivery device according to claim 1, wherein the device is capable of fitting through one of: a channel of 3.8 mm diameter or less; a channel of 3.5 mm or less; or a channel of 3.2 mm or less.

3. The gastrointestinal delivery device according to claim 1, wherein the device further comprises a sheath that envelopes the expandable support and the dressing.

4. The gastrointestinal delivery device according to claim 1, further comprising an axis connected to the expandable support.

5. The gastrointestinal delivery device according to claim 4, wherein the expandable support comprises at least two articulated spring arms connecting to the releasable dressing and two or more articulated base support spring struts.

6. The gastrointestinal delivery device according to claim 5, wherein the at least two articulated spring arms connect to both the axis and the base support spring struts.

7. The gastrointestinal delivery device according to claim 6, wherein the axis comprises a wire.

8. The gastrointestinal delivery device according to claim 4, wherein the axis comprises articulated spring arms.

9. The gastrointestinal delivery device according to claim 4, further comprising a spring locator positioning arm, wherein the spring locator positioning arm comprises a first end connecting to the axis and a second end connecting to the expandable support.

10. The gastrointestinal delivery device according to claim 4, wherein the axis is also the expandable support.

11. The gastrointestinal delivery device according to claim 1, wherein the expandable support comprises an annular shape in an expanded format configuration.

12. The gastrointestinal delivery device according to claim 1, wherein the expandable support comprises a ribbon spring annular dressing support.

13. The gastrointestinal delivery device according to claim 1, wherein the expandable support comprises more than one wire.

14. The gastrointestinal delivery device according to claim 1, wherein the expandable support comprises a stable balloon in an expanded format configuration.

15. The gastrointestinal delivery device according to claim 1, wherein the expandable support comprises an umbrella style wire frame.

16. The gastrointestinal delivery device according to claim 1, wherein the releasable dressing further comprises one or more dressing tabs, and wherein the releasable dressing is attached to the expandable support at a dressing tab.

17. The gastrointestinal delivery device according to claim 16, wherein the one or more dressing tabs are reinforced by at least one of increased dressing density, increased dressing thickness, and/or sewn fibers.

18. The gastrointestinal delivery device according to claim 1, wherein all components of the device other than the releasable dressing consist of wires and, optionally, spring wires.

19. The gastrointestinal delivery device according to claim 18, wherein all components of the device other than the releasable dressing consist of a single wire and, optionally, a spring wire.

20. A method of delivering a releasable dressing in vivo to a target tissue site in the gastrointestinal tract using the device according to claim 4, comprising:
   a) fitting the expandable support, the releasable dressing, and the axis into a narrow channel of 4 mm diameter or less;
   b) expanding the expandable support at a target tissue site;
   c) adhering the releasable dressing to the target tissue site by applying light pressure;
   d) collapsing the expandable support; and
   e) removing the expandable support and the axis from the target tissue site.

21. A method of treating gastrointestinal bleeding using the gastrointestinal delivery device according to claim 4, comprising
   a) fitting the expandable support, the releasable dressing, and the axis into a narrow channel of 4 mm diameter or less;
   b) expanding the expandable support at a target tissue site;
   c) adhering the releasable dressing to the target tissue site; and
   d) stopping gastrointestinal bleeding.

22. The method according to claim 21 further comprising applying light pressure on the releasable dressing at the target tissue site.

23. The method according to claim 22, wherein the light pressure is about 200-300 g.

24. The method according to claim 22, wherein the light pressure is applied for about 10 to 60 seconds.

25. The method according to claim 21, wherein the released dressing stops oozing to serious hemorrhagic (≥Forrest 1a UGIB) oozing bleeding at a rate of about 1 ml/min to about 150 ml/min.

26. The method according to claim 21, wherein the narrow channel is a channel of a gastroscope or a delivery port of a gastroscope.

27. The method according to claim 21, further comprising terminally sterilizing the device.

28. The method according to claim 27, wherein the releasable dressing is terminally sterilized.

\* \* \* \* \*